United States Patent [19]

Sperl et al.

[11] Patent Number: 5,939,417

[45] Date of Patent: Aug. 17, 1999

[54] 1,3,6-TRIHYDRO-6-AZA-3-OXAPENTALEN-2-ONE DERIVATIVES FOR THE TREATMENT OF NEOPLASIA

[75] Inventors: Gerhard Sperl, Horsham; Rifat Pamukcu, Spring House, both of Pa.

[73] Assignee: Cell Pathways Inc, Horsham, Pa.

[21] Appl. No.: 09/174,815

[22] Filed: Oct. 19, 1998

[51] Int. Cl.$^6$ ........................ A61K 31/505; C07D 491/08
[52] U.S. Cl. .................... 514/253; 514/254; 514/256; 544/333; 544/373; 544/405
[58] Field of Search ........................ 514/253, 254, 514/255, 256, 269, 412, 421; 544/295, 296, 333, 334, 298, 336, 357, 359, 373, 382, 384, 368, 402, 403, 405; 548/453, 512

[56] References Cited

U.S. PATENT DOCUMENTS 3,865,840  2/1975  Carson ..................................... 548/531
5,696,159  12/1997  Gross et al. ............................ 514/468

*Primary Examiner*—Robert W. Rausuer
*Assistant Examiner*—John J. Dolan
*Attorney, Agent, or Firm*—Robert W. Stevenson

[57] ABSTRACT

1,3,6-Trihydro-6-Aza-3-Oxapentalen-2-One Derivatives for inhibiting neoplastic conditions.

24 Claims, No Drawings

1,3,6-TRIHYDRO-6-AZA-3-OXAPENTALEN-2-ONE DERIVATIVES FOR THE TREATMENT OF NEOPLASIA

TECHNICAL FIELD

This invention relates to compounds and methods for inducing or promoting apoptosis and for arresting uncontrolled neoplastic cell proliferation, methods that are specifically useful in the arresting and treatment of neoplasias, including precancerous and cancerous lesions.

BACKGROUND OF THE INVENTION

Pharmaceuticals that are effective against early stage neoplasias comprise an emerging and expanding area of research and potential commercial development. Such pharmaceuticals can delay or arrest development of precancerous lesions into cancers. Each year in the United States alone, untold numbers of people develop precancerous lesions, which exhibit a strong statistically significant tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), cervical dysplasia (cervical cancer) and other such neoplasms.

Such compounds and methods are particularly beneficial to sub-populations of patients who repeatedly develop precancerous lesions, and therefore have a statistically higher probability of getting cancer. Many cancer types (e.g., breast, colon, prostate etc.) have such patient sub-populations.

The search for drugs useful for treating and preventing neoplasias in their earliest stages is intensive because chemotherapy and surgery on cancer itself is often not effective, and current cancer chemotherapy has severe side effects. Such cancer-preventative compounds are also envisaged for recovered cancer patients who retain a risk of cancer reoccurrence, and even for cancer patients who would benefit from compounds that selectively induce apoptosis in neoplastic, but substantially not in normal cells.

Because it is believed that chronic administration of cancer-preventative pharmaceuticals is necessary to inhibit or arrest the development of neoplasia, standard cancer chemotherapeutic drugs are not considered appropriate drugs for cancer chemoprevention because whatever cancer preventative (as opposed to cancer-fighting) capabilities those drugs may possess do not outweigh their severe side effects. Most standard chemotherapeutics are now believed to kill cancer cells by inducing apoptosis (also sometimes referred to as "programmed cell death"). Apoptosis naturally occurs in many tissues in the body. Apoptosis plays a critical role in tissue homeostasis, that is, it ensures that the number of new cells produced are correspondingly offset by an equal number of cells that die. Apoptosis is especially pronounced in self-renewing tissues such as bone marrow, immune cells, gut, and skin. For example, the cells in the intestinal lining divide so rapidly that the body must eliminate cells after only three days to protect and prevent the overgrowth of the intestinal lining.

Standard chemotherapeutics promote apoptosis not only in cancer cells, but also in normal human tissues, and therefore have a particularly severe effect on tissues where apoptosis is especially pronounced (e.g. hair, gut and skin). The results of those effects include hair loss, weight loss, vomiting and bone marrow immune suppression. Thus, standard chemotherapeutics are inappropriate for cancer prevention, particularly if chronic administration is indicated.

Several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the continued prophylactic use of currently available NSAIDs, even in high colon cancer-risk patients, is still marked by severe side reactions that include gastrointestinal irritations, perforations, ulcerations and kidney toxicity believed to be produced by inhibition of prostaglandin synthetase activity ("PGE-2"). Such inhibition is a requirement for the NSAIDs anti-inflammatory action since elevated levels of PGE-2 are associated with inflammation. PGE-2 plays a protective function in the gastrointestinal tract, which is the reason such gastric side effects arise with chronic NSAID therapy, which is rarely indicated for arthritis sufferers, acute therapy being the norm for them. However, chronic administration of sulindac is important for high cancer-risk patients to eliminate and prevent future polyps which cause gastric side effects in many such patients. Once NSAID treatment is terminated due to such complications, the neoplasms return, particularly in high risk patients.

Compounds such as those disclosed in U.S. Pat. No. 5,643,959 have exhibited advantages in the treatment of neoplastic lesions since such compounds have been shown to induce apoptosis in neoplastic cells but not in normal cells in humans (see Piazza et al. Gastroenterology Vol. 112, A629, 1997). Thus, the severe side effects due to induction of apoptosis in normal cells by conventional chemotherapeutics are avoided by these novel therapeutics (see, Piazza et al. Cancer Research Vol. 57, pp. 2452–2459, 1997). In addition, such compounds do not exhibit the gastric side effects associated with NSAIDs since such compounds do not substantially inhibit PGE-2. More potent compounds with such neoplasia specificity but without substantial PGE-2 activity are desirable.

SUMMARY OF THE INVENTION

This invention represents potent compounds that inhibit the growth of neoplastic cells, for treating patients with neoplastic lesions. This invention also involves methods for inducing such specific inhibition of neoplastic cells by exposing such cells to a pharmacologically effective amount of those compounds described below to a patient in need of such treatment. Such compositions are effective in modulating the growth of neoplasms.

DETAILED DESCRIPTION OF THE INVENTION

As discussed above, the present invention includes compounds of Formula I below (as well as their pharmaceutically acceptable salts) for treating a patient with neoplastic, particularly precancerous, and cancerous lesions:

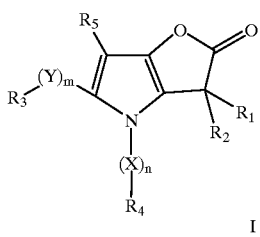

Formula I wherein $R_1$ and $R_2$ are independently selected from the group consisting of hydrogen, lower alkyl, and benzyl;

$R_3$ is selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, tetrazolyl, morpholinyl, triazinyl, furfuryl, and thiophenyl, and lower alkyl, wherein said substitutents are one to three independently selected from the group consisting of halogen, lower alkyl, lower alkoxy, amino, lower alkylamino, di-lower alkylamino, hydroxy, nitro, nitrile, carboxyl, aminosulfonyl, lower alkyl mercapto, and lower alkylsulfonyl;

$R_4$ is selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, tetrazolyl, morpholinyl, triazinyl, furfuryl, thiophenyl, and lower alkyl; wherein said substitutents are one to three independently selected from the group consisting of halogen, lower alkyl, lower alkoxy, amino, lower alkylamino, di-lower alkylamino, hydroxy, nitro, nitrile, carboxyl, aminosulfonyl, lower alkyl mercapto, and lower alkylsulfonyl;

$R_5$ is selected from the group consisting of hydrogen, lower alkyl, halogen, hydroxy, amino, lower alkyl amino, and dilower alkylamino;

Y is selected from the group consisting of $CH_2$, $C=O$, CH—OH m is an integer from 0—3

X is selected from the group consisting of $CH_2$, $C=O$, CH—OH, and $SO_2$; and n is an integer from 0—2.

Preferred compounds of this invention include those where $R_1$ and $R_2$ are independently selected from the group consisting of hydrogen and lower alkyl;

$R_3$ is selected from the group consisting of substituted or unsubstituted phenyl, pyridinyl, pyrrolyl, pyrazolyl, imidazolyl, pyrazinyl, pyrimidinyl, triazinyl, furfuryl, thiophenyl, and lower alkyl, wherein said substituents are one to three independently selected from the group consisting of lower alkyl, lower alkoxy, amino, lower alkylamino, and di-lower alkylamino, carboxyl, aminosulfonyl and alkylsulfonyl.

$R_4$ is selected from the group consisting of substituted or unsubstituted phenyl, pyridinyl, pyrroyl, imidazolidinyl, pyrazinyl, piperazinyl, pyrimidinyl, morpholinyl, triazinyl, thiophenyl, and lower alkyl, wherein said substituents are one to three independently selected from the group consisting of lower alkoxy, amino, di-lower-alkylamino, hydroxy, nitrile, carboxyl, aminosulfonyl and alkylsulfonyl;

$R_5$ is selected from the group consisting of hydrogen, lower alkyl, hydroxy and diloweralkylamino;

Y is selected from the group consisting of CH—OH and $C=O$;

m is an integer from 0–2;

X is selected from the group consisting of $CH_2$, $C=O$ and $SO_2$; and n is either 0 or 1

More preferred compounds of this invention include those wherein $R_1$ and $R_2$ are both lower alkyl;

$R_3$ is selected from the group consisting of phenyl, pyridinyl, pyrazinyl, pyrimidinyl, and triazinyl, wherein said substituents are one to three independently selected from the group consisting of lower alkyl, lower alkoxy, di-lower-alkylamino, aminosulfonyl and alkyl sulfonyl;

$R_4$ is selected from the group consisting of substituted or unsubstituted phenyl, pyridinyl, pyrazinyl, pyrimidinyl, morpholinyl, triazinyl, thiophenyl, and lower alkyl, wherein said substituents are one to three independently selected from the group consisting of lower alkoxy, di-lower-alkylamino, aminosulfonyl and alkylsulfonyl.

$R_5$ is selected from the group consisting of hydrogen and lower alkyl;

Y is $C=O$;

M is 0 or 1;

X is $CH_2$; and n=0

The present invention is also a method of treating individuals with neoplastic lesions by administering a pharmacologically effective amount of an enterically coated pharmaceutical composition that includes compounds of this invention.

Preferably, such compounds are administered without therapeutic amounts of an NSAID.

Also, the present invention is a method of inhibiting the growth of neoplastic cells by exposing the cells to an effective amount of compounds of Formula I As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "cancerous" refers to lesions that are malignant. Examples include malignant melanomas, breast cancer, prostate cancer and colon cancer.

As used herein, the term "neoplasm" refers to both precancerous and cancerous lesions and hyperplasia.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

The term "lower alkoxy" refers to alkoxy groups having from 1 to 8 carbons, including straight, branched or cyclic arrangements.

The term "lower alkylmercapto" refers to a sulfide group that is substituted with a lower alkyl group; and the term "lower alkyl sulfonyl" refers to a sulfone group that is substituted with a lower alkyl group.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmetate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

It will be appreciated that certain compounds of Formula I can possess an asymmetric carbon atom and are thus capable of existing as enantiomers. Unless otherwise specified, this invention includes such enantiomers, including any racemates. The separate enantiomers may be synthesized from chiral starting materials, or the racemates can be resolved by conventional procedures that are well known in the art of chemistry such as chiral chromatography, fractional cyrstallization of diastereomeric salts and the like.

Compounds of this invention may be formulated into pharmaceutical compositions together with pharmaceutically acceptable carriers for oral administration in solid or liquid form, or for intraveneous, rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement of the active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

The general scheme for producing compounds useful in this invention is illustrated and explained below.

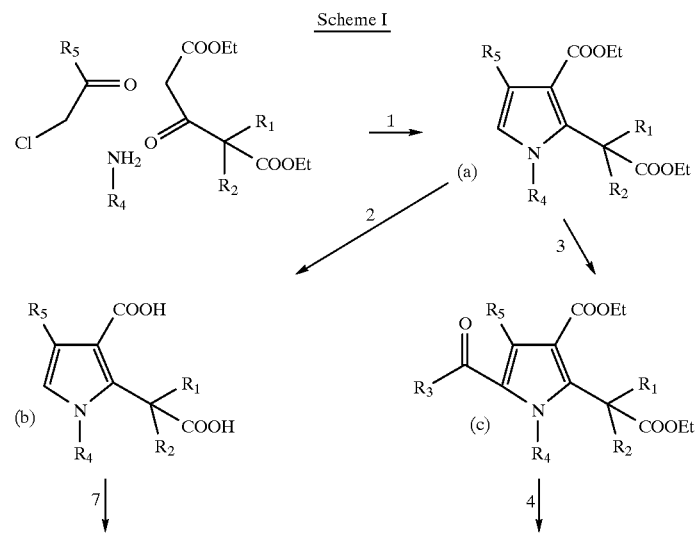

Scheme I

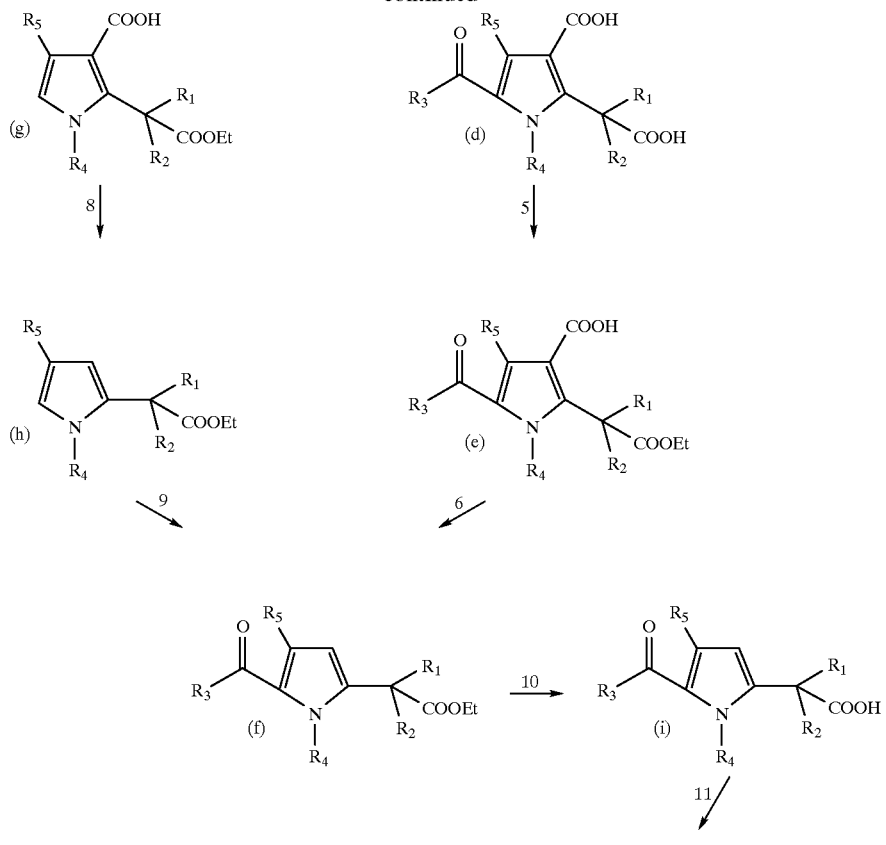

Scheme I describes the general procedure which leads to compounds of Formula I. An appropriate chloromethyl lower alkylketone ($R_5$—C(O)—$CH_2$—Cl) is added to a mixture of an appropriate di-loweralkylacetone dicarboxylate, preferably the diethylester ($EtO_2C$—$CH_2$—C(O)—C($R_1$, $R_2$)—$CO_2Et$) and a lower alkylamine ($R_4$—$NH_2$), preferably in an aqueous medium. The reaction temperature is preferably maintained just below 60° C., and after a few hours, the mixture is treated with ice-hydrochloric acid (reaction 1). The thus obtained ring-closed pyrrole (a) is acylated with an acyl halide under Friedel-Crafts reaction conditions to give the pyrrole-ester (c) (reaction 3). The 5-acyl product (c) is subjected to a hydrolysis with moderately concentrated alkali (e.g., NaOH) to yield the free di-acid (d) (reaction 4), which is partly reesterified with an acidic solution of ethanol to give the 5-acyl-3-carboxy-pyrrole-ester derivative (e) (reaction 5). Decarboxylation of the carboxy group in 3-position is accomplished by heating (e) in a suitable organic solvent (reaction 6) to yield the alkyl 5-acyl-pyrrole-ester-derivative (f), which is hydrolysed (e.g., with NaOH) to give the free acid (i) (reaction 10). The pyrrole acid derivative (i) is subjected to N-bromosuccunimide to yield the lactone (j) (reaction 11).

In an alternative way to achieve the lactone (j), the acyl rest in 5-position is added at a later stage. Starting with the pyrrole derivative (a), hydrolysis in the usual manner (e.g., with NaOH; see, reaction 2) gives the dicarboxylic acid (b). Partial reesterification with an acidic solution of ethanol yields the 3-carboxy-pyrrole-ester derivative (g) (reaction 7), which is decarboxylated in the 3-position by heating it in a suitable solvent (e.g., quinoline) (reaction 9). The resulting pyrrole-ester (h) is subjected to a Friedel Crafts reaction with an acylhalide to yield the 5-acyl-pyrrole-ester derivative (f), which is converted to the lactone (j), as described above (see reactions 10 and 11).

Scheme II
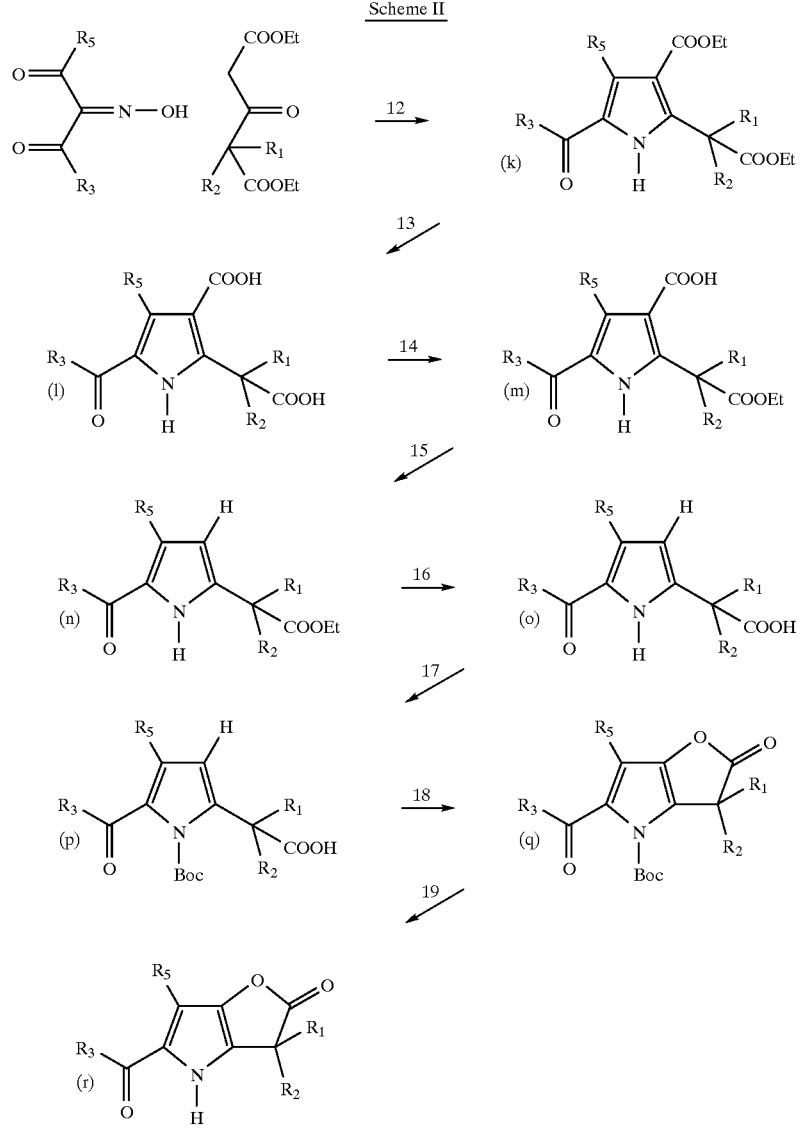
Scheme III
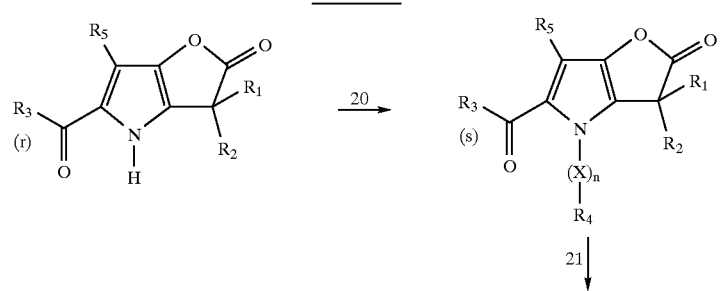

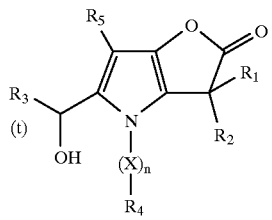

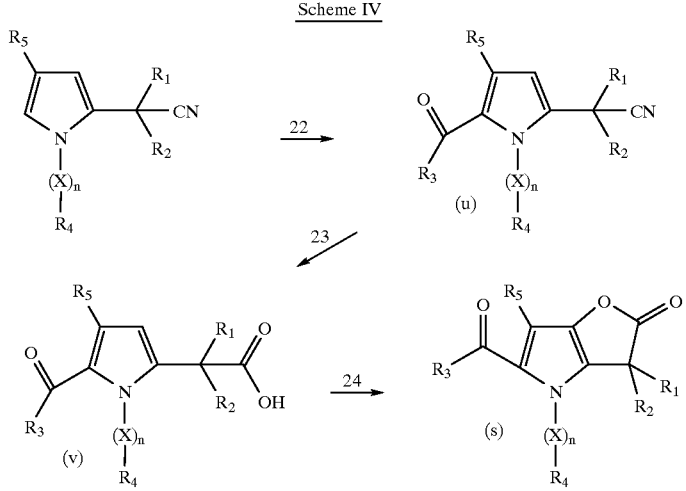

Scheme IV

Scheme II is employed when $R_4$ is hydrogen. A substituted oxime and a substituted ethylacetonedicarboxylate are allowed to react according to a Knorr pyrrole synthesis in glacial acetic acid and zinc dust to yield the ring closed pyrrole (k) (reaction 12). Hydrolysis of the diester (k) with a moderately concentrated alkali (e.g., NaOH) gives the free dicarboxylic acid (l) (reaction 13), which is re-esterified with an acidic ethanol solution (reaction 14) to yield the ethyl 5-acyl-3-carboxy pyrrole ester derivative (m). Decarboxylation of the carboxy group in 3-position is accomplished by heating the ester (m) in an organic solvent (e.g., quinoline) (reaction 15) to give the pyrrole-ester (n), which is hydrolysed in the usual manner (e.g., with NaOH) to yield the free acid (o) (reaction 16). After protecting the secondary amine by reaction with t-butyloxycarbonyl-anhydride (reaction 17), the lactone (q) is formed by reaction with N-bromosuccinimide (reaction 18). The BOC-group is removed with trifluoroacetic acid, followed by a mild basic workup (e.g., NaHCO₃) to yield the lactone (r) (reaction 19).

Scheme III is employed if $R_4$ is a group which is sensitive towards Friedel Crafts conditions, (i.e., Reactions 9 or 3 in Scheme I). The lactone (r) in a basic solution is allowed to react with an alkylhalide($R_4$—$(X)_n$—Hal), acylhalide or sulfonyl halide to give the N-substituted lactone (s) (reaction 20), which can be reduced with sodium borohydride to the lactone (t) with a secondary alcohol in position 5 (reaction 21).

Scheme IV is employed if a nitrile, i.e., 1-methyl-pyrrole-2-acetonitrile, is available as a starting material for reaction 22, which is a Friedel Crafts acylation with $R_3$—C(O)—Cl and AlCl₃ as reagents. The nitrile (u) is hydrolysed with base (reaction 23) to give the acid (v). The lactone (s) is formed by reaction with N-bromosuccinimide (reaction 24).

To summarize, the reagents and conditions for Scheme I–III are as follows (numbers refer to reactions):

1. aqueous solution, <60° C.; H⁺
2. A) NaOH (25–50%) B) HCl
3. Friedel-Crafts reaction with $R_3$—C(O)—Cl
4. A) NaOH (25–50%) B) HCl
5. EtOH, H⁺
6. Δ, quinoline, —CO₂ ↑
7. EtOH, H⁺ (Other lower alkylalcohols can be employed instead of ethanol.)
8. Δ, quinoline, —CO₂ ↑
9. Friedel-Crafts reaction with $R_3$—C(O)—Cl
10. A) NaOH (25–50%) B) HCl
11. N-bromosuccinimide
12. Knorr pyrrole synthesis conditions: Zn/CH₃COOH
13. A) NaOH (25–50%) B) HCl
14. EtOH, H⁺ (Other lower alkylalcohols can be employed instead of ethanol)
15. Δ, quinoline, —CO₂ ↑
16. A) NaOH (25–50%); B) HCl
17. (BOC)₂O
18. N-bromosuccinimide
19. A) CF₃COOH/CH₂Cl₂ B) base
20. $R_4$—$(X)_n$—Hal
21. NaBH₄
22. Friedel-Crafts reaction with $R_3$—C(O)—Cl
23. 1N NaOH reflux
24. N-Bromosuccinimide The following examples are intended to illustrate, but not to limit, the scope of the present invention.

EXAMPLE 1

6-Methyl-5-(p-Toluoyl)-1,3,6-Trihydro-6-Aza-3-Oxapentalen-2-One (A) 5-(p-Toluoyl)-1-methylpyrrole-2-acetonitrile To a cooled suspension of 26.6 g. (0.2 mole) aluminum chloride in 80 ml. dichloroethane is added dropwise 30.8 g. (0.2 mole) p-toluoyl chloride. The resulting solution is added dropwise to a solution of 1-methylpyrrole-2-acetonitrile in 80 ml. dichloroethane cooled externally with an ice bath. After the addition, the resulting solution is stirred at room temperature for twenty minutes and then refluxed for three minutes. The solution is poured into ice acidified with dilute hydrochloric acid. The organic and aqueous fractions are separated. The aqueous fraction is extracted once with chloroform. The organic fractions are combined and washed successively with N,N-dimethyl-1,3-propanediamine, dilute hydrochloric acid, saturated sodium bicarbonate solution and saturated sodium chloride solution. The organic fraction is dried over anhydrous magnesium sulfate. The solvent is then evaporated off. Upon trituration of the residue with methanol, a solid crystallizes, 5-(p-toluoyl)-1-methylpyrrole-2-acetonitrile, which is removed by filtration and purified by recrystallization from benzene. Additional product is isolated from the mother liquors which are combined, concentrated in vacuo, and the resulting oily residue column chromatographed on neutral alumina using hexane, benzene and ether as successive solvents. The product is isolated by concentrating in vacuo the first few major compound-bearing fractions (10% ether in benzene). The solids are combined and recrystallized from methanol and then from benzene-hexane, m.p. 102–105° C.

(B) 5-(p-Toluoyl)-1-methylpyrrole-2-acetic acid

A solution of 3.67 g. (0.015 mole) of 5-(p-toluoyl)-1-methylpyrrole-2-acetonitrile, 24 ml. of 1N sodium hydroxide, and 50 ml. of 95% ethanol is stirred and refluxed for twenty-four hours. The resulting solution is poured into ice acidified with dilute hydrochloride acid. A white solid precipitates which is extracted into ether. The ether phase is washed with a saturated solution of sodium chloride and dried over anhydrous magnesium sulfate. The solvent is evaporated and a white solid, 5-(p-toluoyl)-1-methylpyrrole-2-acetic acid, is obtained which is recrystallized twice from isopropanol, m.p. 155–157° C.

(C) 6-Methyl-5-(p-toluoyl)-1,3,6-trihydro-6-aza-3-oxapentalen-2-one

N-bromosuccinimide (0.94 g, 5.2 mmol) is added stepwise at 0° C. to a stirred solution of 5-(p-toluoyl)-1-methylpyrrole-2-acetic acid (0.70 g, 2.39 mmol) in DMA/water (6 ml, 0.1 ml). After 30 minutes at 0° C., stirring is continued overnight at room temperature. The solution is added dropwise to stirred ice water (150 ml). A white precipitate is filtered off, is washed with water (2×10 ml), and is dried in vacuo. Recrystallization from methylene chloride-n-hexane gives a white solid, 6-methyl-5-(p-toluoyl)-1,3,6-trihydro-6-aza-3-oxapentalen-2-one, with m.p. 148–151° C. ($R_1$=H, $R_2$=H, $R_3$=4-methylphenyl, $R_4$=$CH_3$, $R_5$=H, Y=CO, m=1, n=0). Formula: $C_{15}H_{13}NO_3$; Molecular Mass: 255.27 g/mol; $^1$H-NMR [ppm] (CDCl$_3$): 2.43 (s,3,Ph—$CH_3$); 3.85 (s,2,—$CH_2$—C=O); 3.97 (s,3,N—$CH_3$); 6.71 (s,1,=CH—); 7.25–7.72 (AB, 4,ar.); IR [cm$^{-1}$] (KBr): 1740 C=O; 1630 C=C.

EXAMPLE 2

6-Methyl-5-(p-Chlorobenzoyl)-1,3,6-Trihydro-6-Aza-3-Oxapentalen-2-One (A) Ethyl 5-(p-chlorobenzoyl)-1-methylpyrrole-2-acetate To a solution of (22.0 g. (0.131 mole) of ethyl N-methylpyrrole-2-acetate and 24.5 g. (0.14 mole) of p-chlorobenzoyl chloride in 120 ml. of carbon disulfide is added 35.0 g. (0.262 mole) of anhydrous aluminum chloride over a period of 20 minutes with intermittant cooling to keep the temperature at 25° C. The mixture is stirred for an additional 20 minutes. The carbon disulfide solvent is then decanted and discarded. The red gummy residue is washed with hexane and dilute hydrochloric acid and ice is added to the mixture. The mixture is extracted with ether. The ether solution is shaken with an aqueous solution of dimethylaminopropylamine and washed with dilute hydrochloric acid followed by brine. The solution is dried over magnesium sulfate and treated with charcoal. After removal of the charcoal, the solvent is evaporated in vacuo leaving a partially crystalline red oil as a residue. This material is extracted with three 500 ml. portions of boiling pentane. The combined pentane extracts are evaporated in vacuo, and the residue is crystallized from 60 ml. of cold methanol. The resulting solid is collected and washed with cold methanol; there is obtained about 6.3 g of a white crystalline solid, ethyl 5-(p-chlorobenzoyl)-1-methylpyrrole-2-acetate, m.p. 74–76° C. Recrystallization from methyl cyclohexane raises the melting point to 78–80° C.

(B) 5-(p-Chlorobenzoyl)-1-methylpyrrole-2-acetic acid

A suspension of 3.06 g. (0.01 mole) of ethyl-5-(p-chlorobenzoyl)-1-methylpyrrole-2-acetate in 25 ml. of 0.5 N sodium hydroxide is refluxed for 30 minutes. About two-thirds of this solution is cooled, washed with ether, and then acidified with dilute hydrochloric acid. The resulting solid precipitate is collected by filtration, dried and recrystallized from ethanol-water to give the product, 5-(p-chlorobenzoyl)-1-metylpyrrole-2-acetic acid; m.p. 189–191° C. Upon recrystallization from ethanol-water, the melting point is 188–190° C. Analysis: Calcd. for $C_{14}H_{12}ClNO_3$: C, 60.54; H, 4.36; N, 5.05%. Found: C, 60.54; H, 4.37; N, 5.14%.

(C) 6-Methyl-5-(p-chlorobenzoyl)-1,3,6-trihydro-6-aza-3-oxapentalen-2-one 5-(p-Chlorobenzoyl)-1-methylpyrrole-2-acetic acid is subjected to the procedure of Example 1, part C to produce 6-methyl-5-(p-chlorobenzoyl)-1,3,6-trihydro-6-aza-3-oxapentalen-2-one ($R_1$=H, $R_2$=H, $R_3$=p-chlorophenyl, $R_4$=$CH_3$, $R_5$=H, Y=CO, m=1, n=0).

EXAMPLE 3

6-Methyl-5-(3'4'-Dibromobenzoyl)-1,3,6-Trihydro-6-Aza-3-Oxapentalen-2-One (A) Ethyl 5-(3'4'-dibromobenzoyl)-1-methyl-pyrrole-2-acetate and 5-benzoyl-1-methyl-pyrrole-2-acetic acid By following the procedure of Example 2, part A, except that an equivalent quantity of 3'4'dibromobenzoyl chloride is employed in place of the p-chlorobenzoylchloride used in Example 2, ethyl 5-(3'4'-dibromobenzoyl)-1-methyl-pyrrole-2-acetate is produced; and 5-(3'4'-dibromobenzoyl)-1-methyl-pyrrole-2-acetic acid is produced when the procedure of Example 2, part B is employed.

(B) 6-Methyl-5-(3'4'-dibromobenzoyl)-1,3,6-trihydro-6-aza-3-oxapentalen-2-one 5-(3',4')-Dibromobenzoyl-1-methyl-pyrrole-2-acetic acid is subjected to the procedure of Example 1, part C to produce 6-methyl-5-(3'4'-dibromobenzoyl)-1,3,6-trihydro-6-aza-3-oxapentalen-2-one ($R_1$=H, $R_2$=H, $R_3$=3'4'-dibromobenzoyl, $R_4$=$CH_3$, $R_5$=H, Y=CO, m=1, n=0).

EXAMPLE 4

6-Methyl-5-Benzoyl-1,3,6-Trihydro-6-Aza-3-Oxapentalen-2-One (A) 5-Benzoyl-1-methylpyrrole-2-acetonitrile To a chilled suspension of 9.7 g. (0.07 mole) of aluminum chloride in 45 ml. methylene chloride is added 9 ml. (0.07 mole) benzoyl chloride. The resulting solution is added dropwise to a solution of 1-methylpyrrole-2-acetonitrile in 30 ml. methylene chloride while cooling externally with an ammonium chloride ice bath (temperature below 5° C.). After the addition is complete, the reaction mixture is stirred at 0° C. for fifteen minutes and then poured into ice acidified with 3N hydrochloric acid. The acidic fraction is extracted three times with methylene chloride. The organic fractions are combined and washed consecutively with N,N-dimethyl-1,3-propanediamine and 3N hydrochloric acid. The organic solution is dried over anhydrous magnesium sulfate. The solvent is then evaporated off to yield an oily residue which is column chromatographed on neutral alumina using hexane, benzene and ethylacetate as successive solvents. The first few fractions having ultraviolet absorption in the 240–260 mμ range contain the desired product. These fractions are combined, the solvent evaporated off, and the oily residue, when triturated with methanol, yields the crystalline product, 5-benzoyl-1-methylpyrrole-2-acetonitrile, m.p. 106–108° C.

(B) 5-Benzoyl-1-methylpyrrole-2-acetic acid:

A suspension of 2.42 g. (0.11 mole) of 5-benzoyl-1-methylpyrrole-2-acetonitrile, 0.9 g. (0.22 mole) sodium hydroxide, 6 ml. water, and 0.5 ml. ethanol, is stirred and refluxed for one hour. The resulting solution is cooled and extracted in water and chloroform. The aqueous fraction is made acidic with 3N hydrochloric acid. A white solid, 5-benzoyl-1-methylpyrrole-2-acetic acid, precipitates which is filtered and washed with a hexane-ether solution, m.p. 144–145° C. Analysis: Calcd. for $C_{14}H_{13}NO_3$: C, 69.12; H, 5.39; N, 5.76% Found: C, 69.23; H, 5.47; N, 5.78%.

(C) 6-Methyl-5-benzoyl-1,3,6-trihydro-6-aza-3-oxapentalen-2-one

5-Benzoyl-1-methylpyrrole-2-acetic acid is subjected to the procedure of Example 1, part C to produce 6-methyl-5-benzoyl-1,3,6-trihydro-6-aza-3-oxapentalen-2-one ($R_1$=H, $R_2$=H, $R_3$=phenyl, $R_4$=$CH_3$, $R_5$=H, Y=CO, m=1, n=0).

EXAMPLE 5

6-Methyl-5-(m-Chlorobenzoyl)-1,3,6-Trihydro-6-Aza-3-Oxapentalen-2-One (A) 5-(m-Chlorobenzoyl)-1-methylpyrrole-2-acetonitrile To a cooled suspension of 16.6 g. (0.12 mole) aluminum chloride in 60 ml. 1,2-dichloroethane is added dropwise 23 g. (0.12 mole) m-chlorobenzoylchloride. The resulting suspension is added dropwise to a cooled solution of 15 g. (0.12 mole) 1-methylpyrrole-2-acetonitrile in 60 ml. 1,2-dichloroethane. The reaction mixture is stirred for about twenty minutes at room temperature and then heated and refluxed for three minutes. The reaction is terminated by pouring the mixture into ice acidified with 3N hydrochloric acid. The resulting two fractions are separated. The aqueous fraction is washed with chloroform. The organic fractions are combined and washed consecutively with N,N-dimethyl-1,3-propanediamine, 3N hydrochloric acid and saturated sodium chloride solution. The organic fraction is then dried over anhydrous magnesium sulfate. The solvent is evaporated, and the resulting residue is triturated with cold methanol to yield a precipitate of the desired product which is filtered off and set aside. The methanol filtrate is concentrated in vacuo, and the remaining oily residue is chromatographed on a column packed with neutral alumina using hexane, benzene and ether as the successive solvents. The desired product is isolated by evaporation of the first few compound-bearing (ether) fractions. The solids are combined and recrystallized from methanol to yield 5-(m-chlorobenzoyl)-1-methylpyrrole-2-acetonitrile, m.p. 122–127° C. Analysis: Calcd. for $C_{14}H_{11}ClN_2O$: N, 10.83%. Found: N, 10.52

(B) 5-(m-Chlorobenzoyl)-1-methylpyrrole-2-acetic acid

A mixture of 2.8 g. (0.01 mole) of 5-(m-chlorobenzoyl)-1-methylpyrrole-2-acetonitrile, 22 ml. of 1N sodium hydroxide solution and 5 ml. ethanol is stirred at reflux for 15 hours. Some of the ethanol is evaporated. The remaining solution is poured into ice acidified with dilute hydrochloric acid. A white solid, 5-(m-chlorobenzoyl)-1-methylpyrrole-2-acetic acid, precipitates which is recrystallized twice from methanol: water, m.p. 165° C. Analysis: Calcd. for $C_{14}H_{12}ClNO_3$: C, 60.54; H, 4.36; N, 5.05%. Found: C, 60.61; H, 4.40;N, 4.87%.

(C) 6-Methyl-5-(m-chlorobenzoyl)-1,3,6-trihydro-6-aza-3-oxapentalen-2-one 5-(m-Chlorobenzoyl)-1-methylpyrrole-2-acetic acid is subjected to the procedure of Example 1, part C to produce 6-Methyl-5-(m-chlorobenzoyl)-1,3,6-trihydro-6-aza-3-oxapentalen-2-one ($R_1$=H, $R_2$=H, $R_3$=m-chlorophenyl, $R_4$=$CH_3$, $R_5$=H, Y=CO, m=1, n=0).

EXAMPLE 6

6-Methyl-5-(p-Bromobenzoyl)-1,3,6-Trihydro-6-Aza-3-Oxapentalen-2-One (A) 5-(p-bromobenzoyl)-1-methylpyrrole-2-acetonitrile The procedure of Example 5 is repeated except that an equivalent quantity of p-bromobenzoyl chloride is used in place of the m-chlorobenzoyl chloride used therein to yield, 5-(p-bromobenzoyl)-1-methylpyrrole-2-acetontrile, m.p. 139–141 ° C.

(B) 5-(p-Bromobenzoyl)-1-methylpyrrole-2-acetic acid

By following the procedure of Example 5B, using an equivalent quantity of the nitrile from part A in place of the 5-(m-chlorobenzoyl)-1-methylpyrrole-2-acetonitrile used therein 5-(p-bromobenzoyl)-1-methylpyrrole-2-acetic acid, m.p. 188° C. is obtained.

(C) 6-Methyl-5-(p-bromobenzoyl)-1,3,6-trihydro-6-aza-3-oxapentalen-2-one 5-(p-Bromobenzoyl)-1-methylpyrrole-2-acetic acid is subjected to the procedure of Example 1, part C to produce 6-methyl-5-(p-bromobenzoyl)-1,3,6-trihydro-6-aza-3-oxapentalen-2-one ($R_1$=H, $R_2$=H, $R_3$=p-bromophenyl, $R_4$=$CH_3$, $R_5$=H, Y=CO, m=1, n=0).

EXAMPLE 7

6-Methyl-5-(p-Fluorobenzoyl)-1,3,6-Trihydro-6-Aza-3-Oxapentalen-2-One (A) S-(p-Fluorobenzoyl)-1-methylpyrrole-2-acetonitrile The procedure of Example 5A is repeated except that an equivalent quantity of p-fluorobenzoyl chloride is used in place of the m-chlorobenzoyl chloride used therein to yield 5-(p-fluorobenzoyl)-1-methylpyrrole-2-acetonitrile, m.p. 134–136° C.

(B) 5-(p-Fluorobenzoyl)-1-methylpyrrole-2-acetic acid

By following the procedure of Example 5B, using an equivalent quantity of the nitrile from part A in place of the 5-(m-chlorobenzoyl)-1-methylpyrrole-2-acetonitrile used therein, 5-(p-fluorobenzoyl)-1-methylpyrrole-2-acetic acid, m.p. 164–165° C. is obtained.

(C) 6-Methyl-5-(p-fluorobenzoyl)-1,3,6-trihydro-6-aza-3-oxapentalen-2-one 5-(p-Fluorobenzoyl)-1-methylpyrrole-2-acetic acid is subjected to the procedure of Example 1, part C to produce 6-methyl-5-(p-fluorobenzoyl)-1,3,6-trihydro-6-aza-3-oxapentalen-2-one ($R_1$=H, $R_2$=H, $R_3$=p-fluorophenyl, $R_4$=$CH_3$, $R_5$=H, Y=CO, m=1, n=0).

EXAMPLE 8

6-Methyl-5-(o-Chlorobenzoyl)-1,3,6-Trihydro-6-Aza-3-Oxapentalen-2-One (A) 5-(o-Chlorobenzoyl)-1-methylpyrrole-2-acetonitrile To a cooled suspension of 14 g. (0.105 mole) aluminum chloride in 45 ml. dichloroethane is added dropwise, 18.5 g. (0.1 05 mole) o-chlorobenzoyl chloride. The resulting solution is added dropwise to a cooled (0° C.) solution of 1-methylpyrrole-2-acetonitrile in 45 ml. dichloroethane keeping the temperature at approximately 10° C. The mixture is stirred at room temperature for about twenty minutes, and then refluxed for three minutes. It is poured into ice acidified with 3N hydrochloric acid, and the resulting two layers are separated. The aqueous fraction is extracted twice with chloroform. The organic fractions are combined and washed twice with N,N-dimethyl-1,3-propanediamine, once with 3N hydrochloric acid and once with saturated sodium chloride solution. The organic fraction is dried over anhydrous magnesium sulfate. The solvent is evaporated, and the resulting oil is chromatographed on a column packed with neutral alumina using benzene and ether as successive solvents. The first compound-bearing fractions contain the desired product. The solvent is evaporated and the resulting oil crystallizes upon treatment with methanol. The solid product, 5-(o-chlorobenzoyl)-1-methylpyrrole-2-acetonitrile, is purified by recrystallization from benzene:cyclohexane solution, m.p. 80–85° C.

(B) 5-(o-Chlorobenzoyl)-1-methylpyrrole-2-acetic acid

A solution of 2.4 g. (0.009 mole) of 5-(o-chlorobenzoyl)-1-methylpyrrole-2-acetonitrile, 18 ml. of 1N sodium hydroxide and 18 ml. 95% ethanol is stirred and refluxed for seven hours. The ethanol is evaporated off, and the remaining solid residue is dissolved in water and washed with chloroform. The aqueous layer is made acidic with 3N hydrochloric acid. An oil precipitates which crystallizes when scratched. The solid is filtered and washed with water and hexane. The solid is purified by recrystallization from methanol:water and again from ether:hexane, m.p. 140–141° C. Analysis: Calcd. for $C_{14} H_{12} ClNO_{31}$: C, 60.54; H, 4.36; N, 5.05%. Found: C, 60.55; H, 4.43; N, 4.91%.

(C) 6-Methyl-5-(o-chlorobenzoyl)-1,3,6-trihydro-6-aza-3-oxapentalen-2-one 5-(o-Chlorobenzoyl)-1-methylpyrrole-2-acetic acid is subjected to the procedure of Example 1, part C to produce 6-Methyl-5-(o-chlorobenzoyl)-1,3,6-trihydro-6-aza-3-oxapentalen-2-one ($R_1$=H, $R_2$=H, $R_3$=o-chlorophenyl, $R_4$=$CH_3$, $R_5$=H, Y=CO, m=1, n=0).

EXAMPLE 9

6-Methyl-5-(2',4'-Dichlorobenzoyl)-1,3,6-Trihydro-6-Aza-3-Oxapentalen-2-One (A) 5-(2',4'-Dichlorobenzoyl)-1-methylpyrrole-2-acetonitrile To a suspension of 16.6 g. (0.125 mole) of aluminum chloride in 60 ml. 1,2-dichloroethane is added 26.2 g. (0.125 mole) of 2,4-dichlorobenzoyl chloride. The resulting solution is added slowly to a solution of 15 g. (0.125 mole) of 1-methylpyrrole-2-acetonitrile in 60 ml. 1,2-dichloroethane while cooling externally with an ice bath. After the addition is complete, the mixture is stirred for 40 minutes at room temperature followed by heating at reflux for 3 minutes. It is then poured into ice acidified with dilute hydrochloric acid. The organic phase is separated and washed successively with N,N-dimethyl-1,3-propanediamine, 3N hydrochloric acid, and saturated sodium chloride solution. It is then dried over magnesium sulfate and the solvent evaporated. The resulting red oily residue is chromatographed on a column packed with neutral alumina and eluted with benzene and ether. The first compound-bearing fractions upon evaporation yield a white solid, 5-(2',4'-dichlorobenzoyl)-1-methylpyrrole-2-acetonitrile, which is purified by recrystallization from methanol, m.p. 129–130° C. Analysis: Calcd. for $C_{14} H_{10} Cl_2 N_2 O$: N, 9.56%. Found: N, 9.51%.

(B) 5-(2',4'-Dichlorobenzoyl)-1-methylpyrrole-2-acetic acid

A solution of 4.3 g. (0.015 mole) of 5-(2',4'-dichlorobenzoyl)-1-methylpyrrole-2-acetonitrile in 30 ml. 1N sodium hydroxide and 30 ml. 95% ethanol is refluxed overnight. The solution is concentrated and poured into dilute hydrochloric acid. A white solid, 5-(2',4'-dichlorobenzoyl)-1-methylpyrrole-2-acetic acid precipitates which is recrystallized from isopropanol and methanol, m.p. 165–166° C. Analysis: Calcd. for $C_{14} H_{11} Cl_2 NO_3$: C, 53.86; H, 3.55; N, 4.68%. Found: C, 53.97; H, 3.66; N, 4.69%.

(C) 6-Methyl-5-(2',4'-dichlorobenzoyl)-1,3,6-trihydro-6-aza-3-oxapentalen-2-one 5-(2',4'-Dichlorobenzoyl)-1-methylpyrrole-2-acetic acid is subjected to the procedure of Example 1, part C to produce 6-methyl-5-(2',4'-dichlorobenzoyl)-1,3,6-trihydro-6-aza-3-oxapentalen-2-one ($R_1$=H, $R_2$=H, $R_3$=2',4'-dichlorophenyl, $R_4$=$CH_3$, $R_5$=H, Y=CO, m=1, n=0).

EXAMPLE 10

6-Methyl-5-(o-Toluoyl)-1,3,6-Trihydro-6-Aza-3-Oxapentalen-2-One

6-Methyl-5-(m-Toluoyl)-1,3,6-Trihydro-6-Aza-3-Oxapentalen-2-One

6-Methyl-5-(p-Ethylbenzoyl)-1,3,6-Trihydro-6-Aza-3-Oxapentalen-2-One

6-Methyl-5-(3',4'-Dimethylbenzoyl)-1,3,6-Trihydro-6-Aza-3-Oxapentalen-2-One (A) By repeating the procedure of Example 8A, except that an equivalent quantity of o-toluoyl chloride, m-toluoyl chloride, p-ethylbenzoyl chloride and 3,4-dimethylbenzoyl chloride is used in lieu of the 2,4-dichlorobenzoyl chloride used therein, there are obtained as respective products the corresponding 5-(o-toluoyl), 5-(m-toluoyl), 5-(p-ethylbenzoyl) and 5-(3',4'-dimethylbenzoyl) derivatives of 1-methylpyrrole-2-acetonitrile.

(B) The procedure of Example 8B is repeated, using an equivalent quantity of each of the foregoing nitriles in place of the 5-(2',4'-dichlorobenzoyl)-1-methylpyrrole-2-acetonitrile used therein, to yield the products identified above, which are the corresponding 5-(o-toluoyl), 5-(m-toluoyl), 5-(p-ethylbenzoyl) and 5-(3',4'-dimethylbenzoyl) derivatives of 1-methylpyrrole-2-acetic acid.

(C) The 5-(o-toluoyl), 5-(m-toluoyl), 5-(p-ethylbenzoyl) and 5-(3',4'-dimethylbenzoyl) derivatives of 1-methylpyrrole-2-acetic acid from part B are each separately subjected to the procedure of Example 1, part C to produce 6-methyl-5-(o-toluoyl)-1,3,6-trihydro-6-aza-3-oxapentalen-2-one, 6-methyl-5-(m-toluoyl)-1,3,6-trihydro-6-aza-3-oxapentalen-2-one, 6-methyl-5-(p-ethylbenzoyl)-1,3,6-trihydro-6-aza-3-oxapentalen-2-one, and 6-methyl-5-(3,4-dimethylbenzoyl)-1,3,6-trihydro-6-aza-3-oxapentalen-2-one, respectively.

EXAMPLE 11

6-Methyl-5-(p-Anisoyl)-1,3,6-Trihydro-6-Aza-3-Oxapentalen-2-One (A) Methyl 5-(p-anisoyl)-1-methylpyrrole-2-acetate A solution of 17.0 g. (0.1 mole) of p-anisoyl chloride and 13.3 g. (0.1 mole) of aluminum chloride in 200 ml. of methylene chloride is added over 5 minutes to a solution of methyl 1-methylpyrrole-2-acetate in 100 ml. of methylene chloride at ice bath temperature. The mixture is stirred for 25 minutes and poured into ice acidified with dilute hydrochloric acid. The organic layer is separated and the aqueous layer is washed with methylene chloride. The combined organic solutions are washed successively with dimethylaminopropylamine solution, dilute hydrochloric acid and brine and then dried over anhydrous magnesium sulfate. The solvent is evaporated in vacuo to give a dark oily residue which is crystallized from 40 ml. of cold methanol. The solid is collected by filtration, washed with cold methanol and recrystallized from methanol to give white crystalline methyl 5-(p-anisoyl)-1-methylpyrrole-2-acetate, m.p. 104–105° C.

(B) 5-(p-Anisoyl)-1-methylpyrrole-2-acetic acid

A solution of 3.00 g. (0.0105 mole) of methyl 5-(p-anisoyl)-1-methylpyrrole-2-acetate in 12 ml. (0.012 mole) of 1N sodium hydroxide solution and 5 ml. of 95% ethanol is refluxed for 30 minutes. The solution is diluted with water, and the ethanol is evaporated in vacuo. The solution is filtered, and the filtrate acidified with dilute hydrochloric acid. The precipitated solid is collected by filtration, dried and recrystallized from methanol-water to give white 5-(p-anisoyl)-1-methylpyrrole-2-acetic acid, m.p. 170–171° C. Analysis: Calcd. for $C_{15}H_{15}NO_4$: C, 65.92; H, 5.53; N, 5.13%. Found: C, 66.01; H, 5.62; N, 5.12%

(C) 6-Methyl-5-(p-anisoyl)-1,3,6-trihydro-6-aza-3-oxapentalen-2-one 5-(p-Anisoyl)-1-methylpyrrole-2-acetic acid is subjected to the procedure of Example 1, part C to produce 6-methyl-5-(p-anisoyl)-1,3,6-trihydro-6-aza-3-oxapentalen-2-one ($R_1$=H, $R_2$=H, $R_3$=4'-methoxyphenyl, $R_4$=$CH_3$, $R_5$=H, Y=CO, m=1, n=0).

EXAMPLE 12

6-Methyl-5-(m-Anisoyl)-1,3,6-Trihydro-6-Aza-3-Oxapentalen-2-One

6-Methyl-5-(p-Ethoxybenzoyl)-1,3,6-Trihydro-6-Aza-3-Oxapentalen-2-One

By repeating the procedures of Examples 11A and 11B successively, except that an equivalent quantity each of m-anisoyl chloride and p-ethoxybenzoyl chloride is initially employed in place of p-anisoyl chloride, there are obtained as ester products, the corresponding 5-(m-anisoyl) and 5-(p-ethoxybenzoyl) derivatives of methyl 1-methylpyrrole-2-acetate, and as acid products, the above-captioned corresponding 5-(m-anisoyl) and 5-(p-ethoxybenzoyl) derivatives of 1-methylpyrrole-2-acetic acid, respectively. The acids are converted to the corresponding lactones following the procedure of Example 1, part C ($R_1$=H, $R_2$=H, $R_3$=3'-methoxyphenyl or 4'-ethoxyphenyl, $R_4$=$CH_3$, $R_5$=H, Y=CO, m=1, n=0).

EXAMPLE 13

6-Methyl-5-(3'-Chloro-4'-Toluoyl)-1,3,6-Trihydro-6-Aza-3-Oxapentalen-2-One (A) 5-(3'Chloro-p-toluoyl)-1-methylpyrrole-2-acetonitrile 21.4 grams (0.114 mole) of 3-chloro-4-methylbenzoylchloride is added to a suspension of 15.2 g. (0.114 mole) aluminum chloride in 50 ml. 1,2-dichloroethane. The resulting solution is added dropwise to a chilled solution of 13.7 g. (0.114 mole) of 1-methylpyrrole-2-acetonitrile in 50 ml. 1,2-dichloroethane. After the addition is complete, the mixture is stirred for ten minutes at room temperature, and then heated to reflux for three minutes. It is poured into ice acidified with dilute HCl. The organic phase is separated and washed consecutively with N,N-dimethyl-1,3-propanediamine, 3N hydrochloric acid and saturated sodium chloride solution. It is then dried over anhydrous magnesium sulfate, and the solvent evaporated off. A white solid, 5-(3'-chloro-p-toluoyl)-1-methylpyrrole-2-acetonitrile, precipitates from the resulting oily residue upon trituration with methanol which is purified by recrystallization from methanol, m.p. 116–118° C. Analysis: Calcd. for $C_{15}H_{13}ClN_2O$: N, 10.26%. Found: N, 10.38%.

(B) 5-(3'-Chloro-p-toluoyl)-1-methylpyrrole-2-acetic acid

A solution of 3.5 g. (0.0013 mole) of 5-(3'-chloro-p-toluoyl)-1-methylpyrrole-2-acetonitrile in 18 ml. 95% ethanol and 26 ml. 1N sodium hydroxide is heated at reflux overnight. The reaction mixture is then cooled and poured into dilute hydrochloric acid. The resulting white precipitate, 5-(3'-chloro-p-toluoyl)-1-methylpyrrole-2-acetic acid, is filtered off and purified by recrystallization once from isopropanol, m.p. 176–178° C.

(C) 6-Methyl-5-(3'-chloro-4'-toluoyl)-1,3,6-trihydro-6-aza-3-oxapentalen-2-one 5-(3'-Chloro-p-toluoyl)-1-methylpyrrole-2-acetic acid is subjected to the procedure of Example 1, part C to produce 6-methyl-5-(3'-chloro-4'-toluoyl)-1,3,6-trihydro-6-aza-3-oxapentalen-2-one ($R_1$=H, $R_2$=H, $R_3$=3'-chloro-4'-methylphenyl, $R_4$=$CH_3$, $R_5$=H, Y=CO, m=1, n=0).

EXAMPLE 14

6-Methyl-5-(3',4'-Dimethoxybenzoyl)-1,3,6-Trihydro-6-Aza-3-Oxapentalen-2-One (A) Methyl 5-(3',4'-dimethoxybenzoyl)-1-methylpyrrole-2-acetate By repeating the Friedel-Crafts procedures of Example 11 with an equivalent amount of an appropriately substituted benzoyl chloride, methyl 5-(3',4'-dimethoxybenzoyl)-1-methylpyrrole-2-acetate is obtained.

(B) The transformation of the acetic acid ester of part (A) to its acetic acid is performed according to example 11 part B to yield 5-(3', 4'-dimethoxybenzoyl)-1-methylpyrrole-2-acetic acid (D) 6-Methyl-5-(3',4'-dimethoxybenzoyl)-1,3,6-trihydro-6-aza-3-oxapentalen-2-one The acid from part B above is subjected to the procedure of Example 1, part C to produce 6-methyl-5-(3',4'-dimethoxybenzoyl)-1,3,6-trihydro-6-aza-3-oxapentalen-2-one ($R_1$=H, $R_2$=H, $R_3$=3',4'-dimethoxyphenyl, $R_4$=$CH_3$, $R_5$=H, Y=CO, m=1, n=0).

EXAMPLE 15

6-Methyl-5-(3',5'-Dinitrobenzoyl)-1,3,6-Trihydro-6-Aza-3-Oxapentalen-2-One (A) Methyl 5-(3',5'-dinitrobenzoyl)-1-methylpyrrole-2-acetate By repeating the Friedel-Crafts procedures of Example 11 with an equivalent amount of an appropriately substituted benzoyl chloride, methyl 5-(3',5'-dinitrobenzoyl)-1-methylpyrrole-2-acetate.

(B) 5-(3',5'-dinitrobenzoyl)-1-methylpyrrole-2-acetic acid

The transformation of the acetic acid ester of part (A) to its acetic acid is performed according to the hydrolysis procedure of Example 11 B is repeated with an equivalent amount of the pyrrole acetate obtained in part (A) to yield 5-(3',5'-dinitrobenzoyl)-1-methylpyrrole-2-acetic acid.

(C) 6-Methyl-5-(3',5'-dinitrobenzoyl)-1,3,6-trihydro-6-aza-3-oxapentalen-2-one 5-(3',5'-dinitrobenzoyl)-1-methylpyrrole-2-acetic acid is subjected to the procedure of Example 1, part C to produce 6-methyl-5-(3',5'-dinitrobenzoyl)-1,3,6-trihydro-6-aza-3-oxapentalen-2-one ($R_1$=H, $R_2$=H, $R_3$=3',5'-dinitrophenyl, $R_4$=$CH_3$, $R_5$=H, Y=CO, m=1, n=0).

EXAMPLE 16

6-Methyl-5-(3'-Bromo-4'-Chlorobenzoyl)-1,3,6-Trihydro-6-Aza-3-Oxapentalen-2-One (A) Methyl 5-(3'-bromo-4'-chlorobenzoyl)-1-methylpyrrole-2-acetate By repeating the Friedel-Crafts procedures of Example 11 with an equivalent amount of an appropriately substituted benzoyl chloride, methyl 5-(3'-bromo-4'-chlorobenzoyl)-1-methylpyrrole-2-acetate is obtained.

(B) 5-(3'-bromo-4'-chlorobenzoyl)-1-methylpyrrole-2-acetic acid

The transformation of the acetic acid ester of part (A) to its acetic acid is performed according to the hydrolysis procedure of Example 11B is repeated with an equivalent amount of the pyrrole acetate obtained in part (A) to yield 5-(3'-bromo-4'-chlorobenzoyl)-1-methylpyrrole-2-acetic acid.

(C) 6-Methyl-5-(3'-Bromo-4'-chlorobenzoyl)-1,3,6-trihydro-6-aza-3-oxapentalen-2-one 5-(3'-bromo-4'-chlorobenzoyl)-1-methylpyrrole-2-acetic acid is subjected to the procedure of Example 1, part C to produce 6-methyl-5-(3'-Bromo-4'-chlorobenzoyl)-1,3,6-trihydro-6-aza-3-oxapentalen-2-one ($R_1$=H, $R_2$=H, $R_3$=3'-bromo-4'-chlorophenyl, $R_4$=$CH_3$, $R_5$=H, Y=CO, m=1, n=0).

EXAMPLE 17

6-Methyl-5-(2',3',5'-Tribromobenzoyl)-1,3,6-Trihydro-6-Aza-3-Oxapentalen-2-One (A) Methyl 5-(2',3',5'-tribromobenzoyl)-1-methylpyrrole-2-acetate By repeating the Friedel-Crafts procedures of Example 11 with an equivalent amount of an appropriately substituted benzoyl chloride, methyl 5-(2',3',5'-tribromobenzoyl)-1-methylpyrrole-2-acetate is obtained.

(B) 5-(2',3',5'-tribromobenzoyl)-1-methylpyrrole-2-acetic acid

The transformation of the acetic acid ester of part (A) to its acetic acid is performed according to the hydrolysis procedure of Example 11B is repeated with an equivalent amount of the pyrrole acetate obtained in part (A) to yield 5-(2',3',5'-tribromobenzoyl)-1-methylpyrrole-2-acctic acid.

(C) 6-Methyl-5-(2',3',5'-tribromobenzoyl)-1,3,6-trihydro-6-aza-3-oxapentalen-2-one 5-(2',3',5'-tribromobenzoyl)-1-methylpyrrole-2-acetic acid is subjected to the procedure of Example 1, part C to produce 6-methyl-5-(2',3',5'-tribromobenzoyl)-1,3,6-trihydro-6-aza-3-oxapentalen-2-one ($R_1$=H, $R_2$=H, $R_3$=2',3',5'-tribromophenyl, $R_4$=$CH_3$, $R_5$=H, Y=CO, m=1, n=0).

EXAMPLE 18

6-Methyl-5-(3',4',5'-Trimethoxybenzoyl)-1,3,6-Trihydro-6-Aza-3-Oxapentalen-2-One (A) Methyl 5-(3',4',5'-trimethoxybenzoyl)-1-methylpyrrole-2-acetate By repeating the Friedel-Crafts procedures of Example 11 with an equivalent amount of an appropriately substituted benzoyl chloride, methyl 5-(3',4',5'-trimethoxybenzoyl)-1-methylpyrrole-2-acetate is obtained.

(B) 5-(3',4',5'-trimethoxybenzoyl)-1-methylpyrrole-2-acetic acid

The transformation of the acetic acid ester of part (A) to its acetic acid is performed according to the hydrolysis procedure of Example 11B is repeated with an equivalent amount of the pyrrole acetate obtained in part (A) to yield 5-(3',4',5'-trimethoxybenzoyl)-1-methylpyrrole-2-acetic acid.

(C) 6-Methyl-5-(3',4',5'-trimethoxybenzoyl)-1,3,6-trihydro-6-aza-3-oxapentalen-2-one 5-(3',4',5'-trimethoxybenzoyl)-1-methylpyrrole-2-acetic acid is subjected to the procedure of Example 1, part C to produce 6-methyl-5-(3',4',5'-trimethoxybenzoyl)-1,3,6-trihydro-6-aza-3-oxapentalen-2-one ($R_1$=H, $R_2$=H, $R_3$=3',4',5'-trimethoxyphenyl, $R_4$=$CH_3$, $R_5$=H, Y=CO, m=1, n=0).

EXAMPLE 19

6-Methyl-5-(p-Acetaminobenzoyl)-1,3,6-Trihydro-6-Aza-3-Oxapentalen-2-One (A) 5-(p-Nitrobenzoyl)-1-methylpyrrole-2-acetonitrile A solution of 46.4 g. (0.25 mole) of p-nitrobenzoyl chloride in 100 ml. 1,2-dichloroethane is added portionwise to a suspension of 32.2 g. (0.25 mole) aluminum cloride in 100 ml. 1,2-dichloroethane. This mixture is added dropwise to a chilled solution of 30.0 g. (0.25 mole) 1-methylpyrrole-2-acetonitrile in 100 ml. 1,2-dichloroethane. After the addition is complete, the mixture is stirred for twenty minutes at room temperature and then refluxed for four minutes. It is poured into ice acidified with 2N hydrochloric acid. The organic phase is separated and washed successively with N,N-dimethyl-1,3-propanediamine, 3N hydrochloric acid and saturated sodium chloride solution. It is then dried over magnesium sulfate and the solvent evaporated in vacuo. The resulting semi-solid residue is triturated with cold methanol from which the product, 5-(p-nitrobenzoyl)-1-methylpyrrole-2-acetonitrile, crystallizes. It is removed by filtration and purified by recrystallization from acetone, m.p. 167–169° C.

(B) 5-(p-Aminobenzoyl)-1-methylpyrrole-2-acetonitrile

A solution of 7 g. (0.026 mole) of 5-(p-nitrobenzoyl)-1-methylpyrrole-2-acetonitrile in 450 ml. of ethyl acetate containing 1 g. palladium-on-carbon catalyst is hydrogenated in a Parr shaker under 44 p.s.i. of hydrogen until the theoretical amount of hydrogen is consumed. The catalyst is filtered off, and the solvent evaporated in vacuo. A yellow solid, 5-(p-aminobenzoyl)-1-methylpyrrole-2-acetonitrile remains, m.p. 137–142° C.

(C) 5-(p-Acetaminobenzoyl)-1-methylpyrrole-2-acetic acid

A suspension of 6.0 g. (0.025 mole) of 5-(p-aminobenzoyl)-1-methylpyrrole-2-acetonitrile, 25 ml. 95% ethanol and 25 ml. /N sodium hydroxide is refluxed overnight. The ethanol is then evaporated in vacuo, and the remaining suspension is poured into ice acidified with dilute hydrochloric acid to pH 5. The resulting solid is partitioned between sodium bicarbonate solution and chloroform. The insoluble substances are filtered from the two-phase mixture. The sodium bicarbonate layer is separated and acidified slowly with dilute hydrochloric acid. Solids precipitate at various pHs which are separated by filtration. The desired product, 5-(p-aminobenzoyl)-1-methylpyrrole-2-acetic acid, precipitates at pH 3, m.p. 173–175° C. Acylation with acetic anhydride in pyridine yields the title compound.

(D) 6-Methyl-5-(p-Acetaminobenzoyl)-1,3,6-trihydro-6-aza-3-oxapentalen-2-one 5-(p-Acetaminobenzoyl)-1-methylpyrrole-2-acetic acid is subjected to the procedure of Example 1, part C to produce 6-methyl-5-(p-aminobenzoyl)-1,3,6-trihydro-6-aza-3-oxapentalen-2-one ($R_1$=H, $R_2$=H, $R_3$=p-acetaminophenyl, $R_4$=CH$_3$, $R_5$=H, Y=CO, m=1, n=0).

EXAMPLE 20

6-Methyl-5-(p-Nitrobenzoyl)-1,3,6-Trihydro-6-Aza-3-Oxapentalen-2-One (A) Ethyl 5-(p-Nitrobenzyl)-1-methylpyrrole-2-acetate A solution of 5.5 g. (0.03 mole) of p-nitrobenzoyl chloride in 60 ml. methylene chloride is added to a suspension of 3.9 g. (0.03 mole) aluminum chloride in 20 ml. methylene chloride. The resulting suspension is added dropwise to a chilled (−15° C.) solution of ethyl 1-methylpyrrole-2-acetate in 50 ml. methylene chloride. The solution is stirred for 15 minutes at −10° C. and at room temperature for 15 minutes. The reaction mixture is poured into ice-dilute hydrochloric acid. The organic phase is separated and washed successively with N,N-dimethyl-1,3-propanediamine, 3N hydrochloric acid and a saturated solution of sodium chloride, dried over anhydrous magnesium sulfate, and the solvent evaporated in vacuo. A solid, ethyl 5-(p-nitrobenzoyl)-1-methylpyrrole-2-acetate, crystallizes from the remaining oily residue which is isolated by recrystallization from methanol, m.p. 103–106° C.

(B) 5-(p-Nitrobenzoyl)-1-methylpyrrole-2-acetic acid

A solution of 3.2 g. (0.01 mole) of ethyl 5-(p-nitrobenzoyl)-1-methylpyrrole-2-acetate and 25 ml. ethanol is brought to reflux. To this is added dropwise 10 ml. of 1N sodium hydroxide solution. After the addition is complete, the ethanol is evaporated and the residue is acidified with dilute hydrochloric acid. The resulting solid, 5-(p-nitrobenzoyl)-1-methylpyrrole-2-acetic acid, is separated by filtration and purified by recrystallization from ethanol, m.p. 192–195° C.

(C) 6-Methyl-5-(p-nitrobenzoyl)-1,3,6-trihydro-6-aza-3-oxapentalen-2-one 5-(p-Nitrobenzoyl)-1-methylpyrrole-2-acetic acid is subjected to the procedure of Example 1, part C to produce 6-methyl-5-(p-nitrobenzoyl)-1,3,6-trihydro-6-aza-3-oxapentalen-2-one ($R_1$=H, $R_2$=H, $R_3$=p-nitrophenyl, $R_4$=CH$_3$, $R_5$=H, Y=CO, m=1, n=0).

EXAMPLE 21

6-Methyl-5-(p-Cyanobenzoyl)-1,3,6-Trihydro-6-Aza-3-Oxapentalen-2-One (A) Ethyl 5-(p-cyanobenzoyl)-1-methylpyrrole-2-acetate A solution of 5.0 g. (0.03 mole) of p-cyanobenzoyl chloride in 60 ml. of methylene chloride is added to a suspension of 40 g. of aluminum chloride in 30 ml. methylene chloride. The resulting mixture is added dropwise to a chilled solution of 5.0 g. (0.03 mole) of ethyl 1-methylpyrrole-2-acetate in 15 ml. of methylene chloride. The resulting mixture is stirred at room temperature for 20 minutes, and then poured into ice acidified with dilute hydrochloric acid. The organic phase is separated, washed successively with N,N-dimethylaminopropylamine, 3N hydrochloric acid and brine, and dried over anhydrous magnesium sulfate. The solvent is evaporated in vacuo. The resulting solid, which separates from the oily residue on standing, is recrystallized from methanol to give pure ethyl 5-(p-cyanobenzoyl)-1-methylpyrrole-2-acetate, m.p. 117–120° C.

(B) 5-(p-Cyanobenzoyl)-1-methylpyrrole-2-acetic acid

A solution of 0.5 g. (0.0017 mole) of ethyl 5-(p-cyanobenzoyl)-1-methylpyrrole-2-acetate in 3 ml. ethanol is brought to reflux and 1.7 ml. of 1N sodium hydroxide solution is added dropwise. The mixture is refluxed for 3 minutes, and the ethanol is then evaporated in vacuo. The residue is diluted with water and acidified with dilute hydrochloric acid. A white solid precipitates, 5-(p-cyanobenzoyl)-1-methylpyrrole-2-acetic acid, which is collected by filtration and dried, m.p. 196–198° C.

(C) 6-Methyl-5-(p-cyanobenzoyl)-1,3,6-trihydro-6-aza-3-oxapentalen-2-one 5-(p-Cyanobenzoyl)-1-methylpyrrole-2-acetic acid is subjected to the procedure of Example 1, part C to produce 6-methyl-5-(p-cyanobenzoyl)-1,3,6-trihydro-6-aza-3-oxapentalen-2-one ($R_1$=H, $R_2$=H, $R_3$=p-cyanophenyl, $R_4$=CH$_3$, $R_5$=H, Y=CO, m=1, n=0).

EXAMPLE 22

Rac-1,6-Dimethyl-5-(p-Chlorobenzoyl-1,3,6-Trihydro-6-Aza-3-Oxapentalen-2-One (A) Ethyl 5-(p-chlorobenzoyl)-α-methyl-1-methylpyrrole-2-acetate A solution of 6.68 g. (0.0219 mole) of ethyl 5-(p-chlorobenzoyl)-1-methylpyrrole-2-acetate in 50 ml. of ether is added to a solution of 0.94 g. (0.024 mole) of sodamide in about 150 ml. of liquid ammonia at −33° C. The mixture is allowed to reflux for 15 minutes and 3.10 g. (0.0219 mole) of methyl iodide is added. The mixture is stirred for one hour; then the ammonia is allowed to boil off. Ether and enough ammonium chloride to neutralize any anion are added. The mixture is poured into dilute hydrochloric acid and the ether solution is separated and washed with sodium bisulfite solution, sodium bicarbonate solution and brine. It is dried over anhydrous magnesium sulfate and evaporated to give an oily residue which crystallizes upon standing. The solid is recrystallized successively from cyclohexane and methanol to give a white crystalline solid, ethyl 5-(p-chlorobenzoyl)-α-methyl-1-methylpyrrole-2-acetate, m.p. 67–68° C.

(B) 5-(p-Chlorobenzyl)-α-methyl-1-methylpyrrole-2-acetic acid

A solution of 4.05 g. (0.0126 mole) of ethyl 5-(p-chlorobenzoyl)-α-methyl-1-methylpyrrole-2-acetate, 15 ml. of 1N sodium hydroxide solution and 2 ml. of ethanol is refluxed for 30 minutes. The solution is cooled, diluted with water and filtered. The filtrate is acidified with dilute hydrochloric acid. The precipitated solid is collected and recrystallized from methanol-water to give a white crystalline solid, 5-(p-chlorobenzoyl)-α-methyl-1-methylpyrrole-2-acetic acid, m.p. 135–136° C. Analysis: Calcd. for $C_{15}H_{14}ClNO_3$: C, 61.76; H, 4.83; N, 4.82% Found: C, 61.68: H, 4.86; N, 4.89%

(C) 5-(p-Chlorobenzoyl)-α-methyl-1-methylpyrrole-2-acetonitrile

To a suspension of sodium hydride (12.2 g. of 50% w/w NaH in mineral oil) in 1,2-dimethoxyethane is added 5-(p-chlorobenzoyl)-1-methylpyrrole-2-acetonitrile (62.6 g., 0.24 mole) in 1,2-dimethoxyethane over a period of ½ hr. at room temperature. After the addition is complete, the mixture is stirred for 1 hour and then 35 g. (0.25 mole) of methyl iodide is added. The reaction mixture is stirred for an additional 3 hours, concentrated under reduced pressure, diluted with water and extracted with chloroform. After drying, the chloroform is removed leaving a brown solid residue which is triturated with cold methanol to give yellow crystals of 5-(p-chlorobenzoyl)-α-methyl-1-methylpyrrole-2-acetonitrile, m.p. 145–148° C. Two recrystallizations from methanol raises the m.p. to 151.5–152.5° C.

(D) 5-(p-Chlorobenzoyl)-α-methyl-1-methylpyrrole-2-acetic acid 27.1 g. (0.1 mole) sample of 5-(p-chlorobenzoyl)-α-methyl-1-methylpyrrole-2-acetonitrile is hydrolyzed by refluxing for 16 hours with 8 g. (0.2 mole) of sodium hydroxide in 350 ml. of aqueous ethanol. Upon concentration in vacuo, the sodium salt separates which is filtered off and dissolved in water. After acidification with dilute HCl, the corresponding acid, 5-(p-chlorobenzoyl)-α-methyl-1-methylpyrrole-2-acetic acid, precipitates. The original basic filtrates are also acidified, extracted with chloroform and concentrated. The residual solid is combined with the previous solid and recrystallized from methanol-water to give the pure product, 5-(p-chlorobenzoyl)-α-methyl-1-methylpyrrole-2-acetic acid, m.p. 139–141° C.

(E) Rac-1,6-dimethyl-5-(p-chlorobenzoyl)-1,3,6-trihydro-6-aza-3-oxapentalen-2-one 5-(p-Chlorobenzoyl)-α-methyl-1-methylpyrrole-2-acetic acid is subjected to the procedure of Example 1, part C to yield rac-1,6-dimethyl-5-(p-chlorobenzoyl)-1,3,6-trihydro-6-aza-3-oxapentalen-2-one ($R_1$=$CH_3$, $R_2$=H, $R_3$=p-chlorophenyl, $R_4$=$CH_3$, $R_5$=H, Y=CO, m=1, n=0).

EXAMPLE 23

Rac-1-Ethyl-6-Methyl-5-(p-Chlorobenzoyl)-1,3,6-Trihydro-6-Aza-3-Oxapentalen-2-One (A) 5-(p-Chlorobenzoyl)-α-ethyl-1-methylpyrrole-2-acetic acid A solution of 6.5 g (0.021 mole) of ethyl 5-(p-chlorobenzoyl)-1-methylpyrrole-2-acetate in 60 ml. of ether is added to a suspension of 1.25 g. (0.032 mole) of sodamide in 150 ml. of refluxing liquid ammonia. After 10 minutes, 4.98 g. (0.032 mole) of ethyl iodide is added. The mixture is stirred for 1.5 hours, and an additional 1.0 g. (0.0064 mole) of ethyl iodide is added. Stirring is continued for 30 minutes and ammonium chloride is then added to neutralize any anion. The mixture is allowed to warm to room temperature and the ammonia allowed to escape. Ether is added, and the mixture poured into dilute hydrochloric acid. The ether layer is separated, and the aqueous layer is washed with ether. The combined ether solutions are washed successively with sodium bisulfite solution and brine and then dried over anhydrous magnesium sulfate. The solvent is evaporated in vacuo to give about 7.4 g. of a yellow oily residue containing ethyl 5-(p-chlorobenzoyl)-α-ethyl-1-methylpyrrole-2-acetate, which is used as such in the following transformation to acid procedure. A 6.9 g. sample of the oily residue is dissolved in 30 ml. of ethanol and 11.4 ml. of 1N sodium hydroxide is added. The mixture is refluxed for 1 hour. The solvent is then evaporated in vacuo, and the residue partitioned between ether and water. The aqueous layer is separated and acidified with dilute hydrochloric acid. The precipitated oil, which is separated, crystallizes on scratching to give a solid, 5-(p-chlorobenzoyl)-α-ethyl-1-methylpyrrole-2-acetic acid, which is collected and dried, m.p. 108–112° C. After successive recrystallizations from ether-methylcyclohexane, benzene-hexane, methylcyclohexane and ether-hexane, the m.p. is 110–114° C. Analysis: Calcd. for $C_{16}H_{16}ClNO_3$: C, 62.84; H, 5.27; N, 4.58% Found: C, 63.01; H, 5.36; N, 4.61%

(B) Rac-1-ethyl-6-methyl-5-(p-chlorobenzoyl)-1,3,6-trihydro-6-aza-3-oxapentalen-2-one 5-(p-Chlorobenzoyl)-α-ethyl-1-methylpyrrole-2-acetic acid is subjected to the procedure of Example 1, part C to produce rac-1-ethyl-6-methyl-5-(p-chlorobenzoyl)-1,3,6-trihydro-6-aza-3-oxapentalen-2-one ($R_1$=ethyl, $R_2$=H, $R_3$=p-chlorophenyl, $R_4$=$CH_3$, $R_5$=H, Y=CO, m=1, n=0).

EXAMPLE 24

Rac-1-(n-Butyl)-6-Methyl-5-Benzoyl-1,3,6-Trihydro-6-Aza-3-Oxapentalen-2-One (A) 5-Benzoyl-α-(N-butyl)-1-methylpyrrole-2-acetic acid The alkylation and ester-to-acid transformation procedures of Example 23 are repeated except that an equivalent amount of an appropriate 5-Aryl-1-methylpyrrole-2-acetic acid alkyl ester and an equivalent amount of an appropriate alkyl halide alkylating agent are employed to yield 5-benzoyl-α-(n-butyl)-1-methylpyrrole-2-acetic acid.

(B) Rac-1-(n-butyl)-6-methyl-5-benzoyl-1,3,6-trihydro-6-aza-3-oxapentalen-2-one

5-Benzoyl-α-(n-butyl)-1-methylpyrrole-2-acetic acid is subjected to the procedure of Example 1, part C to produce rac-1-(n-butyl)-6-methyl-5-benzoyl-1,3,6-trihydro-6-aza-3-oxapentalen-2-one ($R_1$=n-butyl, $R_2$=H, $R_3$=phenyl, $R_4$=$CH_3$, $R_5$=H, Y=CO, m=1, n=0).

EXAMPLE 25

Rac-1,6-Dimethyl-5-(4'-Methoxybenzoyl)-1,3,6-Trihydro-6-Aza-3-Oxapentalen-2-One (A) 5-(p-Methoxybenzoyl)-α-methyl-1-methylpyrrole-2-acetic acid The alkylation and ester-to-acid transformation procedures of Example 23 are repeated except that an equivalent amount of an appropriate 5-Aryl-1-methylpyrrole-2-acetic acid alkyl ester and an equivalent amount of an appropriate alkyl halide alkylating agent are employed to yield 5-(p-methoxybenzoyl)-α-methyl-1-methylpyrrole-2-acetic acid.

(B) Rac-1,6-dimethyl-5-(4'-methoxybenzoyl)- 1,3,6-trihydro-6-aza-3-oxapentalen-2-one 5-(p-Methoxybenzoyl)-α-methyl-1-methylpyrrole-2-acetic acid is subjected to the procedure of Example 1, part C to produce rac-1,6-dimethyl-5-(4'-methoxybenzoyl)-1,3,6-trihydro-6-aza-3-oxapentalen-2-one ($R_1=CH_3$, $R_2=H$, $R_3=4'$-methoxyphenyl, $R_4=CH_3$, $R_5=H$, $Y=CO$, $m=1$, $n=0$).

EXAMPLE 26

Rac-1-(n-Propyl-6-Methyl-5-Benzoyl-1,3,6-Trihydro-6-Aza-3-Oxapentalen-2-One (A) 5-Benzoyl-α-(n-propyl)-1-methylpyrrole-2-acetic acid The alkylation and ester-to-acid transformation procedures of Example 23 are repeated except that an equivalent amount of an appropriate 5-Aryl-1-methylpyrrole-2-acetic acid alkyl ester and an equivalent amount of an appropriate alkyl halide alkylating agent are employed to yield 5-benzoyl-α-(n-propyl)-1-methylpyrrole-2-acetic acid.

(B) Rac-1-(n-propyl)-6-methyl-5-benzoyl-1,3,6-trihydro-6-aza-3-oxapentalen-2-one 5-Benzoyl-α-(n-propyl)-1-methylpyrrole-2-acetic acid is subjected to the procedure of Example 1, part C to produce rac-1-(n-propyl)-6-methyl-5-benzoyl- 1,3,6-trihydro-6-aza-3 -oxapentalen-2-one ($R_1$=n-propyl, $R_2=H$, $R_3$=phenyl, $R_4=CH_3$, $R_5=H$, $Y=CO$, $m=1$, $n=0$).

EXAMPLE 27

Rac-1,6-Dimethyl-5-(4'-Cyanobenzoyl)-1,3,6-Trihydro-6-Aza-3-Oxapentalen-2-One (A) 5-(p-Cyanobenzoyl)-α-methyl-1-methylpyrrole-2-acetic acid The alkylation and ester-to-acid transformation procedures of Example 23 are repeated except that an equivalent amount of an appropriate 5-Aryl-1-methylpyrrole-2-acetic acid alkyl ester and an equivalent amount of an appropriate alkyl halide alkylating agent are employed to yield 5-(p-cyanobenzoyl)-α-methyl-1-methylpyrrole-2-acetic acid.

(B) Rac-1,6-dimethyl-5-(4'-cyanobenzoyl)-1,3,6-trihydro-6-aza-3-oxapentalen-2-one 5-(p-Cyanobenzoyl)-α-methyl-1-methylpyrrole-2-acetic acid is subjected to the procedure of Example 1, part C to produce ($R_1=CH_3$, $R_2=H$, $R_3=4'$-cyanophenyl, $R_4=CH_3$, $R_5=H$, $Y=CO$, $m=1$, $n=0$).

EXAMPLE 28

Rac-1,6-Dimethyl-5-(3'-Chlorobenzoyl)-1,3,6-Trihydro-6-Aza-3-Oxapentalen-2-One (A) 5-(m-Chlorobenzoyl)-α-methyl-1-methylpyrrole-2-acetic acid The alkylation and nitrile-to-acid transformation procedures of Examples 22C and 22D, respectively, are repeated except that an equivalent amount of an appropriate 5-Aryl-1-methylpyrrole-2-acetonitrile and an equivalent amount of an appropriate alkyl halide alkylating agent are employed to yield 5-(m-chlorobenzoyl)-α-methyl-1-methylpyrrole-2-acetic acid.

(B) Rac-1,6-dimethyl-5-(3'-chlorobenzoyl)-1,3,6-trihydro-6-aza-3-oxapentalen-2-one 5-(m-Chlorobenzoyl)-α-methyl-1-methylpyrrole-2-acetic acid is subjected to the procedure of Example 1, part C to produce rac-1,6-dimethyl-5-(3'-chlorobenzoyl)-1,3,6-trihydro-6-aza-3-oxapentalen-2-one ($R_1=CH_3$, $R_2=H$, $R_3=3'$-chlorophenyl, $R_4=CH_3$, $R_5=H$, $Y=CO$, $m=1$, $n=0$).

EXAMPLE 29

Rac-1-Ethyl-6-Methyl-5-(4'-Fluorobenzoyl)-1,3,6-Trihydro-6-Aza-3-Oxapentalen-2-One (A) 5-(p-Fluorobenzoyl)-α-ethyl-1-methylpyrrole-2-acetic acid The alkylation and nitrile-to-acid transformation procedures of Examples 22C and 22D, respectively, are repeated except that an equivalent amount of an appropriate 5-Aryl-1-methylpyrrole-2-acetonitrile and an equivalent amount of an appropriate alkyl halide alkylating agent are employed to yield 5-(p-fluorobenzoyl)-α-ethyl-1-methylpyrrole-2-acetic acid.

(B) rac-1-ethyl-6-methyl-5-(4'-fluorobenzoyl)-1,3,6-trihydro-6-aza-3 -oxapentalen-2-one 5-(p-Fluorobenzoyl)-α-ethyl-1-methylpyrrole-2-acetic acid is subjected to the procedure of Example 1, part C to produce rac-1-ethyl-6-methyl-5-(4'-fluorobenzoyl)-1,3,6-trihydro-6-aza-3-oxapentaten-2-one ($R_1$=ethyl, $R_2=H$, $R_3=4'$-fluorophenyl, $R_4=CH_3$, $R_5=H$, $Y=CO$, $m=1$, $n=0$).

EXAMPLE 30

Rac-1,6-Dimethyl-5-(4'-Methylbenzoyl)-1,3 6-Trihydro-6-Aza-3-Oxapentalen-2-One (A) 5-(p-Methylbenzoyl)-α-ethyl-1-methylpyrrole-2-acetic acid The alkylation and nitrile-to-acid transformation procedures of Examples 22C and 22D, respectively, are repeated except that an equivalent amount of an appropriate 5-Aryl-1-methylpyrrole-2-acetonitrile and an equivalent amount of an appropriate alkyl halide alkylating agent are employed to yield 5-(p-methylbenzoyl)-α-ethyl-1-methylpyrrole-2-acetic acid.

(B) rac-1,6-dimethyl-5-(4'-methylbenzoyl)-1,3,6-trihydro-6-aza-3-oxapentalen-2-one 5-(p-Methylbenzoyl)-α-ethyl-1-methylpyrrole-2-acetic acid is subjected to the procedure of Example 1, part C to produce rac-1,6-dimethyl-5-(4'-methylbenzoyl)-1,3,6-trihydro-6-aza-3-oxapentalen-2-one ($R_1=CH_3$, $R_2=H$, $R_3=4'$-Methylphenyl, $R_4=CH_3$, $R_5=H$, $Y=CO$, $m=1$, $n=0$).

EXAMPLE 31

Rac-1,6-Dimethyl-5-(2',4'-Dichlorobenzoyl)-1,3,6-Trihydro-6-Aza-3-Oxapentalen-2-One (A) 5-(2',4'-Dichlorobenzoyl)-α-methyl-1-methylpyrrole-2-acetic acid The alkylation and nitrile-to-acid transformation procedures of Examples 22C and 22D, respectively, are repeated except that an equivalent amount of an appropriate 5-Aryl-1-methylpyrrole-2-acetonitrile and an equivalent amount of an appropriate alkyl halide alkylating agent are employed to yield 5-(2',4'-dichlorobenzoyl)-α-methyl-1-methylpyrrole-2-acetic acid.

(B) rac-1,6-dimethyl-5-(2',4'-dichlorobenzoyl)-1,3,6-trihydro-6-aza-3 -oxapentalen-2-one 5-(2',4'-Dichlorobenzoyl)-α-methyl-1-methylpyrrole-2-acetic acid is subjected to the procedure of Example 1, part C to produce rac-1,6-dimethyl-5-(2',4'-dichlorobenzoyl)-1,3,6 -trihydro-6-aza-3-oxapentalen-2-one ($R_1$=$CH_3$, $R_2$=H, $R_3$=2',4'-dichlorophenyl, $R_4$=$CH_3$, $R_5$=H, Y=CO, m=1, n=0).

EXAMPLE 32

Rac-1-Ethyl-6-Methyl-5-(3'-Chloro-4'-Methylbenzoyl)-1,3,6-Trihydro-6-Aza-3-Oxapentalen-2-One (A) 5-(3'-Chloro-4'-methylbenzoyl)-α-ethyl-1-methylpyrrole-2-acetic acid.

The alkylation and nitrile-to-acid transformation procedures of Examples 22C and 22D, respectively, are repeated except that an equivalent amount of an appropriate 5-Aryl-1-methylpyrrole-2-acetonitrile and an equivalent amount of an appropriate alkyl halide alkylating agent are employed to yield 5-(3'-chloro-4'-methylbenzoyl)-α-ethyl-1-methylpyrrole-2-acetic acid.

(B) rac-1-ethyl-6-methyl-5-(3'-chloro-4'-methylbenzoyl)-1,3,6-trihydro-6-aza-3 -oxapentalen-2-one 5-(3'-Chloro-4'-methylbenzoyl)-α-ethyl-1-methylpyrrole-2-acetic acid is subjected to the procedure of Example 1, part C to produce rac-1-ethyl-6-methyl-5-(3'-chloro-4'-methylbenzoyl)-1,3,6-trihydro-6-aza-3-oxapentalen-2-one ($R_1$=$CH_3$, $R_2$=H, $R_3$=3'-Chloro-4'-Methylphenyl, $R_4$=$CH_3$, $R_5$=H, Y=CO, m=1, n=0).

EXAMPLE 33

5-(4'-Chlorobenzoyl)-1,3,6-Trihydro-6-Aza-3-Oxapentalen-2-One (A) 5-(p-Chlorobenzoyl)-pyrrole-2-acetonitrile To a chilled suspension of 26.80 g. (0.2 mole) of aluminum chloride in 110 ml. of methylene chloride is added dropwise 35 g. (0.2 mole) of p-chlorobenzoyl chloride. The mixture is added dropwise to a solution of 21.22 g. (0.2 mole) of pyrrole-2-acetonitrile in 125 ml. methylene chloride which is cooled externally with an ammonium chloride ice bath. After addition is complete, the reaction mixture is stirred for ten minutes at 0° C. and then poured into ice acidified with dilute hydrochloric acid. A solid precipitate, 5-(p-chlorobenzoyl)-pyrrole-2-acetonitrile, which is filtered off, washed with hot methanol and dried, m.p. 203–205° C.

(B) 5-(p-Chlorobenzoyl)-pyrrole-2-acetic acid

A solution of 3.6 g. (0.015 mole) of 5-(p-chlorobenzoyl)-pyrrole-2-acetonitrile, 30 ml. 1N sodium hydroxide solution, and 30 ml. 95% ethanol is refluxed and stirred for 6 hours. The ethanol is evaporated off in vacuo. The resulting solid is dissolved in water and the solution filtered from insolubles. The filtrate is acidified with dilute hydrochloric acid. A white solid precipitates, 5-(p-chlorobenzoyl)-pyrrole-2-acetic acid, which is purified by recrystallization from acetone water (1:1), m.p. 210° C.

(C) BOC 5-(p-chlorobenzoyl)-pyrrole-2-acetic acid

The pyrrole nitrogen is protected with the t-butyl carbamate group employing $(BOC)_2O$ as a reagent according to D.S. Tarbell Proc. Natl. Acad. Sci (USA), 69, 730 (1972).

(D) BOC 5-(4'-chlorobenzoyl)-1,3,6-trihydro-6-aza-3-oxapentalene-2-one

BOC 5-(p-chlorobenzoyl)-pyrrole-2-acetic acid is subjected to the procedure of Example 1, part C to produce BOC 5-(4'-chlorobenzoyl)-1,3,6-trihydro-6-aza-3-oxapentalen-2-one (C) 5-(4'-Chlorobenzoyl)-1,3,6-trihydro-6-aza-3-oxapentalene-2-one The BOC group is removed from the BOC-lactone employing trifluoroacetic acid as a reagent according to Y. Masui, Bull. Chem. Soc. Japan 53, 464 (1980)($R_1$=H, $R_2$=H, $R_3$=4'-chlorophenyl, $R_4$=H, $R_5$=H, Y=CO, m=1, n=0).

EXAMPLE 34

5-Benzoyl-1,3,6-Trihydro-6-Aza-3-Oxapentalen-2-One (A) 5-Benzoyl-pyrrole-2-acetonitrile The procedure of Example 33A is repeated, except that an equivalent amount of an appropriate benzoyl chloride is used in place of the p-chlorobenzoyl chloride used therein 5-benzoyl-pyrrole-2-acetonitrile is obtained.

(B) 5-Benzoyl-pyrrole-2-acetic acid

The procedure of Example 33B is repeated using an equivalent amount of 5-benzoyl-pyrrole-2-acetonitrile obtained in part A of this Example in place of 5-(p-chlorobenzoyl)-pyrrole-2-acetonitrile to yield 5-benzoyl-pyrrole-2-acetic acid.

(C) BOC 5-benzoyl-pyrrole-2-acetic acid

The procedure of Example 33C is repeated using 5-benzoyl-pyrrole-2-acetic acid to produce BOC 5-benzoyl-pyrrole-2-acetic acid.

(D) BOC 5-benzoyl-1,3,6-trihydro-6-aza-3-oxapentalen-2-one

BOC 5-benzoyl-pyrrole-2-acetic acid is subjected to the procedure of Example 1, part C to produce BOC 5-benzoyl-1,3,6-trihydro-6-aza-3-oxapentalen-2-one.

(E) 5-benzoyl-1,3,6-trihydro-6-aza-3-oxapentalen-2-one

The procedure of Example 33E is repeated using BOC 5-benzoyl-1,3,6-trihydro-6-aza-3-oxapentalen-2-one to produce 5-benzoyl-1,3,6-trihydro-6-aza-3-oxapentalen-2-one ($R_1$=H, $R_2$=H, $R_3$=phenyl, $R_4$=H, $R_5$=H, Y=CO, m=1, n=0).

EXAMPLE 35

5-(p-Fluorobenzoyl)-1,3,6-Trihydro-6-Aza-3-Oxapentalen-2-One (A) 5-(p-Fluorobenzoyl)-pyrrole -2-acetonitrile The procedure of Example 33A is repeated, except that an equivalent amount of an appropriate benzoyl chloride is used in place of the p-chlorobenzoyl chloride used therein to give 5-(p-fluorobenzoyl)-pyrrole -2-acetonitrile.

(B) 5-(p-Fluorobenzoyl)-pyrrole-2-acetic acid

The procedure of Example 33B is repeated using an equivalent amount of 5-(p-fluorobenzoyl)-pyrrole-2-acetonitrile obtained in part A of this Example in place of 5-(p-chlorobenzoyl)-pyrrole-2-acetonitrile to yield 5-(p-fluorobenzoyl)-pyrrole-2-acetic acid.

(C) BOC 5-(p-fluorobenzoyl)-pyrrole-2-acetic acid

The procedure of Example 33C is repeated using 5-(p-fluorobenzoyl)-pyrrole-2-acetic acid to give BOC 5-(p-fluorobenzoyl)-pyrrole-2-acetic acid.

(D) BOC 5-(p-fluorobenzoyl)-1,3,6-trihydro-6-aza-3-oxapentalen-2-one

BOC 5-(p-fluorobenzoyl)-pyrrole-2-acetic acid is subjected to the procedure of Example 1, part C to produce BOC 5-(p-fluorobenzoyl)-1,3,6-trihydro-6-aza-3-oxapentalen-2-one.

(E) 5-(p-Fluorobenzoyl)-1,3,6-trihydro-6-aza-3-oxapentalen-2-one

The procedure of Example 33E is repeated using BOC 5-(p-fluorobenzoyl)-1,3,6-trihydro-6-aza-3-oxapentalen-2-one to give 5-(p-fluorobenzoyl)-1,3,6-trihydro-6-aza-3-oxapentalen-2-one ($R_1$=H, $R_2$=H, $R_3$=4'-fluorophenyl, $R_4$=H, $R_5$=H, Y=CO, m=1, n =0).

EXAMPLE 36

5-(p-Methylbenzoyl)-1,3,6-Trihydro-6-Aza-3-Oxapentalen-2-One (A) 5-(p-methylbenzoyl)-pyrrole-2-acetonitrile The procedure of Example 33A is repeated, except that an equivalent amount of an appropriate benzoyl chloride is used in place of the p-chlorobenzoyl chloride used therein 5-(p-methylbenzoyl)-pyrrole-2-acetonitrile is obtained.

(B) 5-(p-Methylbenzoyl)-pyrrole-2-acetic acid

The procedure of Example 33B is repeated using an equivalent amount of each pyrrole-acetonitrile obtained in part A of this Example in place of 5-(p-chlorobenzoyl)-pyrrole-2-acetonitrile to yield 5-(p-methylbenzoyl)-pyrrole-2-acetic acid.

(C) BOC 5-(p-methylbenzoyl)-pyrrole-2-acetic acid.

The procedure of Example 33C is repeated using 5-(p-methylbenzoyl)-pyrrole-2-acetic acid to give BOC 5-(p-methylbenzoyl)-pyrrole-2-acetic acid (D) BOC 5-(p-methylbenzoyl)-1,3,6-trihydro-6-aza-3-oxapentalen-2-one BOC 5-(p-methylbenzoyl)-pyrrole-2-acetic acid is subjected to the procedure of Example 1, part C to produce BOC 5-(p-methylbenzoyl)-1,3,6-trihydro-6-aza-3-oxapentalen-2-one.

(E) 5-(p-methylbenzoyl)-1,3,6-trihydro-6-aza-3-oxapentalen-2-one

The procedure of Example 33E is repeated using produce BOC 5-(p-methylbenzoyl)-1,3,6-trihydro-6-aza-3-oxapentalen-2-one to yield 5-(p-methylbenzoyl)-1,3,6-trihydro-6-aza-3-oxapentalen-2-one ($R_1$=H, $R_2$=H, $R_3$=4'-methylphenyl, $R_4$=H, $R_5$=H, Y=CO, m=1, n=0).

EXAMPLE 37

5-(p-Methoxybenzoyl)-1,3,6-Trihydro-6-Aza-3-Oxapentalen-2-One (A) 5-(p-methoxybenzoyl)-pyrrole-2-acetonitrile The procedure of Example 33A is repeated, except that an equivalent amount of an appropriate benzoyl chloride is used in place of the p-chlorobenzoyl chloride used therein 5-(p-methoxybenzoyl)-pyrrole-2-acetonitrile is obtained.

(B) 5-(p-methoxybenzoyl)-pyrrole-2-acetic acid

The procedure of Example 33B is repeated using an equivalent amount of 5 -(p-methoxybenzoyl)-pyrrole-2-acetonitrile obtained in part A of this Example in place of 5-(p-chlorobenzoyl)-pyrrole-2-acetonitrile to yield 5-(p-methoxybenzoyl)-pyrrole-2-acetic acid.

(C) BOC 5-(p-methoybenzoyl)-pyrrole-2-acetic acid

The procedure of Example 33C is repeated using 5-(p-methoxybenzoyl)-pyrrole-2-acetic acid to give BOC 5-(p-methoybenzoyl)-pyrrole-2-acetic acid.

(D) BOC 5-(p-methoxybenzoyl)-1,3,6-trihydro-6-aza-3-oxapentalen-2-one

BOC 5-(p-methoxybenzoyl)-pyrrole-2-acetic acid is subjected to the procedure of Example 1, part C to produce BOC 5-(p-methoxybenzoyl)-1,3,6-trihydro-6-aza-3-oxapentalen-2-one.

(E) 5-(p-methoxybenzoyl)-1,3,6-trihydro-6-aza-3-oxapentalen-2-one

The procedure of Example 33E is repeated using BOC 5-(p-methoxybenzoyl)-1,3,6-trihydro-6-aza-3-oxapentalen-2-one to produce 5-(p-methoxybenzoyl)-1,3,6-trihydro-6-aza-3-oxapentalen-2-one ($R_1$=H, $R_2$=H, $R_3$=4'-methoxyphenyl, $R_4$=H, $R_5$=H, Y=CO, m =1, n=0).

EXAMPLE 38

5-(3'-Chloro-4'-Methoxybenzoyl)-1,3,6-Trihydro-6-Aza-3-Oxapentalen-2-One (A) 5-(3'-chloro-4'-methoxybenzoyl)-pyrrole-2-acetonitrile The procedure of Example 33A is repeated, except that an equivalent amount of an appropriate benzoyl chloride is used in place of the p-chlorobenzoyl chloride used therein to give 5-(3'-chloro-4'-methoxybenzoyl)-pyrrole-2-acetonitrile.

(B) 5-(3'-Chloro-4'-methylbenzoyl)-pyrrole-2-acetic acid

The procedure of Example 33B is repeated using an equivalent amount of 5-(3'-chloro-4'-methoxybenzoyl)-pyrrole-2-acetonitrile obtained in part A of this Example in place of 5-(p-chlorobenzoyl)-pyrrole-2-acetonitrile to yield 5-(3'-chloro-4'-methylbenzoyl)-pyrrole-2-acetic acid.

(C) BOC 5-(3'-chloro-4'-methylbenzoyl)-pyrrole-2-acetic acid

The procedure of Example 33C is repeated using 5-(3'-chloro-4'-methylbenzoyl)-pyrrole-2-acetic acid to yield BOC 5-(3'-chloro-4'-methylbenzoyl)-pyrrole-2-acetic acid.

(D) BOC 5-(3'-chloro-4'-methoxybenzoyl)-1,3,6-trihydro-6-aza-3-oxapentalen-2-one BOC 5-(3'-chloro-4'-methylbenzoyl)-pyrrole-2-acetic acid is subjected to the procedure of Example 1, part C to produce BOC 5-(3'-chloro-4'-methoxybenzoyl)-1,3,6-trihydro-6-aza-3-oxapentalen-2-one.

(E) 5-(3'-chloro-4'-methoxybenzoyl)-1,3,6-trihydro-6-aza-3-oxapentalen-2-one

The procedure of Example 33E is repeated using BOC 5-(3'-chloro-4'-methoxybenzoyl)-1,3,6-trihydro-6-aza-3-oxapentalen-2-one to yield 5-(3'-chloro-4'-methoxybenzoyl)-1,3,6-trihydro-6-aza-3-oxapentalen-2-one ($R_1$=H, $R_2$=H, $R_3$=3'-chloro-4'-methylphenyl, $R_4$=H, $R_5$=H, Y=CO, m=1, n=0).

EXAMPLE 39

5-(2',4'-Dichlorobenzoyl)-1,3,6-Trihydro-6-Aza-3-Oxapentalen-2-One (A) 5-(2',4'-dichlorobenzoyl)-pyrrole-2-acetonitrile The procedure of Example 33A is repeated, except that an equivalent amount of an appropriate benzoyl chloride is used in place of the p-chlorobenzoyl chloride to give 5-(2',4'-dichlorobenzoyl)-pyrrole-2-acetonitrile.

(B) 5-(2',4'-dichlorobenzoyl)-pyrrole-2-acetic acid

The procedure of Example 33B is repeated using an equivalent amount of 5-(2',4'-dichlorobenzoyl)-pyrrole-2-acetonitrile obtained in part A of this Example in place of 5-(p-chlorobenzoyl)-pyrrole-2-acetonitrile to yield 5-(2',4'-dichlorobenzoyl)-pyrrole-2-acetic acid.

(C) BOC 5-(2',4'-dichlorobenzoyl)-pyrrole-2-acetic acid

The procedure of Example 33C is repeated using 5-(2',4'-dichlorobenzoyl)-pyrrole-2 -acetic acid to produce BOC 5-(2',4'-dichlorobenzoyl)-pyrrole-2-acetic acid.

(D) BOC 5-(2',4'-dichlorobenzoyl)-1,3,6-trihydro-6-aza-3-oxapentalen-2-one

BOC 5-(2',4'-dichlorobenzoyl)-pyrrole-2-acetic acid is subjected to the procedure of Example 1, part C to produce BOC 5-(2',4'-dichlorobenzoyl)-1,3,6-trihydro-6-aza-3-oxapentalen-2-one.

(E) 5-(2',4'-dichlorobenzoyl)-1,3,6-trihydro-6-aza-3-oxapentalen-2-one

The procedure of Example 33E is repeated using BOC 5-(2',4'-dichlorobenzoyl)-1,3,6-trihydro-6-aza-3-oxapentalen-2-one to yield 5-(2',4'-dichlorobenzoyl)-1,3,6-trihydro-6 -aza-3-oxapentalen-2-one ($R_1$ H, $R_2$=H, $R_3$=2',4'-dichlorophenyl, $R_4$=H, $R_5$=H, Y=CO,m=1,n=0).

EXAMPLE 40

6-Ethyl-5-(4'-Chlorobenzoyl)-1,3 6-Trihydro-6-Aza-3-Oxapentalen-2-One (A) 5-(p-chlorobenzoyl)-1-ethylpyrrole-2-acetonitrile A mixture of 24.4 g. (0.1 mole) 5-(p-chlorobenzyl)-pyrrole-2-acetonitrile, 41.7 g. (0.3 mole) of potassium carbonate and 16.1 g. (0.105 mole) of ethyl iodide in 300 ml. of methylethylketone is refluxed overnight. The reaction mixture is then poured into water and extracted with chloroform. The organic solutions are combined, dried over anhydrous magnesium sulfate, and the solvent evaporated in vacuo. The residue is crystallized from 2 -propanol to give about 13 g. of crude solid. The solid is sublimed overnight at 140° C. and 0.025 mm. Hg. The sublimate is successively recrystallized from 2-propanol, benzene and hexane to give 5-(p-chlorobenzoyl)-1-ethylpyrrole-2-acetonitrile as a white solid, m.p. 145–147° C. Analysis: Calcd. for $C_{15}H_{13}ClN_2O$: N, 10.2%. Found: N, 10.54%.

(B) 5-(p-chlorobenzoyl)-1-ethylpyrrole-2-acetic acid

A suspension of 3.52 g. (0.013 mole) of 5-(p-chlorobenzoyl)-1-ethylpyrrole-2 -acetonitrile in 26 ml. 1N sodium hydroxide and 50 ml. of ethanol is refluxed for six hours. The mixture is then diluted with water and cooled. A solid precipitates which is filtered off and set aside. The ethanol is evaporated from the filtrate in vacuo. The collected precipitate is added to the concentrated filtrate, and the mixture is extracted with chloroform. The aqueous phase is separated, acidified with dilute hydrochloric acid, and the resulting precipitate (A) is collected by filtration and dried. The chloroform phase is evaporated and the residue refluxed with 12 ml. of 1N sodium hydroxide and 24 ml. of ethanol for 6 hours. The ethanol is evaporated in vacuo, and the remaining solution is diluted with water and washed with chloroform. The aqueous solution is acidified with dilute hydrochloric acid and the precipitated solid (B) is collected and dried. The two samples of acidic material (A and B) are combined and recrystallized from aqueous isopropanol to give 5-(p-chlorobenzoyl)-1 -ethylpyrrole-2-acetic acid as a white solid, m.p. 149–153° C. Analysis: Calcd. for $C_{15}H_{14}ClNO_3$: C, 61.75; H, 4.83; N, 4.80%. Found: C, 61.78; H, 4.94; N, 4.96%.

(C) 6-ethyl-5-(4'-chlorobenzoyl)-1,3,6-trihydro-6-aza-3-oxapentalen-2-one 5-(p-Chlorobenzoyl)-1-ethylpyrrole-2-acetic acid is subjected to the procedure of Example 1, part C to yield 6-ethyl-5-(4'-chlorobenzoyl)-1,3,6-trihydro-6-aza-3-oxapentalen-2-one ($R_1$ H, $R_2$=H, $R_3$=4'-chlorophenyl, $R_4$=ethyl, $R_5$=H, Y=CO, m=1, n=0)

EXAMPLE 41

6-(n-Propyl)-5-(4'-Methylphenyl)-1,3,6-Trihydro-6-Aza-3-Oxapentalen-2-One (A) 5-(p-methylbenzoyl)-1-(n-propyl)pyrrole-2-acetonitrile The N-alkylation procedure of Example 40A is followed with an equivalent amount of N-unsubstituted 5-(p-methylbenzoyl)-pyrrole-2-acetonitrile and an equivalent amount of n-propyl iodide as the N-alkylating agent, to yield 5-(p-methylbenzoyl)-1-(n-propyl)pyrrole-2-acetonitrile.

(B) 5-(p-methylbenzoyl)-1-(n-propyl)pyrrole-2-acetic acid

The nitrile-to-acid transformation procedure of Example 40B is repeated, except that an equivalent amount of the acetonitrile obtained in part A of this Example is used as the starting acetonitrile to yield 5-(p-methylbenzoyl)-1-(n-propyl)pyrrole-2-acetic acid.

(C) 6-(n-propyl)-5-(4'-methylphenyl)-1,3,6-trihydro-6-aza-3-oxapentalen-2-one 5-(p-methylbenzoyl)-1-(n-propyl)pyrrole-2-acetic acid is subjected to the procedure of Example 1, part C to produce 6-(n-propyl)-5-(4'-methylphenyl)-1,3,6-trihydro-6-aza-3-oxapentalen-2-one ($R_1$=H, $R_2$=H, $R_3$=4'-methylphenyl, $R_4$=n-propyl, $R_5$=H, Y=CO, m=1, n=0)

EXAMPLE 42

6-Ethyl-5-(4'-Methoxyphenyl)-1,3,6-Trihydro-6-Aza-3-Oxapentalen-2-One (A) 5-(p-methoxybenzoyl)-1-ethylpyrrole -2-acetonitrile The N-alkylation procedure of Example 40A is followed with an equivalent amount of N-unsubstituted 5-(p-methoxybenzoyl)-pyrrole-2-acetonitrile and an equivalent amount of ethyl iodide as the N-alkylating agent, to yield 5-(p-methoxybenzoyl)-1-ethylpyrrole -2 -acetonitrile.

(B) 5-(p-methoxybenzoyl)-1-ethylpyrrole-2-acetic acid

The nitrile-to-acid transformation procedure of Example 40B is repeated, except that an equivalent amount of the acetonitrile obtained in part A of this Example is used as the starting acetonitrile to yield 5-(p-methoxybenzoyl)-1-ethylpyrrole-2-acetic acid.

(C) 6-ethyl-5-(4'-methoxyphenyl)-1,3,6-trihydro-6-aza-3-oxapentalen-2-one 5-(p-methoxybenzoyl)-1-ethylpyrrole-2-acetic acid is subjected to the procedure of Example 1, part C to produce 6-ethyl-5-(4'-methoxyphenyl)-1,3,6-trihydro-6-aza-3-oxapentalen-2-one ($R_1$ H, $R_2$=H, $R_3$=4'-methoxyphenyl, $R_4$=ethyl, $R_5$=H, Y=CO, m =1, n=0).

EXAMPLE 43

6-(n-Butyl)-5-(2',4'-Dichlorobenzoyl)-1,3,6-Trihydro-6-Aza-3-Oxapentalen-2-One (A) 5-(2',4'-dichlorobenzoyl)-1-(n-butyl)pyrrole-2-acetonitrile The N-alkylation procedure of Example 40A is followed with an equivalent amount of N-unsubstituted 5-(2',4'-dichlorobenzoyl)-pyrrole-2-acetonitrile and an equivalent amount of n-butyl iodide as the N-alkylating agent, to yield 5-benzoyl-1-ethylpyrrole-2-acetonitrile 5-(2',4'-dichlorobenzoyl)-1-(n-butyl)pyrrole-2 -acetonitrile.

(B) 5-(2',4'-dichlorobenzoyl)-1-(n-butyl)pyrrole-2-acetic acid

The nitrile-to-acid transformation procedure of Example 40B is repeated, except that an equivalent amount of the acetonitrile obtained in part A of this Example is used as the starting acetonitrile to yield 5-(2',4'-dichlorobenzoyl)-1-(n-butyl)pyrrole-2-acetic acid.

(C) 6-(n-butyl)-5-(2',4'-dichlorobenzoyl)-1,3,6-trihydro-6-aza-3-oxapentalen-2-one 5-(2',4'-dichlorobenzoyl)-1-(n-butyl)pyrrole-2-acetic acid is subjected to the procedure of Example 1, part C to produce 6-(n-butyl)-5-(2',4'-dichlorobenzoyl)-1,3,6 -trihydro-6-aza-3-oxapentalen-2-one ($R_1$=H, $R_2$=H, $R_3$=2',4'-dichlorophenyl, $R_4$ =n-butyl, $R_5$=H, Y=CO, m=1, n=0).

EXAMPLE 44

6-Ethyl-5-Benzoyl-1,3,6-Trihydro-6-Aza-3-Oxapentalen-2-One (A) 5-benzoyl-1-ethylpyrrole -2-acetonitrile The N-alkylation procedure of Example 40A is followed with an equivalent amount of N-unsubstituted 5-benzoyl-pyrrole-2-acetonitrile and an equivalent amount of ethyl iodide as the N-alkylating agent, to yield 5-benzoyl-1-ethylpyrrole-2-acetonitrile.

(B) 5-benzoyl-1-ethylpyrrole-2-acetic acid

The nitrile-to-acid transformation procedure of Example 40B is repeated, except that an equivalent amount of the acetonitrile obtained in part A of this Example is used as the starting acetonitrile to yield 5-benzoyl-1-ethylpyrrole-2-acetic acid.

(C) 6-ethyl-5-benzoyl-1,3,6-trihydro-6-aza-3-oxapentalen-2-one 5-benzoyl-1-ethylpyrrole-2-acetic acid is subjected to the procedure of Example 1, part C to produce 6-ethyl-5-benzoyl-1,3,6-trihydro-6-aza-3-oxapentalen-2-one ($R_1$=H, $R_2$=H, $R_3$=phenyl, $R_4$=ethyl, $R_5$=H, Y=CO, m=1, n=0).

EXAMPLE 45

Rac-1-Methyl-6-Ethyl-5-(p-Chlorobenzoyl)-1,3,6-Trihydro-6-Aza-3-Oxapentalen-2-One (A) 5-(p-chlorobenzoyl)-α-methyl-1-ethylpyrrole-2-acetic acid The alkylation and transformation procedures of Examples 22C and 22D, respectively, are repeated, except that an equivalent amount of the alkyl pyrrole-acetonitrile obtained in Example 40 is used in place of the starting acetonitrile used in Example 22C, and an equivalent amount of methyl iodide is used as the alkylating agent, to yield 5-(p-chlorobenzoyl)-α-methyl-1-ethylpyrrole-2-acetic acid.

(B) rac-1-methyl-6-ethyl-5-(p-chlorobenzoyl)-1,3,6-trihydro-6-aza-3-oxapentalen-2-one 5-(p-chlorobenzoyl)-α-methyl-1-ethylpyrrole-2-acetic acid is subjected to the procedure of Example 1, part C to produce rac-1-methyl-6-ethyl-5-(p-chlorobenzoyl)-1,3,6-trihydro-6-aza-3-oxapentalen-2-one ($R_1$=methyl, $R_2$=H, $R_3$=p-chlorophenyl, $R_4$=ethyl, $R_5$=H, Y=CO, m=1, n=0).

EXAMPLE 46

Rac-1-Methyl-6-Ethyl-5-Benzoyl-13,6-Trihydro-6-Aza-3-Oxapentalene-2-One (A) 5-benzoyl-α-methyl-1-ethylpyrrole-2-acetic acid The alkylation and transformation procedures of Examples 22C and 22D, respectively, are repeated, except that an equivalent amount of alkyl pyrrole-acetonitrile obtained in Example 44 is used in place of the starting acetonitrile used in Example 22C, and an equivalent amount of methyl iodide is used as the alkylating agent, to yield 5-benzoyl-α-methyl-1-ethylpyrrole-2-acetic acid.

(B) rac-1-methyl-6-ethyl-5-benzoyl-1,3,6-trihydro-6-aza-3-oxapentalene-2-one 5-benzoyl-α-methyl-1-ethylpyrrole-2-acetic acid is subjected to the procedure of Example 1, part C to produce rac-1-methyl-6-ethyl-5-benzoyl-1,3,6-trihydro-6-aza-3-oxapentalene-2-one ($R_1$=methyl, $R_2$=H, $R_3$=phenyl, $R_4$=ethyl, $R_5$=H, Y=CO, m=1, n=0).

EXAMPLE 47

Rac-1-Ethyl-6-(n-Propyl)-5-(p-Methylbenzoyl)-1,3,6-Trihydro-6-Aza-3-Oxapentalen-2-One (A) 5-(p-methylbenzoyl)-α-ethyl-1-(n-propyl)pyrrole-2-acetic acid The alkylation and transformation procedures of Examples 22C and 22D, respectively, are repeated, except that an equivalent amount of alkyl pyrrole-acetonitrile obtained in Example 41 is used in place of the starting acetontrile used in Example 22C, and an equivalent amount of ethyl iodide is used as the alkylating agent, to yield 5-(p-methylbenzoyl)-α-ethyl-1-(n-propyl)pyrrole-2-acetic acid.

(B) rac-1-ethyl-6-(n-propyl)-5-(p-methylbenzoyl)-1,3,6-trihydro-6-aza-3-oxapentalen-2-one 5-(p-methylbenzoyl)-α-ethyl-1-(n-propyl)pyrrole-2-acetic acid is subjected to the procedure of Example 1, part C to produce rac-1-ethyl-6-(n-propyl)-5-(p-methylbenzoyl)-1,3,6-trihydro-6-aza-3-oxapentalen-2-one ($R_1$=ethyl, $R_2$=H, $R_3$=4'-methylphenyl, $R_4$ =n-propyl, $R_5$=H, Y=CO, m=1, n=0).

EXAMPLE 48

Rac-1-Methyl-6-(n-Butyl)-5-(2',4'-Dichlorobenzoyl)-1,3,6-Trihydro-6-Aza-3-Oxapentalen-2-One (A) 5-(2',4'-Dichlorobenzoyl)-α-methyl-1-(n-butylpyrrole)-2-acetic acid The alkylation and transformation procedures of Examples 22C and 22D, respectively, are repeated, except that an equivalent amount of alkyl pyrrole-acetonitrile obtained in Example 43 is used in place of the starting acetonitrile used in Example 22C, and an equivalent amount of methyl iodide is used as the alkylating agent, to yield 5-(2',4'-dichlorobenzoyl)-α-methyl-1-(n-butylpyrrole)-2-acetic acid (B) rac-1-methyl-6-(n-butyl)-5-(2',4'-dichlorobenzoyl)-1,3,6-trihydro-6-aza-3-oxapentalen-2-one 5-(2',4'-dichlorobenzoyl)-α-methyl-1-(n-butylpyrrole)-2-acetic acid is subjected to the procedure of Example 1, part C to produce rac-1-methyl-6-(n-butyl)-5-(2',4'-dichlorobenzoyl)-1,3,6-trihydro-6-aza-3-oxapentalen-2-one ($R_1$=methyl, $R_2$=H, $R_3$=2', 4'-dichlorophenyl, $R_4$=n-butyl, $R_5$=H, Y=CO, m=1, n=0).

EXAMPLE 49

6-Benzyl-5-(4'-Chlorobenzoyl)-1,3,6-Trihydro-6-Aza-3-Oxapentalen-2-One (A) 1-benzyl-5-(p-chlorobenzoyl)-pyrrole-2-acetonitrile A solution of 8.43 ml. (0.0663 mole) of p-chlorobenzoyl chloride and 8.8 g. (0.0663 mole) of aluminum chloride in 100 ml. of 1,2-dichloroethane is added to a solution of 13.0 g. (0.0663 mole) of 1-benzylpyrrole-2-acetonitrile in 50 ml. of 1,2-dichloroethane at 5° C. over a 5 minute period. The mixture is stirred for 15 minutes, and then heated quickly to reflux for 3 minutes. The reaction mixture is poured into ice-hydrochloric acid and then filtered. The aqueous layer is separated and washed with chloroform. The combined organic solutions are washed successively with N,N-dimethylaminopropylamine solution, dilute hydrochloric acid, and brine and then dried over anhydrous magnesium sulfate. The solvent is evaporated and the oily residue dissolved in benzene-methylcyclohexane and seeded with crystals of 1-benzyl-4-(p-chlorobenzoyl)-pyrrole-2-acetonitrile. After crystallization of the latter substance is complete, the mother liquor is filtered and evaporated and the residue crystallized from methanol. The crystals thus obtained are recrystallized from methanol to give l-benzyl-5-(p-chlorobenzoyl)-pyrrole-2-acetonitrile as a yellow solid, m.p. 104–106° C.

(B) 1-benzyl-5-(p-chlorobenzoyl)-pyrrole-2-acetic acid

A suspension of 3.0 g. (0.009 mole) of 1-benzyl-5-(p-chlorobenzoyl)-pyrrole-2 -acetonitrile in 20 ml. of ethanol and 18 ml. (0.018 mole) of 1N sodium hydroxide is refluxed for 6 hours. The mixture is diluted with water, and the ethanol evaporated in vacuo. The solution is washed with chloroform and ether and acidified with 3N hydrochloric acid. The precipitated solid is collected and dried in vacuo to give 1-benzyl-5-(p-chlorobenzoyl)-pyrrole-2-acetic acid as white crystals, M.P. 162–163° C. Analysis: Calcd. for $C_{20}H_{15}ClNO_3$: C, 67.70; H, 4.65; N, 3.96%. Found: C, 67.79; H, 4.65; N, 3.97%.

(C) 6-benzyl-5-(4'-chlorobenzoyl)-1,3,6-trihydro-6-aza-3-oxapentalen-2-one 1-benzyl-5-(p-chlorobenzoyl)-pyrrole-2-acetic acid is subjected to the procedure of Example 1, part C to produce 6-benzyl-5-(4'-chlorobenzoyl)-1,3,6-trihydro-6-aza-3-oxapentalen-2-one ($R_1$=H, $R_2$=H, $R_3$=4'-chlorophenyl, $R_4$=phenyl, $R_5$=H, Y=CO, X=$CH_2$, m=1, n=1).

EXAMPLE 50

5-Benzoyl-6-Benzyl-1,3,6-Trihydro-6-Aza-3-Oxapentalen-2-One (A) 1-benzyl-5-benzoyl-pyrrole-2-acetonitrile The procedure of Example 49 is followed with an equivalent amount of benzoyl chloride in place of the p-chlorobenzoyl chloride used therein to yield 1-benzyl-5-benzoyl-pyrrole-2-acetonitrile.

(B) 1-benzyl-5-benzoyl-pyrrole-2-acetic acid

The nitrile-to-acid transformation procedure of Example 49B is followed using an equivalent amount of the acetonitrile obtained in part A of this Example to yield 1-benzyl-5-benzoyl-pyrrole-2-acetic acid.

(C) 5-benzoyl-6-benzyl-1,3,6-trihydro-6-aza-3-oxapentalen-2-one 1-benzyl-5-benzoyl-pyrrole-2-acetic acid is subjected to the procedure of Example 1, part C to produce 5-benzoyl-6-benzyl-1,3,6-trihydro-6-aza-3-oxapentalen-2-one ($R_1$=H, $R_2$=H, $R_3$=phenyl, $R_4$=phenyl, $R_5$=H, Y=CO, X=$CH_2$, m=1, n=1).

EXAMPLE 51

6-Benzyl-5-(4'-Bromobenzoyl)-1,3,6-Trihydro-6-Aza-3-Oxapentalen-2-One (A) 1-benzyl-5-(p-bromobenzoyl)-pyrrole-2-acetonitrile The procedure of Example 49 is followed with an equivalent amount of p-bromo benzoyl chloride in place of the p-chlorobenzoyl chloride used therein to yield 1-benzyl-5-(p-bromobenzoyl)-pyrrole-2-acetonitrile.

(B) 1-benzyl-5-(p-bromobenzoyl)-pyrrole-2-acetic acid

The nitrile-to-acid transformation procedure of Example 49B is followed using an equivalent amount of the acetonitrile obtained in part A of this Example to yield 1-benzyl-5-(p-bromobenzoyl)-pyrrole-2-acetic acid.

(C) 6-benzyl-5-(4'-bromobenzoyl)-1,3,6-trihydro-6-aza-3-oxapentalen-2-one 1-benzyl-5-(p-bromobenzoyl)-pyrrole-2-acetic acid is subjected to the procedure of Example 1, part C to produce 6-benzyl-5-(4'-bromobenzoyl)-1,3,6-trihydro-6-aza-3-oxapentalen-2-one ($R_1$=H, $R_2$=H, $R_3$=4'-bromophenyl, $R_4$=phenyl, $R_5$=H, Y=CO, X=$CH_2$, m=1, n=1).

EXAMPLE 52

6-Benzyl-5-(4'-Ethoxybenzoyl)-1,3,6-Trihydro-6-Aza-3-Oxapentalen-2-One (A) 1-benzyl-5-(p-ethoxybenzoyl)-pyrrole-2-acetonitrile The procedure of Example 49 is followed with an equivalent amount of p-ethoxy benzoyl chloride in place of the p-chlorobenzoyl chloride used therein to yield 1-benzyl-5 -(p-ethoxybenzoyl)-pyrrole-2-acetonitrile.

(B) 1-benzyl-5-(p-ethoxybenzoyl)-pyrrole-2-acetic acid

The nitrile-to-acid transformation procedure of Example 49B is followed using an equivalent amount of the acetonitrile obtained in part A of this Example to yield l-benzyl-5-(p-ethoxybenzoyl)-pyrrole-2-acetic acid.

(C) 6-benzyl-5-(4'-ethoxybenzoyl)-1,3,6-trihydro-6-aza-3-oxapentalen-2-one 1-benzyl-5-(p-ethoxybenzoyl)-pyrrole-2-acetic acid is subjected to the procedure of Example 1, part C to produce 6-benzyl-5-(4'-ethoxybenzoyl)-1,3,6-trihydro-6-aza-3-oxapentalen-2-one ($R_1$=H, $R_2$=H, $R_3$=4'-ethoxyphenyl, $R_4$=phenyl, $R_5$=H, Y=CO, X=$CH_2$, m=1, n=1).

EXAMPLE 53

6-Benzyl-5-(2',4'-Dichlorobenzoyl)-1,3,6-Trihydro-6-Aza-3-Oxapentalen-2-One (A) 1-benzyl-5-(2',4'-dichlorobenzoyl)-pyrrole-2-acetonitrile The procedure of Example 49 is followed with an equivalent amount of 2',4'-dichlorobenzoyl chloride in place of the p-chlorobenzoyl chloride used therein to yield 1-benzyl-5-(2',4'-dichlorobenzoyl)-pyrrole-2-acetonitrile.

(B) 1-benzyl-5-(2',4'-dichlorobenzoyl)-pyrrole-2-acetic acid

The nitrile-to-acid transformation procedure of Example 49B is followed using an equivalent amount of the acetonitrile obtained in part A of this Example to yield 1-benzyl-5-(2',4'-dichlorobenzoyl)-pyrrole-2-acetic acid.

(C) 6-benzyl-5-(2',4'-dichlorobenzoyl)-1,3,6-trihydro-6-aza-3-oxapentalen-2-one 1-benzyl-5-(2',4'-dichlorobenzoyl)-pyrrole-2-acetic acid is subjected to the procedure of Example 1, part C to produce 6-benzyl-5-(2',4'-dichlorobenzoyl)-1,3,6-trihydro-6-aza-3-oxapentalen-2-one ($R_1$=H, $R_2$=H, $R_3$=2',4'-dichlorophenyl, $R_4$=phenyl, $R_5$=H, Y=CO, X=$CH_2$, m=1, n=1).

EXAMPLE 54

6-Benzyl-5-(3',4'-Dimethylbenzoyl)-1,3,6-Trihydro-6-Aza-3-Oxapentalen-2-One (A) 1-benzyl-5-(3',4'-dimethylbenzoyl)-pyrrole-2-acetonitrile The procedure of Example 49 is followed with an equivalent amount of 3',4'-dimethylbenzoyl chloride in place of the p-chlorobenzoyl chloride used therein to yield 1-benzyl-5-(3',4'-dimethylbenzoyl)-pyrrole-2-acetonitrile.

(B) 1-benzyl-5-(3',4'-dimethylbenzoyl)-pyrrole-2-acetic acid

The nitrile-to-acid transformation procedure of Example 49B is followed using an equivalent amount of the acetonitrile obtained in part A of this Example to yield 1-benzyl-5-(3',4'-dimethylbenzoyl)-pyrrole-2-acetic acid.

(C) 6-benzyl-5-(3',4'-dimethylbenzoyl)-1,3,6-trihydro-6-aza-3-oxapentalen-2-one 1-benzyl-5-(3',4'-dimethylbenzoyl)-pyrrole-2-acetic acid is subjected to the procedure of Example 1, part C to produce 6-benzyl-5-(3',4'-dimethylbenzoyl)-1,3,6-trihydro-6-aza-3-oxapentalen-2-one ($R_1$=H, $R_2$=H, $R_3$=3',4'-dimethylphenyl, $R_4$=phenyl, $R_5$=H, Y=CO, X=$CH_2$,m=1,n=1).

EXAMPLE 55

Rac-1-Methyl-6-Benzyl-5-(4'-Chlorobenzoyl)-1,3,6-Trihydro-6-Aza-3-Oxapentalen-2-One (A) 1-benzyl-5-(p-chlorobenzoyl)-α-methyl-pyrrole-2-acetic acid The alkylation and transformation procedures of Examples 22C and 22D, respectively, are repeated, except that an equivalent amount of 1-benzyl-5-(4'-chlorobenzoyl)-pyrrole-2-acetonitrile and an equivalent amount of methyl halide as the alkylating agent are used to yield 1-benzyl-5-(p-chlorobenzoyl)-α-methyl-pyrrole-2-acetic acid.

(B) rac-1-methyl-6-benzyl-5-(4'-chlorobenzoyl)-1,3,6-trihydro-6-aza-3-oxapentalen-2-one 1-Benzyl-5-(p-chlorobenzoyl)-α-methyl-pyrrole-2-acetic acid is subjected to the procedure of Example 1, part C to produce rac-1-methyl-6-benzyl-5-(4'-chlorobenzoyl)-1,3,6-trihydro-6-aza-3-oxapentalen-2-one ($R_1$=methyl, $R_2$=H, $R_3$=4'-chlorophenyl, $R_4$=phenyl, $R_5$=H, Y=CO, X=$CH_2$, m=1, n=1).

EXAMPLE 56

Rac-1-(n-Propyl)-6-Benzyl-5-Benzoyl-1,3,6-Trihydro-6-Aza-3-Oxapentalen-2-One (A) 1-benzyl-5-benzoyl-α-(n-propyl)-pyrrole-2-acetic acid The alkylation and transformation procedures of Examples 22C and 22D, respectively, are repeated, except that an equivalent amount of 1-benzyl-5-benzoyl-pyrrole-2-acetonitrile and an equivalent amount of n-propyl halide as the alkylating agent are used to yield 1-benzyl-5-benzoyl-α-(n-propyl)-pyrrole-2-acetic acid.

(B) rac-1-(n-propyl)-6-benzyl-5-benzoyl-1,3,6-trihydro-6-aza-3-oxapentalen-2-one 1-Benzyl-5-benzoyl-α-(n-propyl)-pyrrole-2-acetic acid is subjected to the procedure of Example 1, part C to produce rac-1-(n-propyl)-6-benzyl-5-benzoyl-1,3,6-trihydro-6-aza-3-oxapentalen-2-one ($R_1$=n-propyl, $R_2$=H, $R_3$=phenyl, $R_4$=phenyl, $R_5$=H, Y=CO, X=$CH_2$, m=1, n=1).

EXAMPLE 57

Rac-1-Ethyl-6-Benzyl-5-(4'-Bromobenzoyl)-1,3,6-Trihydro-6-Aza-3-Oxapentalen-2-One (A) 1-Benzyl-5-(p-bromobenzoyl)-α-ethyl-pyrrole-2-acetic acid The alkylation and transformation procedures of Examples 22C and 22D, respectively, are repeated, except that an equivalent amount of 1-benzyl-5-(4'-bromobenzoyl)-pyrrole-2-acetonitrile and an equivalent amount of ethyl halide as the alkylating agent are used to yield 1-benzyl-5-(p-bromobenzoyl)-α-ethyl-pyrrole-2-acetic acid.

(B) rac-1-ethyl-6-benzyl-5-(4'-bromobenzoyl)-1,3,6-trihydro-6-aza-3 -oxapentalen-2-one 1-Benzyl-5-(p-bromobenzoyl)-α-ethyl-pyrrole-2-acetic acid is subjected to the procedure of Example 1, part C to produce rac-1-ethyl-6-benzyl-5-(4'-bromobenzoyl)-1,3,6-trihydro-6-aza-3-oxapentalen-2-one ($R_1$=ethyl, $R_2$=H, $R_3$=4'-bromophenyl, $R_4$=phenyl, $R_5$=H, Y=CO, X=$CH_2$, m=1, n=1).

EXAMPLE 58

Rac-1-Methyl-6-Benzyl-5-(4'-Ethoxybenzoyl)-1,3,6-Trihydro-6-Aza-3-Oxapentalen-2-One (A) 1-Benzyl-5-(p-ethoxybenzoyl)-α-methyl-pyrrole-2-acetic acid The alkylation and transformation procedures of Examples 22C and 22D, respectively, are repeated, except that an equivalent amount of 1-benzyl-5-(4'-ethoxybenzoyl)-pyrrole-2-acetonitrile and an equivalent amount of methyl halide as the alkylating agent are used to yield 1-benzyl-5-(p-ethoxybenzoyl)-α-methyl-pyrrole-2-acetic acid.

(B) rac-1-methyl-6-benzyl-5-(4'-ethoxybenzoyl)-1,3,6-trihydro-6-aza-3-oxapentalen-2-one 1-benzyl-5-(p-ethoxybenzoyl)-α-methyl-pyrrole-2-acetic acid is subjected to the procedure of Example 1, part C to produce rac-1-methyl-6-benzyl-5-(4'-ethoxybenzoyl)-1,3,6-trihydro-6-aza-3-oxapentalen-2-one ($R_1$=methyl, $R_2$=H, $R_3$=4'-ethoxyphenyl, phenyl, $R_5$=H, Y=CO, X=$CH_2$, m=1, n=1).

EXAMPLE 59

Rac-1-Ethyl-6-Benzyl-5-(2',4'-Dichlorobenzoyl)-1,3,6-Trihydro-6-Aza-3-Oxapentalen-2-One (A) 1-Benzyl-5-(2',4'-dichlorobenzoyl)-α-ethyl-pyrrole-2-acetic acid The alkylation and transformation procedures of Examples 22C and 22D, respectively, are repeated, except that an equivalent amount of 1-benzyl-5-(2',4'-dichlorobenzoyl)-pyrrole-2-acetonitrile and an equivalent amount of ethyl halide as the alkylating agent are used to yield 1-benzyl-5-(2',4'-dichlorobenzoyl)-α-ethyl-pyrrole-2-acetic acid (B) rac-1-ethyl-6-benzyl-5-(2',4'-dichlorobenzoyl)-1,3,6-trihydro-6-aza-3 -oxapentalen-2-one 1-Benzyl-5-(2',4'-dichlorobenzoyl)-α-ethyl-pyrrole-2-acetic acid is subjected to the procedure of Example 1, part C to produce rac-1-ethyl-6-benzyl-5-(2',4'-dichlorobenzoyl)-1,3,6-trihydro-6-aza-3-oxapentalen-2-one ($R_1$=ethyl, $R_2$=H, $R_3$=2',4'-dichlorophenyl, $R_4$=phenyl, $R_5$=H, Y=CO, X=$CH_2$, m=1, n=1).

EXAMPLE 60

Rac-1-Methyl-6-Benzyl-5-(3',4'-Dimethylbenzoyl)-1,3,6-Trihydro-6-Aza-3-Oxapentalen-2-One (A) 1-Benzyl-5-(3',4'-dimethylbenzoyl)-α-methyl-pyrrole-2-acetic acid The alkylation and transformation procedures of Examples 22C and 22D, respectively, are repeated, except that an equivalent amount of 1-benzyl-5-(3',4'-dimethylbenzoyl)-pyrrole-2-acetonitrile and an equivalent amount of methyl halide as the alkylating agent are used to yield 1-benzyl-5-(3',4'-dimethylbenzoyl)-α-methyl-pyrrole-2 -acetic acid.

(B) rac-1-Methyl-6-benzyl-5-(3',4'-dimethylbenzoyl)-1,3,6-trihydro-6-aza-3 -oxapentalen-2-one 1-Benzyl-5-(3',4'-dimethylbenzoyl)-α-methyl-pyrrole-2-acetic acid is subjected to the procedure of Example 1, part C to produce rac-1-methyl-6-benzyl-5-(3',4'-dimethylbenzoyl)-1,3,6-trihydro-6-aza-3-oxapentalen-2-one $R_1$=methyl, $R_2$=H, $R_3$=3',4'-dimethylphenyl, $R_4$=phenyl, $R_5$=H, Y=CO, X=$CH_2$, M=1, n=1

EXAMPLE 61

6-Methyl-5-(4'-Chlorobenzoyl)-1,3,6-Trihydro-6-Aza-3-Oxapentalen-2-One (A) 5-(p-chlorobenzoyl)-1-methylpyrrole-2-acetonitrile An acylating solution is prepared by the slow addition of 278 g. (1.58 moles) of p-chlorobenzoyl chloride to 210 g. (1.58 moles) of aluminum chloride in 750 ml. of ethylene chloride. The resulting solution is added to a solution of 190 g. (1.58 moles) of N-methylpyrrole-2-acetonitrile in 750 ml. of ethylene chloride. The temperature is maintained at 20–22° C. during the addition; and the solution is further stirred at room temperature for one hour. The solution is then heated rapidly to 74–76° C. at which point there is a vigorous evolution of hydrogen chloride gas. This temperature is maintained about 5 minutes, and the solution is cooled rapidly and poured into ice water. The product is extracted with methylene chloride and washed with water. The organic solution is then shaken with an excess of an aqueous solution of N,N-dimethylaminopropylamine followed by dilute hydrochloric acid to remove any excess p-chlorobenzoyl chloride. After a final wash with brine, the solution is dried over anhydrous magnesium sulfate. Distillation of the solvent leaves a residue which crystallizes. Recrystallization from methyl alcohol yields the product, 5-(p-chlorobenzoyl)-1 -methylpyrrole-2-acetonitrile, m.p. 120–124° C. After two additional recrystallizations from methanol, the m.p. is 127–131° C.

(B) 5-(p-Chlorobenzoyl)-1-methylpyrrole-2-acetic acid

A mixture of 129 g. (0.52 mole) of 5-(p-chlorobenzoyl)-1-methylpyrrole-2 -acetonitrile and 88 g. (1.1 moles) of 50% sodium hydroxide solution in 800 ml. of ethanol and 500 ml. of water is stirred and refluxed for about 18 hours with slow evolution of ammonia. The solution is then cooled to about 50° C. and acidified by adding 110 ml. of concentrated hydrochloric acid. The mixture is cooled, and the precipitated product, 5 -(p-chlorobenzoyl)-1-methylpyrrole-2-acetic acid, is filtered and recrystallized from methanol, m.p. 193–195° C. (dec.). A second crop is obtained upon concentration of the mother liquor for a total yield of about 67% of theoretical. Analysis: Calcd. for $C_{14}H_{11}ClNO_3$: N, 5.05%. Found: N, 5.06%.

(C) 6-Methyl-5-(4'-chlorobenzoyl)-1,3,6-trihydro-6-aza-3-oxapentalen-2-one 5-(p-Chlorobenzoyl)-1-methylpyrrole-2-acetic acid is subjected to the procedure of Example 1, part C to produce 6-methyl-5-(4'-chlorobenzoyl)-1,3,6-trihydro-6-aza-3 -oxapentalen-2-one ($R_1$=H, $R_2$=H, $R_3$=4'-chlorophenyl, $R_4$=methyl, $R_5$=H, Y=CO, M=1, n 0).

EXAMPLE 62

4-Methyl-5-Benzoyl-1,3,6-Trihydro-6-Aza-3-Oxapentalen-2-One (A) 1-Phenyl-1,2,3-butanetrione-2-oxime The procedure described by Ceresole in Ber., 17, 815 (1884), wherein 1-aryl-1,3 -butanediones are reacted with nitrous acid to yield the corresponding 1-aryl-1,2,3-butanetrione-2-oximes, is followed to prepare 1-phcnyl-1,2,3-butanetrione-2-oxime, m.p. 130–131° C.

(B) Ethyl 5-benzoyl-3-ethoxycarbonyl-4-methylpyrrole-2-acetate

A solution of 71 g. (0.37 mole) of 1-phenyl-1,2,3-butanetrione-2-oxime in 350 ml. glacial acetic acid and 50 ml. of water is added to 75.5 g. diethyl acetonedicarboxylate in 350 ml. of glacial acetic acid at 70° C. Concurrently, a mixture of 73 g. (1.12 mole) of zinc dust and 91.5 g. (1.12 mole) of anhydrous sodium acetate is added in portions at such a rate that the temperature is maintained near 100° C. After the additions are complete (about 45 minutes), the mixture is refluxed for one hour and poured into iced water. The resulting crude semisolid is collected by filtration and recrystallized twice from methanol to give ethyl 5-benzoyl-3-ethoxycarbonyl-4-methylpyrrole-2-acetate, m.p.

152–154° C. Analysis: Calcd. for $C_{19}H_{21}NO_5$: C, 66.46; H, 6.16; N, 4.08%. Found: C, 66.50; H, 6.20; N, 4.17%.

(C) 5-Benzoyl-3-carboxy-4-methylpyrrole-2-acetic acid

A mixture of 3.4 g. of ethyl 5-benzoyl-3-ethoxy-carbonyl-4-methylpyrrole-2-acetate, 10 g. of 50% sodium hydroxide solution and 10 ml. of water is refluxed for 2 hours. The reaction mixture is then diluted with water and acidified with dilute hydrochloric acid. The precipitated solid is collected by filtration, air-dried, and recrystallized from acetone-water to yield the product, 5-benzoyl-3-carboxy-4-methylpyrrole-2-acetic acid, as white crystals, m.p. 250–253° C.

(C) Ethyl 5-benzoyl-3-carboxy-4-methylpyrrole-2-acetate

A solution of 8.0 g. (0.028 mole) of 5-benzoyl-3-carboxy-4-methylpyrrole-2-acetic acid in 80 ml. of 0.5% ethanolic hydrogen chloride is refluxed for 90 minutes. The solution is charcoaled, filtered, and the filtrate evaporated in vacuo to yield a crystalline residue which is recrystallized from acetone to give ethyl 5-benzoyl-3-carboxy-4-methylpyrrole-2-acetate, m.p. 183–185° C.

(E) 5-Benzoyl-4-methylpyrrole-2-acetic acid

A solution of 4.13 g. (0.0131 mole) of ethyl 5-benzoyl-3-carboxy-4-methyl-pyrrole-2 -acetate in 80 ml. of quinoline in the presence of a trace amount of copper chromite is heated at 180–183° C. for 5 hours. The mixture is poured into dilute hydrochloric acid and extracted three times with ether. The ether extracts are combined and washed successively with dilute hydrochloric acid, sodium bicarbonate solution and brine and then dried over anhydrous magnesium sulfate. The solvent is evaporated in vacuo to give about 4 g. of semisolid ethyl 5-benzoyl-4-methylpyrrole-2-acetate which is used in the following hydrolysis procedure without further purification. The entire semisolid is dissolved in 20 ml. of ethanol and 20 ml. of 1N sodium hydroxide solution is added. The mixture is heated under reflux for 30 minutes. The solvent is then evaporated in vacuo, and the residue dissolved in water and washed with ether. The aqueous solution is acidified with dilute hydrochloric acid and the resulting crystalline solid (1.6 g., 50% yield) is collected by filtration and air-dried. The product, 5-benzoyl-4-methylpyrrole-2-acetic acid is recrystallized three times from acetone-water with charcoaling, m.p. 167–168° C.

(F) BOC-5-benzoyl-4-methylpyrrole-2-acetic acid

The procedure of Example 1, part C is repeated using 5-benzoyl-4-methylpyrrole-2 -acetic acid to give BOC-5-benzoyl-4-methylpyrrole-2-acetic acid.

(G) BOC 4-methyl-5-benzoyl-1,3,6-trihydro-6-aza-3-oxapentalen-2-one

The procedure of Example 33C is repeated using BOC-5-benzoyl-4-methylpyrrole-2 -acetic acid to give BOC 4-methyl-5-benzoyl-1,3,6-trihydro-6-aza-3-oxapentalen-2-one.

(H) 4-Methyl-5-benzoyl-1,3,6-trihydro-6-aza-3-oxapentalen-2-one

The procedure of Example 33E is repeated using BOC 4-methyl-5-benzoyl-1,3,6 -trihydro-6-aza-3-oxapentalen-2-one to give 4-methyl-5-benzoyl-1,3,6-trihydro-6-aza-3-oxapentalen-2-one ($R_1$=H, $R_2$=H, $R_3$=phenyl, $R_4$=H, $R_5$=methyl, Y=CO, m=1, n=0).

EXAMPLE 63

4-Methyl-5-(4'-Chlorobenzoyl)-1,3,6-Trihydro-6-Aza-3-Oxapentalen-2-One (A) 1-(p-Chlorophenyl)-1,2,3-butanetrione-2-oxime The procedure described by Ceresole in Ber., 17, 815 (1884), wherein 1-aryl-1,3 -butanedion is reacted with nitrous acid to yield the corresponding 1-aryl-1,2,3-butanctrione-2-oxime, is followed to prepare 1-(p-chlorophenyl)-1,2,3-butanetrione-2-oxime.

(B) Ethyl-5-(p-chlorobenzyl)-3-ethoxycarbonyl-4-methyl-pyrrole-2-acetate

By repeating the procedure of Example 62, part B with an equivalent amount of 1 -(p-chlorophenyl)-1,2,3-butanetrione-2-oxime, ethyl-5-(p-chlorobenzyl)-3-ethoxycarbonyl-4 -methylpyrrole-2-acetate is obtained.

(C) 5-(p-Chlorobenzoyl)-3-carboxy-4-methylpyrrole-2-acetic acid

The hydrolysis procedure of Example 62, part C is repeated, except that an equivalent amount of the ester obtained in part B of this Example is used to yield 5-(p-chlorobenzoyl)-3 -carboxy-4-methylpyrrole-2-acetic acid.

(D) Ethyl 5-(p-chlorobenzoyl)-3-carboxy-4-methylpyrrole-2-acetate

The partial reesterification procedure in Example 62 D above is repeated using an equivalent amount of the acid obtained in part C of this Example to yield ethyl 5 -(p-chlorobenzoyl)-3-carboxy-4-methylpyrrole-2-acetate.

(E) 5-(p-Chlorobenzoyl)-3-carboxy-4-methylpyrrole-2-acetic acid

The procedure of Example 62, part E is repeated using an equivalent amount of the ester obtained in part D of this Example to yield 5-(p-chlorobenzoyl)-4-methylpyrrole-2-acetic acid.

(F) BOC 5-(p-chlorobenzoyl)-4-methylpyrrole-2-acetic acid

The procedure of Example 33C is repeated using 5-(p-chlorobenzoyl)-4 -methylpyrrole-2-acetic acid to give BOC 5-(p-chlorobenzoyl)-4-methylpyrrole-2-acetic acid.

(G) BOC 4-methyl-5-(4'-chlorobenzoyl)-1,3,6-trihydro-6-aza-3 oxapentalen-2-one

BOC 5-(p-chlorobenzoyl)-4-methylpyrrole-2-acetic acid is subjected to the procedure of Example 1, part C to produce BOC 4-methyl-5-(4'-chlorobenzoyl)-1,3,6-trihydro-6-aza-3-oxapentalen-2-one.

(H) 4-methyl-5-(4'-chlorobenzoyl)-1,3,6-trihydro-6-aza-3 oxapentalen-2-one

The procedure of Example 33E is repeated using BOC 4-methyl-5-(4'-chlorobenzoyl)-1,3,6-trihydro-6-aza-3-oxapentalen-2-one to produce 4-methyl-5-(4'-chlorobenzoyl)-1,3,6-trihydro-6-aza-3-oxapentalen-2-one ($R_1$=H, $R_2$=H, $R_3$=4'-chlorophenyl, $R_4$=H, $R_5$=methyl, Y=CO, m=1, n=0).

EXAMPLE 64

4-Methyl-5-(4'-Methylbenzoyl)-1,3,6-Trihydro-6-Aza-3-Oxapentalen-2-One (A) 1-(p-Methylphenyl)-1,2,3-butanetrione-2-oxime The procedure described by Ceresole in Ber., 17, 815 (1884), wherein 1-aryl-1,3 -butanediones are reacted with nitrous acid to yield the corresponding 1-aryl-1,2,3-butanetrione-2-oximes, is followed to prepare 1-(p-methylphenyl)-1,2,3-butanetrione-2 -oxime.

(B) Ethyl 5-(p-methylbenzoyl)-3-ethoxycarbonyl-4-methylpyrrole-2-acetate

By repeating the procedure of Example 62, part B with an equivalent amount of 1-(p-methylphenyl)-1,2,3-butanetrione-2-oxime, ethyl 5-(p-methylbenzoyl)-3-ethoxycarbonyl-4-methylpyrrole-2-acetate is obtained.

(C) Ethyl-5-(p-methylbenzoyl)-3-carboxy-4-methylpyrrole-2-acetic acid

The hydrolysis procedure of Example 62, part C is repeated, except that an equivalent amount of the ester obtained in part B of this Example is used to yield ethyl 5-(p-methylbenzoyl)-3-carboxy-4-methylpyrrole-2-acetic acid.

(D) Ethyl 5-(p-methylbenzoyl)-3-carboxy-4-methylpyrrole-2-acetate

The partial reesterification procedure in Example 62 D above is repeated using an equivalent amount of the acid obtained in part C of this Example to yield ethyl 5-(p-methylbenzoyl)-3-carboxy-4-methylpyrrole-2-acetate.

(E) 5-(p-methylbenzoyl)-4-methylpyrrole-2-acetic acid

The procedure of Example 62, part E is repeated using an equivalent amount of the ester obtained in part D of this Example to yield 5-(p-methylbenzoyl)-4-methylpyrrole-2-acetic acid.

(F) BOC 5-(p-methylbenzoyl)-4-methylpyrrole-2-acetic acid

The procedure of Example 33C is repeated using 5-(p-methylbenzoyl)-4-methylpyrrole-2-acetic acid to produce BOC 5-(p-methylbenzoyl)-4-methylpyrrole-2-acetic acid.

(G) BOC 4-Methyl-5-(4'-methylbenzoyl)-1,3,6-trihydro-6-aza-3-oxapentalen-2-one

BOC 5-(p-methylbenzoyl)-4-methylpyrrole-2-acetic acid is subjected to the procedure of Example 1, part C to produce BOC 4-methyl-5-(4'-methylbenzoyl)-1,3,6-trihydro-6-aza-3-oxapentalen-2-one.

(G) 4-Methyl-5-(4'-methylbenzoyl)-1,3,6-trihydro-6-aza-3-oxapentalen-2-one

The procedure of Example 33E is repeated using BOC 4-methyl-5-(4'-methylbenzoyl)-1,3,6-trihydro-6-aza-3-oxapentalen-2-one to give 4-methyl-5-(4'-methylbenzoyl)-1,3,6-trihydro-6-aza-3-oxapentalen-2-one ($R_1$=H, $R_2$ H, $R_3$=4'-methylphenyl, $R_4$=H, $R_5$=methyl, Y=CO, m=1, n=0).

EXAMPLE 65

4-Methyl-5-(4'-Methoxybenzoyl)-1,3,6-Trihydro-6-Aza-3-Oxapentalen-2-One (A) 1-(p-Methoxyphenyl)-1,2,3-butanetrione-2-oxime The procedure described by Ceresole in Ber., 17, 815 (1884), wherein 1-aryl-1,3-butanediones are reacted with nitrous acid to yield the corresponding 1-aryl-1,2,3-butanetrione-2-oximes, is followed to prepare 1-(p-methoxyphenyl)-1,2,3-butanetrione-2-oxime.

(B) Ethyl 5-(p-methoxybenzoyl)-3-ethoxycarbonyl-4-methylpyrrole-2-acetate

By repeating the procedure of Example 62, part B with an equivalent amount of 1-(p-methoxyphenyl)-1,2,3-butanctrione-2-oxime, ethyl 5-(p-methoxybenzoyl)-3-ethoxycarbonyl-4-methylpyrrole-2-acetate is obtained.

(C) Ethyl 5-(p-methoybenzoyl)-3-carboxy-4-methylpyrrole-2-acetate

The hydrolysis procedure of Example 62, part C is repeated, except that an equivalent amount of the ester obtained in part B of this Example is used to yield ethyl 5-(p-methoxybenzoyl)-3-carboxy-4-methylpyrrole-2-acetate.

(D) Ethyl 5-(p-methoxybenzoyl)-3-carboxy-4-methylpyrrole-2-acetate.

The partial reesterification procedure in Example 62 D above is repeated using an equivalent amount of the acid obtained in part C of this Example to yield ethyl 5-(p-methoxybenzoyl)-3-carboxy-4-methylpyrrole-2-acetate.

(E) 5-(p-methoxybenzoyl)-4-methylpyrrole-2-acetic acid

The procedure of Example 62, part E is repeated using an equivalent amount of the ester obtained in part D of this Example to yield 5-(p-methoxybenzoyl)-4-methylpyrrole-2-acetic acid.

(F) BOC 5-(p-methoxybenzoyl)-4-methylpyrrole-2-acetic acid

The procedure of Example 33C is repeated using 5-(p-methoxybenzoyl)-4-methylpyrrole-2-acetic acid to produce BOC 5-(p-methoxybenzoyl)-4-methylpyrrole-2-acetic acid.

(G) BOC 4-methyl-5-(4'-methoxybenzoyl)-1,3,6-trihydro-6-aza-3-oxapentalen-2-one

BOC 5-(p-methoxybenzoyl)-4-methylpyrrole-2-acetic acid is subjected to the procedure of Example 1, part C to produce BOC 4-methyl-5-(4'-methoxybenzoyl)-1,3,6-trihydro-6-aza-3-oxapentalen-2-one (H) 4-Methyl-5-(4'-methoxybenzoyl)-1,3,6-trihydro-6-aza-3-oxapentalen-2-one The procedure of Example 33E is repeated using BOC 4-methyl-5-(4'-methoxybenzoyl)-1,3,6-trihydro-6-aza-3-oxapentalen-2-one to give 4-methyl-5-(4'-methoxybenzoyl)-1,3,6-trihydro-6-aza-3-oxapentalen-2-one ($R_1$=H, $R_2$=H, $R_3$=4'-methoxyphenyl, $R_4$=H, $R_5$=methyl, Y=CO, m=1, n=0).

EXAMPLE 66

6-Benzyl-5-(4'-Chlorobenzoyl)-1,3,6-Trihydro-6-Aza-3-Oxapentalen-2-One (A) 2-Dimethylaminomethyl-1-benzylpyrrole A solution of 8.2 g. (0.1 mole) dimethylamine hydrochloride in 8 ml. formalin is added dropwise to 17.12 g. (0.1 mole) of 1-benzylpyrrole. The mixture is stirred at room temperature until solution occurs (about 4 hours). The solution is poured into 10% sodium hydroxide solution and then extracted into ether three times. The combined organic fractions are washed with a saturated solution of sodium chloride, dried over magnesium sulfate and the solvent evaporated in vacuo. The product, 2-dimethylaminomethyl-1-benzylpyrrole, is distilled at reduced pressure, b.p. 73° C., 0.025 mm. Hg.

(B) 2-Dimethylaminomethyl-1-benzylpyrrole methiodide

A solution of 100 g. (0.47 mole) of 2-dimethylaminomethyl-1-benzylpyrrole in 200 ml. of absolute ethanol is cooled to 5° C. To this is added dropwise 29.4 ml. (0.47 mole) of methyl iodide. A white solid precipitates. The suspension is stirred until the precipitate is so thick that additional stirring becomes impossible. The solid, 2-dimethylaminomethyl-1-benzylpyrrole methiodide, is filtered off and dried in vacuum.

(C) 1-Benzylpyrrole-2-acetonitrile

A suspension of 88.9 g. (0.25 mole) of 2-dimethylaminomethyl-1-benzylpyrrole methiodide is added to a suspension of 12.8 g. (0.26 mole) of sodium cyanide in 40 ml. dimethylsulfoxide. The mixture is heated under reflux for 3 hours, and stirring at room temperature is continued overnight. The reaction mixture is poured into water and extracted three times with ether. The combined ether extracts are washed with brine and dried over anhydrous magnesium sulfate. The ether solvent is evaporated in vacuo to give an oily residue which crystallizes upon standing. Recrystallization from methylcyclohexane yields the product, 1-benzylpyrrole-2-acetonitrile, m.p. 62–63° C.

(D) 1-Benzyl-5-(p-chlorobenzoyl)-pyrrole-2-acetonitrile

A solution of 8.43 ml. (0.067 mole) of p-chlorobenzoyl chloride and 8.8 g. (0.067 mole) of aluminum chloride in 100 ml. of 1,2-dichloroethane is added to a solution of 13.0 g. (0.067 mole) of 1-benzylpyrrole-2acetonitrile in 50 ml. of 1,2-dichloroethane at 5° C. over a 5 minute period. The reaction mixture is stirred for 15 minutes and then heated quickly to reflux for 3 minutes. The mixture is poured into ice-hydrochloric acid and then filtered. The aqueous layer is separated and washed with chloroform. The combined organic fractions are washed successively with N,N-dimetylaminopropylamine solution, dilute hydrochloric acid and brine and then dried over anhydrous magnesium sulfate. The solvent is evaporated to yield an oily residue from which the desired compound is isolated by column chromatography on neutral alumina with a 50—50 mixture of benzene ether as the eluting solvent. Evaporation of the elute affords 1-benzyl-5-(p-chlorobenzoyl)-pyrrole-2-acetonitrile as a yellow solid which is recrystallized from methanol, m.p. 106–108° C.

(E) 1-Benzyl-5-(p-chlorobenzoyl)-pyrrole-2-acetic acid

The nitrile-to-acid transformation procedure of Example 49B is followed using an equivalent amount of the acetonitrile obtained in Part D of this example to yield 1-benzyl-5-(p-chlorobenzoyl)-pyrrole-2-acetic acid.

(F) 6-Benzyl-5-(4'-chlorobenzoyl)-1,3,6-trihydro-6-aza-3-oxapentalen-2-one

1-Benzyl-5-(p-chlorobenzoyl)-pyrrole-2-acetic acid is subjected to the procedure of Example 1, Part C to produce 6-benzyl-5-(4'-chlorobenzoyl)-1,3,6-trihydro-6-aza-3-oxapentalen-2-one ($R_1$=H, $R_2$=H, $R_3$=4'-chlorophenyl, $R_4$=phenyl, $R_5$=H, Y=CO, X=$CH_2$, m=1, n=1).

EXAMPLE 67

6-Methyl-5-(4'-Isopropylbenzoyl)-1,3,6-Trihydro-6-Aza-3-Oxapentalen-2-One (A) 5-(p-Isopropylbenzoyl)-1-methylpyrrole-2-acetonitrile To a suspension of 17.5 g. (0.131 mole) aluminum chloride in 60 ml. 1,2 -dichloroethane is added 24 g (0.131 mole) p-isopropylbenzoyl chloride. The resulting mixture is added slowly and dropwise to a chilled solution (0° C.) of 15.7 g. (0.131 mole) 1 -methylpyrrole-2-acetonitrile in 1 00 ml. of 1,2-dichloroethane. After the addition is complete, the mixture is stirred at room temperature for twenty minutes and heated at reflux for three minutes. The reaction mixture is then cooled and poured into ice-dilute hydrochloric acid. The organic phase is separated and washed successively with N,N-dimethyl-1,3 -propanediamine, dilute hydrochloric acid and a saturated solution of sodium chloride; dried over magnesium sulfate; and the solvent evaporated. The product, 5-(p-isopropylbenzyl)-1 -methylpyrrole-2-acetonitrile, is isolated from the residual oil by column chromatography. The column is packed with acid washed alumina and eluted with benzene, ether and etylacetate. The product is found in the first compound-bearing fraction which absorbs ultraviolet light at approximately 250 μm. It is purified by recrystallization twice in ether: pentane. m.p. 59–64° C. Anal. Calcd. for $C_{17} H_{18} N_2$ O: N, 10.53%. Found: N,10.71%.

(B) 5-(p-isopropylbenzoyl)-1-methylpyrrole-2-acetic acid

A solution of 6.5 g. (0.024 mole) of 5-(p-isopropylbenzoyl)-1-methylpyrrole-2 -acetonitrile, 52 ml. 1N sodium hydroxide and 50 ml. 95% ethanol are heated at reflux overnight. The ethanol is then evaporated, and the remaining yellow solution is poured into ice-dilute hydrochloric acid. A precipitate forms which is separated by filtration and recrystallized in ether: hexane. The solid is then partitioned between sodium bicarbonate solution and ether. The sodium bicarbonate phase is separated and acidified with dilute hydrochloric acid. The white precipitate, 5-(p-isopropylbenzoyl)-1methylpyrrole-2-acetic acid, is filtered and dried in vacuo, m.p. 98–101° C. Anal. Calcd. for $C_{17} H_{19} NO_3$: N, 4.91%. Found: N, 5.14%.

(C) 6-Methyl-5-(4'-isopropylbenzoyl)-1,3,6-trihydro-6-aza-3-oxapentalen-2-one 5-(p-Isopropylbenzoyl)-1-methylpyrrole-2-acetic acid is subjected to the procedure of Example 1, part C to produce 6-methyl-5-(4'-isopropylbenzoyl)-1,3,6-trihydro-6-aza-3-oxapentalen-2-one ($R_1$=H, $R_2$=H, $R_3$=4'-isopropylphenyl, $R_4$=methyl, $R_5$=H, Y=CO, m=1,n=0).

EXAMPLE 68

6-Methyl-5-(2'-Toluoyl)-1,3,6-Trihydro-6-Aza-3-Oxapentalen-2-One (A) 1-methyl-5-(o-toluoyl)-pyrrole.-2-acetonitrile To a solution of 24 g. (0.20 mole) of 1-methylpyrrole-2-acetonitrile and 30.92 g. (0.20 mole) o-toluoyl chloride in 200 ml. methylene chloride (cooled externally to −20° C.) is added dropwise 23.4 ml. (0.20 mole) of stannic chloride. After the addition is complete, the yellow mixture is permitted to come to room temperature. The mixture is then poured into ice-dilute hydrochloric acid. The two phases are separated. The organic phase is washed consecutively with N,N-dimethyl-1,3-propanediamine, 3N hydrochloric acid, and saturated sodium chloride solution; dried over magnesium sulfate; and the product, 1-methyl-5-(o-toluoyl)-pyrrole-2 -acetonitrile, is separated from the residual oil by chromatography. The column is packed with acid washed alumina in hexane. The eluant is benzene. The product is found in the first compound bearing fraction as determined by ultraviolet absorption at 260 mμ. The benzene is evaporated and the resultant solid is purified by recrystallization twice from methanol, m.p. 90–92.5° C.

(B) 1-methyl-5-(o-toluoyl)-pyrrole-2-acetic acid

A solution of 10.6 g. (0.0445 mole) of 1-methyl-5-(o-toluoyl)-pyrrole-2-acetonitrile, 89 ml. 1N sodium hydroxide and 10 ml. 95% ethanol is heated at reflux for 18 hours, cooled and poured into dilute hydrochloric acid, and extracted with chloroform. The chloroform phase is separated and extracted with sodium bicarbonate solution. The product, 1-methyl-5 -(o-toluoyl)-pyrrole-2-acetic acid, is precipitated from the aqueous phase upon treatment with 3N hydrochloric acid, separated by filtration, and purified by recrystallization in isopropanol using charcoal while the solution is still warm, and subsequent recrystallization with methanol, m.p. 133–135° C. Anal. Calcd. for $C_{15}H_{15}NO_3$ : C, 70.02; H, 5.88; N, 5.44%. Found: C, 70.07; H, 5.97; N, 5.54%.

(C) 6-Methyl-5-(2'-toluoyl)-1,3,6-trihydro-6-aza-3-oxapentalen-2-one

1-Methyl-5-(o-toluoyl)-pyrrole-2-acetic acid is subjected to the procedure of Example 1, part C to produce 6-methyl-5-(2'-toluoyl)-1,3,6-trihydro-6-aza-3-oxapentalen-2-one ($R_1$=H, $R_2$=H, $R_3$=2'-methylphenyl, $R_4$=methyl, $R_5$=H, Y=CO, m=1, n=0)

EXAMPLE 69

6-Methyl-5-(2'-Thienoyl)-1,3,6-Trihydro-6-Aza-3-Oxapentalen-2-One (A) 1-Methyl-5-(2'-thienoyl)-pyrrole-2-acetonitrile A solution of 20.0 g. (0.15 mole) of aluminum chloride and 22.0 g. (0.15 mole) of thiophene-2-carboxylic acid chloride in 200 ml. 1,2-dichloroethane is added to a solution of 18.0 g. (0.15 mole) of 1-methyl-pyrrole-2-acetonitrile in 100 ml. of 1,2-dichloroethane at 5° C. over a period of 5 minutes. The mixture is stirred for 20 min. and then quickly heated to reflux for 3 minutes. It is poured into ice-hydrochloric acid. The organic layer is separated and the aqueous solution washed with 1,2-dichloroethane. The combined organic solutions are washed consecutively with water, N,N-dimethylaminopropylamine, dilute hydrochloric acid and brine. The solution is then dried over magnesium sulfate and the solvent evaporated in vacuo. The residue crystallizes to give a yellow solid which shows two spots on thin layer chromatography (1:1 ethyl acetate, cyclohexane on silica gel). The solid is dissolved in benzene and seeded with crystals of 1-methyl-5-(2'-thienoyl)-pyrrole-2-acetonitrile obtained by exhaustive crystallization from benzene. After crystallization, the supernatant liquid is decanted from the precipitated 1-methyl-5-(2'-thienoyl)-2-acetonitrile and evaporated. The thus-obtained solid is recrystallized from methanol and seeded with crystals of 1-methyl-5-(2'-thienoyl)-pyrrole-2-acetonitrile which were obtained by exhaustive crystallization of a another run from methanol. The mother liquor from the crystallization of the latter compound is evaporated and recycled through the same crystallization processes. After four cycles, there is obtained 1-methyl-5-(2'-thienoyl)-pyrrole-2-acetonitrile, m.p. 132–133° C.

(B) 1-Methyl-5-(2'-thienoyl)-pyrrole-2-acetic acid

A suspension of 7.35 g. (0.032 mole) of 1-methyl-5-(2'-thienoyl)-pyrrole-2 -acetonitrile in 30 ml. of 95% ethanol and 64 ml. (0.064 mole) of 1N sodium hydroxide solution is refluxed for 5 hours. The mixture is cooled, and the ethanol evaporated in vacuo. Water is added, and the solution is washed successively with methylene chloride and ether and clarified with charcoal. The solution is acidified with dilute hydrochloric acid and the precipitated solid, 1-methyl-5-(2'-thienoyl)-pyrrole-2-acetic acid, is collected and dried in vacuo, m.p. 140–142° C. It is recrystallized from methanol-water to give the product as a white solid, m.p. 141–142° C. Anal. Calcd, for $C_{12}H_{11}NO_3S$: C, 57.83; H, 4.45; H 5.62%. Found: C, 57.81; H, 4.44; N 5.68%.

(C) 6-Methyl-5-(2'-thienoyl)-1,3,6-trihydro-6-aza-3-oxapentalen-2-one

1-Methyl-5-(2'-thienoyl)-pyrrole-2-acetic acid is subjected to the procedure of Example 1, part C to produce 6-methyl-5-(2'-thienoyl)-1,3,6-trihydro-6-aza-3-oxapentalen-2 -one ($R_1$=H, $R_2$=H, $R_3$=2'-thiophenyl, $R_4$=methyl, $R_5$=H, Y=CO, m=1, n=0)

EXAMPLE 70

6-Methyl-5-(5'-Methyl-2'-Thienoyl)-1,3,6-Trihydro-6-Aza-3-Oxapentalen-2-One (A) 1-Methyl-5-(5'-methyl-2'-thienoyl)-pyrrole-2-acetonitrile To a suspension of 25.54 g. (0.019 mole) anhydrous aluminum chloride in 70 ml. of 1,2-dichlorocthane is added 30.7 g. (0.019 mole) 5-methyl-2-thienoyl chloride. The resulting solution is added dropwise to a chilled (0° C.) solution of 24 g. (0.02 mole) 1-methylpyrrole-2-acetonitrile. After the addition, the solution is stirred at room temperature for approximately 40 minutes, and then heated at reflux for 3 minutes and poured onto ice acidified with dilute hydrochloric acid. The two phases are separated. The organic phase is washed successively with N,N-dimethyl-1,3-propanediamine, 3N hydrochloric acid and saturated sodium chloride solution. It is then dried over magnesium sulfate and the solvent evaporated. The resulting solid, 1-methyl-5-(5'-methyl-2'-thienoyl)-pyrrole-2-acetonitrile, is separated by filtration and purified by washing in cold methanol and benzene, m.p. 118–121° C.

(B) 1-Methyl-5-(5'-methyl-2'-thienoyl)-pyrrole-2-acetic acid

A solution of 10.5 g. (0.043 mole) of 1-methyl-5-(5'-methyl-2'-thienoyl)-pyrrole-2 -acetonitrile, 86 ml. 1N sodium hydroxide and 50 ml. 95% ethanol is refluxed for 15 hours and then cooled and poured into 3N hydrochloric acid. The white precipitate, 1-methyl-5 -(5'-methyl-2'-thienoyl)-pyrrole-2-acetic acid, is collected by filtration, air dried, and recrystallized twice in acetonitrile, m.p. 152–154° C. Anal. Calcd. for $C_{13}H_{13}NO_3S$: C, 59.37; H, 4.98; N, 5.33. Found: C, 59.15; H, 4.99; N, 5.64.

(C) 6-Methyl-5-(5'-methyl-2'-thienoyl)-1,3,6-trihydro-6-aza-3-oxapentalen-2-one

1-Methyl-5-(5'-methyl-2'-thienoyl)-pyrrole-2-acetic acid is subjected to the procedure of Example 1, part C to produce 6-methyl-5-(5'methyl-2'-thienoyl)-1,3,6-trihydro-6-aza-3-oxapentalen-2-one ($R_1$=H, $R_2$=H, $R_3$=5'-methyl-2'-thiophenyl, $R_4$=methyl, $R_5$=H, Y=CO, m=1, n=0).

EXAMPLE 71

6-Methyl-5-(p-Trifluoromethylbenzoyl)-1,3,6-Trihydro-6-Aza-3-Oxapentalen-2-One (A) 1-methyl-5-(p-trifluoromethylbenzoyl)-pyrrole-2-acetonitrile A solution of 14.4 g. (0.12 mole) of 1-methylpyrrole-2-acetontrile and 25 g. (0.12 mole) of p-trifluoromethylbenzoyl chloride in 120 ml. methylene chloride is chilled to −25° C. (external bath). Then 14 ml. (0.12 mole) stannic chloride is added dropwise over a half hour. The resultant suspension is permitted to come to room temperature and poured into ice-dilute hydrochloric acid. The aqueous phase is separated and washed successively with N,N-dimethyl-1,3-propane-diamine, 3N hydrochloric acid and a saturated solution of sodium chloride. The solvent is evaporated, and the product is isolated from the residual oil by column chromatography using acid-washed alumina. The solvents hexane, benzene, and ether are used as eluents. The first compound-bearing fraction not giving a positive Enrlich's test (in benzene) is collected. The solvent is evaporated and the resultant solid, 1-methyl-5 -(p-trifluoromethylbenzoyl)-pyrrole-2-acetonitrile, in purified by recrystallization from isopropanol, m.p. 95–97.5° C.

(B) 1-Methyl-5-(p-trifluoromethylbenzoyl)-pyrrole-2-acetic acid

A solution of 2.2 g. (0.0075 mole) of 1-methyl-5-(p-trifluoromethylbenzoyl)-pyrrole-2 -acetonitrile, 15 ml. 95% ethanol and 15 ml. 1N sodium hydroxide is refluxed for 18 hours. The ethanol is evaporated. The resultant yellow solid is dissolved with water and poured into dilute hydrochloric acid. The resultant white precipitate 1-methyl-5 -(p-trifluoromethylbenzoyl)-pyrrole-2-acetic acid, is collected by filtration and purified by recrystallization from isopropanol, m.p. 152–154° C. Anal. Calcd. for $C_{15}H_{12}F_3NO_3$: C, 57.88; H, 3.89; N, 4.50%. Found: C, 57.92; H, 4.12; N, 4.38%.

(C) 6-Methyl-5-(p-tri fluoromethylbenzoyl)-1,3,6-trihydro-6-aza-3-oxapentalen-2 -one 1-Methyl-5-(p-trifluoromethylbenzoyl)-pyrrole-2-acetic acid is subjected to the procedure of Example 1, part C to produce 6-methyl-5-(p-trifluoromethylbenzoyl)-1,3, 6-trihydro-6-aza-3-oxapentalen-2-one ($R_1$=H, $R_2$=H, $R_3$=4'-trifluoromethylphenyl, $R_4$ =methyl, $R_5$=H, Y=CO, m=1, n=0).

EXAMPLE 72

4,6-Dimethyl-5-(p-Chlorobenzoyl)-1,3,6 -Trihydro-6-Aza-3-Oxapentalen-2-One (A) Ethyl 1,4-dimethyl-3-ethoxycarbonylpyrrole-2-acetate To a solution of 500 ml. of 25% aqueous methylamine is added 93 g. (0.46 mole) of diethyl acetone-dicarboxylate. To the mixture is added 72 g. (0.782 mole) of chloroacetone over a 10-minute period. The temperature is kept below 60° C. by external cooling. After 2 hours, the mixture is poured into ice-hydrochloric acid. The solid is collected by filtration, washed with water and air dried. It is recrystallized from hexane to give ethyl 1,4-dimethyl-3-ethoxycarbonylpyrrole-2-acetate as a white solid, m.p. 71–72° C. Anal. Calcd. for $C_{13}H_{19}NO_4$: C, 61.64; H, 7.56; N, 5.53%. Found: C, 61.64; H, 7.64; N, 5.71%.

(B) Ethyl 5-(p-chlorobenzoyl)-1,4 dimethyl-3-ethoxycarbonylpyrrole-2-acetate

A solution of 17.5 g. (0.1 mole) p-chlorobenzoyl chloride and 13.3 g. (0.1 mole) aluminum chloride in 150 ml. of dichloroethane is added rapidly to a solution of 25.3 g. (0.1 mole) of ethyl 1,4-dimethyl-3ethoxycarbonylpyrrole-2-acetate in 100 ml. of refluxing 1,2 -dichloroethane. The solution is refluxed for 3.5 hours and poured into ice-hydrochloric acid. The organic layer is separated, and the aqueous layer washed with 1,2-dichloroethane. The combined organics are washed successively with water, N,N-dimethylaminopropylamine, dilute HCl and brine. The solution is then dried over anhydrous magnesium sulfate and the solvent evaporated in vacuo. The residue product is crystallized from cyclohexane and recrystallized from methanol to give ethyl 5-(p-chlorobenzoyl)-1,4 dimethyl-3-ethoxycarbonylpyrrole-2-acetate as a white solid, m.p. 91–93° C.

(C) 5-(p-Chlorobenzoyl)-3-carboxy-1,4-dimethylpyrrole-2-acetic acid

A suspension of 17.3 g. (0.0435 mole) of ethyl 5-(p-chlorobenzoyl)-1,4 dimethyl-3 -ethoxypyrrole-2-acetate in 170 g. of 25% sodium hydroxide is heated under reflux for 3 hours. The suspension is poured into ice, and the resulting yellow solution is added to ice-hydrochloric acid with stirring. The precipitated solid is collected by filtration, air dried and recrystallized from acetone containing 10% water to give 5-(p-chlorobenzoyl)-3-carboxy-1,4-dimethylpyrrole-2-acetic acid as a white solid, m.p. 253–254° C.

(D) Ethyl 5-(p-chlorobenzoyl)-3-carboxy-1,4-dimethylpyrrole-2-acetate

A suspension of 2.0 g. of 5-(p-chlorobenzoyl)-3-carboxy-1,4-dimethylpyrrole-2-acetic acid in 20 ml. of 0.5% ethanolic hydrogen chloride is heated under reflux. The solid gradually dissolves. After 40 minutes, a white crystalline solid precipitates. The solution is cooled, and the solid product, ethyl 5-(p-chlorobenzyl)-3-carboxy-1,4-dimethylpyrrole-2 -acetate, is filtered and dried, m.p. 197–198° C.

(E) Ethyl 5-(p-chlorobenzoyl)-1,4-dimethylpyrrole-2-acetate

A 9.0 g. (0.0255 mole) sample of ethyl 5-(p-chlorobenzoyl)-3-carboxy-1,4 -dimethylpyrrole-2-acetate is heated under nitrogen at 210 to 230° C. for 2 hours. Gas evolves. The residue is molecularly distilled in a sublimator at 195° C., 0.05 mm/Hg. The sublimate is recrystallized from cyclohexane to give ethyl 5-(p-chlorobenzoyl)-1,4-dimethylpyrrole-2 -acetate as a white solid, m.p. 107–109° C.

(F) 5-(p-Chlorobenzoyl)-1,4-dimethylpyrrole-2-acetic acid

A suspension of 4.0 g. (0.0125 mole) of ethyl 5-(p-chlorobenzoyl)-1,4 -dimethylpyrrole-2-acetate in 26 ml. of 0.5 N sodium hydroxide (0.013 mole) is heated under reflux for 30 minutes. The resulting solutions is acidified with dilute hydrochloric acid, and the precipitated solid is collected by filtration, air dried and recrystallized from 2-propanol to give 5-(p-chlorobenzoyl)-1,4-dimethylpyrrole-2-acetic acid as a white crystalline solid, m.p. 178–179° C. Anal. Calcd. for $C_{15} H_{14}$ $ClNO_3$: C, 61.76; H, 4.83; N, 4.82%. Found: C, 61.68; H, 4.96; N, 4.89%.

(G) 4,6-Dimethyl-5-(p-chlorobenzoyl)-1,3,6-trihydro-6-aza-3-oxapentalen-2-one 5-(p-Chlorobenzoyl)-1,4-dimethylpyrrole-2-acetic acid is subjected to the procedure of Example 1, part C to produce 4,6-dimethyl-5-(p-chlorobenzoyl)-1,3,6-trihydro-6-aza-3 -oxapentalen-2-one ($R_1$=H, $R_2$=H, $R_3$=4'-chlorophenyl, $R_4$=methyl, $R_5$=methyl, Y=CO,m=1, n=0).

EXAMPLE 73

4,6-Dimethyl-5-(p-Toluoyl)-1,3,6-Trihydro-6-Aza-3-Oxapentalen-2-One (A) Ethyl 1,4-dimethyl-3-ethoxycarbonyl-5(p-toluoyl)-pyrrole-2-acetate A solution of 30.8 g. p-toluoyl chloride and 26.6 g. (0.2 mole) of aluminum chloride in 250 ml. of 1,2-dichloroethane is added to a refluxing solution of 50.6 g. (0.2 mole) of ethyl 3-ethoxycarbonyl-1,4-dimethylpyrrole-2-acetate in 250 ml. of 1,2-dichloroethane over 30 minutes. The mixture is heated under reflux for 90 minutes, and poured into ice-diluted hydrochloric acid. The organic solution is separated, washed with brine, and dried over magnesium sulfate. The solvent is evaporated in vacuo, and the residue is recrystallized from methanol to give ethyl 1,4-dimethyl-3-ethoxycarbonyl-5-(p-toluoyl)-pyrrole-2-acetate as a white solid, m.p. 108–111°° C.

(B) 3-Carboxy-1,4-dimethyl-5-(p-toluoyl)-pyrrole-2-acetic acid

A suspension of 54 g. (0.145 mole) of ethyl 1,4-dimethyl-3-ethoxycarbonyl-5 -(p-toluoyl)-pyrrole-2-acetate in 500 g.

of 25% sodium hydroxide is heated at just below reflux for 3 hours. The yellow suspension is then poured into ice-hydrochloric acid, and the precipitated solid is collected, air dried and recrystallized from acetone-water to give 3-carboxy-1,4-dimethyl-5-(p-toluoyl)-pyrrole-2-acetic acid as a white solid, m.p. 229–230° C. Anal. Calcd. for $C_{17}H_{17}NO_5$: C, 64.75; H, 5.43; N, 4.44%. Found: C, 64.86; H, 5.53; N, 4.47%.

(C) Ethyl 3-carboxy-1,4-dimethyl-5-(p-toluoyl)-pyrrole-2-acetate

A solution of 37 g. (0.118 mole) of 3-carboxy-1,4-dimethyl-5-(p-toluoyl)-pyrrole-2 -acetic acid in 370 ml. of ethanol containing 1.8 g. of dry hydrogen chloride is heated under reflux for 45 minutes. The solution is cooled, and the solid which precipitated, ethyl 3 -carboxy-1,4-dimethyl-5-(o-toluoyl)-pyrrole-2-acetate, is collected, m.p. 200–202° C.

(D) Ethyl 1,4-dimethyl-5-(p-toluoyl)-pyrrole-2-acetate

A solution of 33.0 g. (0.096 mole) of ethyl 3-carboxy-1, 4-dimethyl-5 -(p-toluoyl)-pyrrole-2-acetate in 200 ml. of quinoline with 0.1 g. copper chromite added is heated under nitrogen for 6 hours at 200° C., then for 30 minutes at 220° C. The quinoline is distilled off in vacuo. The residue is dissolved in ether and washed successively with dilute hydrochloric acid, dilute sodium hydroxide, and brine; dried over magnesium sulfate; and the solvent evaporated in vacuo to give a brown oily residue which crystallizes. It is recrystallized from methanol, sublimed at 150° C. (0.025 mm/Hg) and recrystallized from hexane to give ethyl 1,4-dimethyl-5-(p-toluoyl)-pyrrole-2-acetate as a white solid, m.p. 90–93° C.

(E) 1,4-Dimethyl-5-(p-toluoyl)-pyrrole-2-acetic acid

A suspension of 8.5 g. (0.0284 mole) of ethyl 1,4-dimethyl-5-(p-toluoyl)-pyrrole-2 -acetate in 29 ml. of 1N sodium hydroxide solution is heated under reflux for 20 minutes. The yellow solution is diluted with water and added to dilute hydrochloric acid. The precipitated solid is collected, dried in vacuo, and recrystallized from 2-propanol to give 1,4-dimethyl-5 -(p-toluoyl)-pyrrole-2-acetic acid as a white solid, m.p. 160–161° C. Anal. Calcd. for $C_{16}H_{17}NO_3$: C, 70.83; H, 6.32; N, 5.16%. Found: C, 70.90; H, 6.39; N, 5.25%.

(F) 4,6-Dimethyl-5-(p-toluoyl)-1,3,6-trihydro-6-aza-3-oxapentalen-2-one 1,4-Dimethyl-5-(p-toluoyl)-pyrrole-2-acetic acid is subjected to the procedure of Example 1, part C to produce 4,6-dimethyl-5-(p-toluoyl)-1,3,6-trihydro-6-aza-3-oxapentalen-2-one ($R_1$=H, $R_2$=H, $R_3$=4'-methylphenyl, $R_4$=methyl, $R_5$=methyl, Y=CO, m=1, n=0).

EXAMPLE 74

4,6-Dimethyl-5-Benzoyl-1,3,6-Trihydro-6-Aza-3-Oxapentalen-2-One (A) 5-Benzoyl-1,4-dimethylpyrrole-2-acetic acid By following the procedure outlined in Example 72B-F, except that an equivalent quantity of benzoyl chloride is employed as the starting acylating agent in place of the p-chlorobenzoyl chloride used in Example 72B, there is obtained 5-benzoyl-1,4-dimethylpyrrole-2-acetic acid.

(B) 4,6-Dimethyl-5-benzoyl-1,3,6-trihydro-6-aza-3-oxapentalen-2-one

5-Benzoyl-1,4-dimethylpyrrole-2-acetic acid is subjected to the procedure of Example 1, part C to produce 4,6-dimethyl-5-benzoyl-1,3,6-trihydro-6-aza-3-oxapentalen-2-one ($R_1$=H, $R_2$=H, $R_3$=phenyl, R4=methyl, $R_5$=methyl, Y=CO, m=1, n=0).

EXAMPLE 75

4,6-Dimethyl-5-(2',3',5'-Tribromobenzoyl)-1,3,6-Trihydro-6-Aza-3-Oxapentalen-2-One (A) 5-(2', 3', 5'-Tribromobenzoyl)-1,4-dimethylpyrrole-2-acetic acid By following the procedure outlined in Example 72B-F, except that an equivalent quantity of 2,3,5-tribromobenzoyl chloride is employed as the starting acylating agent in place of the p-chlorobenzoyl chloride used in Example 72B, there is obtained 5-(2', 3', 5'-tribromobenzoyl)-1,4-dimethylpyrrole-2-acetic acid.

(B) 4,6-Dimethyl-5-(2',3',5'-Tribromobenzoyl)-1,3,6-Trihydro-6-Aza-3-Oxapentalen-2-One 5-(2', 3', 5'-Tribromobenzoyl)-1,4-dimethylpyrrole-2-acetic acid is subjected to the procedure of Example 1, part C to produce 4,6-dimethyl-5-(2',3',5'-tribromobenzoyl)-1,3, 6-trihydro-6-aza-3-oxapentalen-2-one ($R_1$=H, $R_2$=H, $R_3$=2',3',5'-tribromophenyl, $R_4$=methyl, $R_5$=methyl, Y=CO, m=1, n=0).

EXAMPLE 76

4-Ethyl-6-Methyl-5-(4'-Chlorobenzoyl)-1,3,6-Trihydro-6-Aza-3-Oxapentalen-2-One (A) 1-Chloro-2-butanone Chlorination of methylethylketone is carried out according to Bruylant and Houssiau [Bull. Soc. Chem. Belg., 6, 492 (1952)]. The mixture obtained is fractionally distilled at atmospheric pressure through a Vigreaux column. The fraction boiling at 135–144° C. is shown by vapor phase chromatography to contain approximately 75% 1-chloro-2-butanone and 25% 3-chloro-2-butanone. This fraction may be used in the next step without further separation.

(B) Ethyl 3-ethoxycarbonyl-4-ethyl-1-methylpyrrole-2-acetate

A 900 ml. solution of 25% aqueous methylamine is cooled in an ice bath and 101 g. (0.5 mole) of diethyl acetone decarboxylate is added. To the mixture is added 110 g. of the 1-chloro-2-butanone obtained in part A. Intermittant cooling is applied to keep the temperature below 60° C. The mixture is stirred for one hour and poured into ice-hydrochloric acid. The crystalline product is collected by filtration and recrystallized from methanol to yield ethyl 3-ethoxycarbonyl-4-ethyl-1-methylpyrrole-2-acetate as in a white solid, m.p. 65–67° C.

(C) Ethyl (5-p-chlorobenzoyl)-3-ethoxycarbonyl-4-ethyl-1-methylpyrrole-2-acetate A solution of 13.8 g. (0.0788 mole) of p-chlorobenzoyl chloride and 10.5 g. (0.0788 mole) of aluminum chloride in 120 ml. of 1,2-dichloroethane is added to a refluxing solution of 21.8 g. (0.0788 mole) of ethyl 3-ethoxycarbonyl-4-ethyl-1-methylpyrrole-2-acetate. The mixture is heated under reflux for 10 hours and stirred at room temperature for an additional 10 hours. It is then poured into ice-hydrochloric acid. The organic layer is separated, and the aqueous layer washed with 1,2-dichloroethane. The combined organics are washed successively with water, N,N-dimethylaminopropylamine, dilute HCl and brine. The solution is then dried over anhydrous magnesium sulfate and the solvent evaporated in vacuo. The residual red oily residue crystallizes on standing. It is recrystallized twice from methanol to give ethyl (5-chlorobenzoyl)-3-ethoxycarbonyl-4-ethyl-1-methyl-pyrrole-acetate as a white solid, m.p. 72–74° C.

(D) 3-carboxy-5-(p-chlorobenzoyl)-4-ethyl-1-methylpyrrole-2-acetic acid

A suspension of 18.2 g. (0.044 mole) of ethyl 5-(p-chlorobenzoyl)-3-ethoxycarbonyl-4-ethyl-1-methylpyrrole-2-acetate in 170 ml. of 25% aqueous sodium hydroxide solution is heated under reflux for 3 hours. It is cooled, diluted with water and acidified with dilute hydrochloric acid. The precipitated solid is collected by filtration and air dried. It is recrystallized from acetone-water to give 3-carboxy-5-(p-chlorobenzoyl)-4-ethyl-1-methylpyrrole-2-acetate acid, m.p. 211–212.5° C.

(E) Ethyl 3-carboxy-5-(p-chlorobenzoyl)-4-ethyl-1-methylpyrrole-2-acetate

A solution of 13.8 g. (0.0375 mole) of 3-carboxy-5-(p-chlorobenzoyl)-4-ethyl-1-methylpyrrole-2-acetic acid in 140 ml. of 0.5% ethanolic hydrogen chloride is heated under reflux for 45 minutes. After cooling, the precipitated solid is collected. A second crop is obtained by partial evaporation of the solvent, recrystallized from ethanol and combined with the first crop to give ethyl 3-carboxy-5-(γ-chlorobenzoyl)-4-ethyl-1-methylpyrrole-2-acetate, m.p. 184–186° C.

(F) Ethyl 5-(p-chlorobenzoyl)-4-ethyl-1-methylpyrrole-2-acetate

A 13.7 g. (0.035 mole) sample of ethyl 3-carboxy-5-(p-chlorobenzoyl)-4-ethyl-1-methypyrrole-2-acetate is heated at 200° C. to 210° C. under nitrogen for 90 minutes. The resulting oil is molecularly distilled at 185° C. and 0.1 mm pressure to yield a solid which is recrystallized from cyclohexane and then methanol to give ethyl 5-(p-chlorobenzoyl)-4-ethyl-1-methylpyrrole-2-acetate as a white solid, m.p. 73–75° C.

(G) 5-(p-Chlorobenzoyl)-4-ethyl-1-methylpyrrole-2-acetic acid

A suspension of 4.5 g. (0.0136 mole) of ethyl 5-(p-chlorobenzoyl)-4-ethyl-1-methylpyrrole-2-acetate in 28 ml. 0.5 N sodium hydroxide and 1 ml. of ethanol is heated under reflux for 30 minutes. The mixture is then poured into ice-dilute hydrochloric acid. The precipitated solid is filtered, air dried and recrystallized from 2-propanol to give 5-(p-chlorobenzoyl)-4-ethyl-1-methylpyrrole-2-acetic acid as a white solid, m.p. 129–131° C. Anal. Calcd. for $C_{16}H_{16}ClNO_3$: C, 62.85; H, 5.29; N, 4.5%. Found: C, 62.58; H, 5.40; N, 4.83%.

(H) 4-Ethyl-6-methyl-5-(4'-chlorobenzoyl)-1,3,6-trihydro-6-aza-3-oxapentalen-2-one 5-(p-Chlorobenzoyl)-4-ethyl-1-methylpyrrole-2-acetic acid is subjected to the procedure of Example 1, Part C to produce 4-ethyl-6-methyl-5-(4'-chlorobenzoyl)-1,3,6-trihydro-6-aza-3-oxapentalen-2-one ($R_1$=H, $R_2$=H, $R_3$=4'-chlorophenyl, $R_4$=ethyl, $R_5$=methyl, Y=CO, m=1, n =0).

EXAMPLE 77

Rac-1,4,6-Trimethyl-5-(p-Chlorobenzoyl)-1,3,6-Trihydro-6-Aza-3-Oxapentalen-2-One (A) Ethyl 5-(p-chlorobenzoyl)-1,4,α-trimethylpyrrole-2-acetate 6.4 grams (0.02 mole) of ethyl 5-(p-chlorobenzoyl)-1,4-dimethylpyrrole-2-acetate is dissolved in 100 ml. of dimethyl sulfoxide (DMSO) and added to a slurry of 0.48 g. (0.02 mole) of sodium hydride in approximately 30 ml. of DMSO. The mixture is stirred for 30 minutes before 2.84 g. (0.02 mole) of methyl iodide is added. Stirring is continued for 15 minutes. The reaction mixture is then poured into water, and the precipitate filtered off and recrystallized from 2-propanol to yield ethyl 5-(p-chlorobenzoyl)-1,4,α-trimethylpyrrole-2-acetate, m.p. 88–90° C.

(B) 5-(p-Chlorobenzoyl)-1,4,α-trimethylpyrrole-2-acetic acid

An ethanol solution of 2.9 g. (0.0087 mole) of ethyl 5-(p-chlorobenzoyl)1,4,α-trimethylpyrrole-2-acetate is added to 17.5 ml. 0.5 N sodium hydroxide solution, and the mixture is heated under reflux for one hour. The ethanol is evaporated in vacuo and the solution poured into dilute hydrochloric acid. The precipitated solid is collected by filtration and recrystallized from ether-cyclohexane to give 5-(p-chlorobenzoyl)-1,4,α-trimethylpyrrole-2-acetic acid as a white solid, m.p. 153–154° C. Anal. Calcd. for $C_{16}H_{16}ClNO_3$: C, 62.85; H, 5.29; N, 4.58%. Found: C, 62.74; H, 5.22; N, 4.47%.

(C) Rac-1,4,6-trimethyl-5-(p-chlorobenzoyl)-1,3,6-trihydro-6-aza-3-oxapentalen-2-one 5-(p-Chlorobenzoyl)-1,4-trimethyl-pyrrole-2-acetic acid is subjected to the procedure of Example 1, Part C to produce rac-1,4,6-trimethyl-5-(p-chlorobenzoyl)-1,3,6-trihydro-6-aza-3-oxapentalen-2-one ($R_1$=methyl, $R_2$=H, $R_3$=4'-chlorophenyl, $R_4$=methyl, $R_5$=methyl, Y=CO, m=1, n=0).

EXAMPLE 78

Rac-1,4,6-Trimethyl-5-(4'-Toluoyl)-1,3,6-Trihydro-6-Aza-3-Oxapentalen-2-One (A) Ethyl 1,4,α-trimethyl-5-(p-toluoyl)-pyrrole-2-acetate The methylation procedure of Example 77A is repeated, except that an equivalent quantity of the ester obtained from Examples 73D is methylated instead of the ethyl 5-(p-chlorobenzoyl)-1,4-dimethylpyrrole-2-acetate used in Example 77A, to yield ethyl 1,4,α-trimethyl-5-(p-toluoyl)-pyrrole-2-acetate.

(B) 1,4,α-trimethyl-5-(p-toluoyl)-pyrrole-2-acetic acid

The hydrolysis procedure of Example 77B is followed in transforming the α-methyl ester obtained in part A of this Example to yield 1,4,α-trimethyl-5-(p-toluoyl)-pyrrole-2-acetic acid.

(C) Rac-1,4,6-trimethyl-5-(4'-toluoyl)-1,3,6-trihydro-6-aza-3-oxapentalen-2-one

The acid from Example 78B is subjected to the procedure of Example 1, part C to produce rac-1,4,6-trimethyl-5-(4'-toluoyl)-1,3,6-trihydro-6-aza-3-oxapentalen-2-one ($R_1$= methyl, $R_2$=H, $R_3$=4'-methylphenyl, $R_4$=methyl, $R_5$=methyl, Y=CO, m=1, n=0).

EXAMPLE 79

Rac-1,4,6-Trimethyl-5-Benzoyl-1,3,6-Trihydro-6-Aza-3-Oxapentalen-2-One (A) Ethyl 1,4,α-trimethyl-5-benzoyl-pyrrole-2-acetate The methylation procedure of Example 77A is repeated, except that an equivalent quantity of the ester obtained from Example 74A is methylated instead of the ethyl 5-(p-chlorobenzoyl)-1,4-dimethylpyrrole-2-acetate used in Example 77A, to yield ethyl 1,4, α-trimethyl-5-benzoyl-pyrrole-2-acetate.

(B) 1,4,α-trimethyl-5-benzoyl-pyrrole-acetic acid

The hydrolysis procedure of Example 77B is followed in transforming the α-methyl ester obtained in part A of this Example to yield 1,4,α-trimethyl-5-benzoyl-pyrrole-2-acetic acid.

(C) Rac-1,4,6-trimethyl-5-benzoyl-1,3,6-trihydro-6-aza-3-oxapentalen-2-one

The acid from Example 79B is subjected to the procedure of Example 1, part C to produce rac-1,4,6-trimethyl-5-benzoyl-1,3,6-trihydro-6-aza-3-oxapentalen-2-one ($R_1$=methyl, $R_2$=H, $R_3$=phenyl, $R_4$=methyl, $R_5$=methyl, Y=CO, m=1, n=0).

EXAMPLE 80

4-Ethyl-1,6-Dimethyl-5-Benzoyl-1,3,6-Trihydro-6-Aza-3-Oxapentalen-2-One (A) Ethyl 4-ethyl-1,α-dimethyl-5-benzoyl-pyrrole-2-acetate The methylation procedure of Example 78A is repeated, except that an equivalent quantity of the ester obtained from Examples 73D, 74A and 76F is methylated instead of the ethyl 5-(p-chlorobenzoyl)-1,4-dimethylpyrrole-2-acetate used in Example 77A, to yield ethyl 4-ethyl-1, α-dimethyl-5-benzoyl-pyrrole-2-acetate (B) 4-Ethyl-1,α-dimethyl-5-benzoyl-pyrrole-2-acetic acid The hydrolysis procedure of Example 77B is followed in transforming the α-methyl ester obtained in part A of this Example to yield 4-ethyl-1,α-dimethyl-5-benzoyl-pyrrole-2-acetic acid.

(C) Rac-4-ethyl-1,6-dimethyl-5-benzoyl-1,3,6-trihydro-6-aza-3-oxapentalen-2-one

The acid from Example 80B is subjected to the procedure of Example 1, part C to produce rac-4-ethyl-1,6-dimethyl-5-benzoyl-1,3 ,6-trihydro-6-aza- 3-oxapentalen-2-one. $R_1$=methyl, $R_2$=H, $R_3$=phenyl, $R_4$=methyl, $R_5$=ethyl, Y=CO, m=1, n=0).

EXAMPLE 81

1,6-Dimethyl-5-(4'-Chlorobenzoyl)-1,3,6-Trihydro-6-Aza-3-Oxa-Pentalen-2-One Synthesized with (−) Acid (A) (−)-5-(p-Chlorobenzoyl)-1,α-dimethylpyrrole-2-acetic acid A solution of 16.5 g. (0.057 mole) of racemic 5-(p-chlorobenzoyl)-α-methyl-1-methylpyrrole-2-acetic acid and 6.8 g. (0.057 mole) of (+)-α-methylbenzylamine in 95% ethanol deposits crystals on standing. The solid is collected and recrystallized twice from 2-propanol to give 4.4 g. of salt, m.p. 181–182° C., the mother liquors being set aside for use as shown in Example 82. The salt is partitioned between ether and 3N hydrochloric acid. The ether layer is washed with dilute hydrochloric acid and brine and dried over magnesium sulfate. The solvent is evaporated in vacuo. The solid residue is dissolved in hot ether and methylcyclohexane is added. The ether is allowed to evaporate and the precipitated solid, (−)-5-(p-chlorobenzoyl)-1,α-dimethylpyrrole-2-acetic acid, is collected by filtration: (13% yield), m.p. 106–107° C.

(B) 1,6-Dimethyl-5-(4'-chlorobenzoyl)-1,3,6-trihydro-6-aza-3-oxa-pentalen-2-one synthesized with (−) acid The acid from Example 81 A is subjected to the procedure of Example 1, part C to produce 1,6-dimethyl-5-(4'-chlorobenzoyl)-1,3,6-trihydro-6-aza-3-oxa-pentalen-2-one ($R_1$=methyl, $R_2$=H, $R_3$=4'-chlorophenyl, $R_4$=methyl, $R_5$=H, Y=CO, m=1, n=0).

EXAMPLE 82

1,6-Dimethyl-5-(4'-Chlorobenzoyl)-1,3,6-Trihydro-6-Aza-3-Oxapentalen-2-One Synthesized with (+) Acid (A) (+)-5-(p-Chlorobenzoyl)-1,α-dimethylpyrrole-2-acetic acid The mother liquors set aside in Example 81 are evaporated to dryness. The residue is acidified with 3N hydrochloric acid and the precipitated acid is extracted into ether. The ether solution is then extracted with saturated sodium bicarbonate solution. The latter is acdified with dilute HCl, and the precipitated solid is extracted into ether. The ether solution is washed with brine, dried over anhydrous magnesium sulfate and evaporated to dryness to yield 5-(p-chlorobenzoyl)-α-methyl-1-methylpyrrole-2-acetic acid [presumably rich in the (+) enanthiomorph] as a yellow solid. A 14.8 g. sample is dissolved in ethanol. To the solution is added 6.15 g. (0.051 mole) of (−)-α-methylbenzylamine. A crystalline salt precipitates on standing which is collected and recrystallized three times from 2-propanol to give about 6.6 g. of white crystals, m.p. 175–177° C. The salt is partitioned between ether and 3N HCl solution. The ether layer is washed with dilute HCl and brine and dried over magnesium sulfate. The solvent is partially evaporated in vacuo, and methylcyclohexane is added. The ether is allowed to evaporate at room temperature, and the precipitate is collected. It is recrystallized once more in the same manner to yield (21% yield) of(+)-5-(p-chlorobenzoyl)-1,α-dimethylpyrrole-2-acetic acid as a white solid, m.p. 105.5–106.5° C.

(B) 1,6-Dimethyl-5-(4'-chlorobenzoyl)-1,3,6-trihydro-6-aza-3-oxa-pentalen-2-one synthesized with (+) acid The acid from Example 82A is subjected to the procedure of Example 1, part C to produce 1,6-dimethyl-5-(4'-chlorobenzoyl)-1,3,6-trihydro-6-aza-3-oxa-pentalen-2-one ($R_1$=methyl, $R_2$=H, $R_3$=4'-chlorophenyl, $R_4$=methyl, $R_5$=H, Y=CO, m=1, n=0).

EXAMPLE 83

4,6-Dimethyl-5-(4'- Fluorobenzoyl)-1,3,6-Trihydro-6-Aza-3-Oxapentalen-2-One (A) 3-Carboxy-1,4-dimethylpyrrolc-2-acetic acid A mixture of 176 g. (0.7 mole) of ethyl 1,4-dimethyl-3-ethoxycarbonylpyrrole-2-acetate and 1760 ml. of 25% sodium hydroxide solution is heated under reflux for 3 hours and then cooled and acidified with dilute hydrochloric acid. The precipitated solid is filtered and air dried. There is obtained 3-carboxy-1,4-dimethylpyrrole-2-acetic acid as a gray solid, m.p. 220–222° C.

(B) Ethyl 3-carboxy-1,4-dimethylpyrrole-2-acetate

A solution of 130 g. (0.66 mole) of 3-carboxy-1,4-dimethylpyrrole-2-acetic acid in 1300 ml. of 0.5% ethanolic hydrogen chloride is heated under reflux for 45 minutes, and then filtered while hot. A white solid, ethyl 3-carboxy-1,4-dimethylpyrrole-2-acetate, precipitates from the filtrate on cooling, m.p. 182–185° C.

(C) Ethyl 1,4-dimethylpyrrole-2-acetate

A 70.0 g. sample (0.31 mole) of ethyl 3-carboxy-1,4-dimethylpyrrole-2-acetate is heated under nitrogen at 190–210° C. until gas evolution ceases. The resulting yellow liquid is distilled at 82–90° C. at 0.25 mm. to give about 41 g. (73% yield) of a clear colorless liquid, ethyl 1,4-dimethylpyrrole-2-acetate.

(D) Ethyl 1,4-dimethyl-5-(p-fluorobenzoyl)-pyrrole-2-acetate

A solution of 3.95 g. (0.025 mole) of p-fluorobenzoyl chloride and 3.32 g. (0.025 mole) of aluminum chloride in 20 ml. of 1,2-dichloroethane is added dropwise to a solution of 4.52 g. (0.025 mole) of ethyl 1,4-dimethylpyrrole-2-acetate in 20 ml. of 1,2-dichloroethane at room temperature. The reaction mixture is stirred for 2 hours, and then cooled and poured into ice-dilute HCl. The organic phase is separated and washed successively with N,N-dimethyl-1,3-propanediamine, dilute hydrochloric acid and a saturated solution of sodium chloride; dried over anhydrous magnesium sulfate; and the solvent evaporated. The residue is triturated with hot hexane and crystals form upon cooling. There is obtained about 1.9 g. (25% yield) of ethyl 1,4-dimethyl-5-(p-fluorobenzoyl)-pyrrole-2-acetate as a white solid, m.p. 84–86° C. Upon recrystallization from methanol, the m.p. is 87–89° C.

(E) 1,4-Dimethyl-5-(p-fluorobenzoyl)-pyrrole-2-acetic acid

A suspension of 3.03 g. (0.01 mole) of ethyl 1,4-dimethyl-5-(p-fluorobenzoyl)-pyrrole-2-acetate in 11 ml. of 1N sodium hyroxide solution is heated under reflux for 30 minutes. The solution is filtered while hot and acidified with dilute hydrochloric acid. The precipitate is collected, air dried and recrystallized from 2-propanol to give about 2.5 g. (91% yield) of 1,4-dimethyl-5-(p-fluorobenzoyl)-pyrrole-2-acetic acid as a white solid, m.p. 176–178° C.

(F) 4,6-Dimethyl-5-(4'-fluorobenzoyl)-1,3,6-trihydro-6-aza-3-oxapentalen-2-one 1,4-Dimethyl-5-(p-fluorobenzoyl)-pyrolle-2-acetic acid is subjected to the procedure of Example 1, part C to produce 4,6-dimethyl-5-(4'-fluorobenzoyl)-1,3,6-trihydro-6-aza-3-oxapentalen-2-one ($R_1$=H, $R_2$=H, $R_3$=4'-fluorophenyl, $R_4$=methyl, $R_5$methyl, Y=CO, m=1, n=0).

EXAMPLE 84

4,6-Dimethyl-5-(4'-Chlorobenzoyl)-1,3,6-Trihydro-6-Aza-3-Oxapentalene-2-One (A) Ethyl 5-(p-chlorobenzoyl)-1,4-dimethylpyrrole-2-acetate The Friedel-Crafts acylation procedure of Example 83D is followed except that an equivalent quantity of p-chlorobenzoyl-chloride is substituted for the p-fluorobenzoyl chloride used therein to yield ethyl 5-(p-chlorobenzoyl)-1,4-dimethylpyrrole-2-acetate, m.p. 107–109° C.

(B) 1,4-Dimethyl-5-(p-chlorobenzoyl)pyrrole-2-acetic acid

The ester of part A of this Example is hydrolyzed in accordance with the procedure of Example 83E to yield 1,4-dimethyl-5-(p-chlorobenzoyl)pyrrole-2-acetic acid.

(C) 4,6-Dimethyl-5-(4'-chlorobenzoyl)-1,3,6-trihydro-6-aza-3-oxapentalene 1,4-Dimethyl-5-(p-chlorobenzoyl)pyrrole-2-acetic acid is subjected to the procedure of Example 1, part C to produce 4,6-dimethyl-5-(4'-chlorobenzoyl)-1,3,6-trihydro-6-aza-3-oxapentalene ($R_1$=H, $R_2$=H, $R_3$=4'-Chlorophenyl, $R_4$=Methyl, $R_5$=Methyl, Y=CO, m=1, n=0).

EXAMPLE 85

4,6-Dimethyl-5-(4'-Nitrobenzoyl)-1,3,6-Trihydro-6-Aza-3-Oxapentalen-2-One (A) Ethyl 5-(p-nitrobenzoyl)-1,4-dimethylpyrrole-2-acetate The Friedel-Crafts acylation procedure of Example 83D is followed except that an equivalent quantity of p-nitrobenzoyl chloride is substituted for the p-fluorobenzoyl chloride used therein to yield ethyl 5-(p-nitrobenzoyl)-1,4-dimethylpyrrole-2-acetate.

(B) 1,4-Dimethyl-5-(p-nitrobenzoyl)pyrrole-2-acetic acid

The ester of part A of this Example is hydrolyzed in accordance with the procedure of Example 83E to yield 1,4-dimethyl-5-(p-nitrobenzoyl)pyrrole-2-acetic acid.

(C) 4,6-Dimethyl-5-(4'-nitrobenzoyl)-1,3,6-trihydro-6-aza-3-oxapentalen-2-one 1,4-Dimethyl-5-(p-nitrobenzoyl)pyrrole-2-acetic acid is subjected to the procedure of Example 1, part C to produce 4,6-dimethyl-5-(4'-nitrobenzoyl)-1,3,6-trihydro-6-aza-3-oxapentalen-2-one ($R_1$=H, $R_2$=H, $R_3$=4'-nitrophenyl, $R_4$=methyl, $R_5$=methyl, Y=CO, m=1, n=0).

EXAMPLE 86

4,6-Dimethyl-5-Benzoyl-1,3,6-Trihydro-6-Aza-3-Oxapentalen-2-One (A) Ethyl 5-benzoyl-1,4-dimethylpyrrole-2-acetate The Friedel-Crafts acylation procedure of Example 83D is followed except that an equivalent quantity of benzoylchloride is substituted for the p-fluorobenzoyl chloride used therein to yield ethyl 5-benzoyl-1,4-dimethylpyrrole-2-acetate, m.p. 78–80° C.

(B) 1,4-Dimethyl-5-benzoyl-pyrrole-2-acetic acid

The ester of part A of this Example is hydrolyzed in accordance with the procedure of Example 83E to yield 1,4-dimethyl-5-benzoyl-pyrrole-2-acetic acid.

(C) 4,6-Dimethyl-5-benzoyl-1,3,6-trihydro-6-aza-3-oxapentalen-2-one 1,4-Dimethyl-5-benzoyl-pyrrole-2-acetic acid is subjected to the procedure of Example 1, part C to produce 4,6-dimethyl-5-benzoyl-1,3,6-trihydro-6-aza-3-oxapentalen-2-one ($R_1$=H, $R_2$=H, $R_3$=phenyl, $R_4$=methyl, $R_5$=methyl, Y=CO, m=1, n=0).

EXAMPLE 87

4,6-Dimethyl-5-(2'-Thenoyl)-1,3,6-Trihydro-6-Aza-3-Oxapentalen-2-One (A) Ethyl 5-(2'-thenoyl)-1,4-dimethylpyrrole-2-acetate The Friedel-Crafts acylation procedure of Example 83D is followed except that an equivalent quantity of 2'-thenoylchloride is substituted for the p-fluorobenzoyl chloride used therein to yield ethyl 5-(2'-thenoyl)-1,4-dimethylpyrrole-2-acetate.

(B) 1,4-Dimethyl-5-(2'-thenoyl)-pyrrole-2-acetic acid

The ester of part A of this Example is hydrolyzed in accordance with the procedure of Example 83E to yield 1,4-dimethyl-5-(2'-thenoyl)-pyrrole-2-acetic acid.

(C) 4,6-Dimethyl-5-(2'-thenoyl)-1,3,6-trihydro-6-aza-3-oxapentalen-2-one 1,4-Dimethyl-5-(2'-thenoyl)-pyrrole-2-acetic acid is subjected to the procedure of Example 1, part C to produce 4,6-dimethyl-5-(2'-thenoyl)-1,3,6-trihydro-6-aza-3-oxapentalen-2-one ($R_1$=H, $R_2$=H, $R_3$=2'-thiophenyl, $R_4$=methyl, $R_5$=methyl, Y=CO, m=1, n=0).

EXAMPLE 88

4,6-Dimethyl-5-(5'-Methyl-2'-Thenoyl)-1,3,6-Trihydro-6-Aza-3-Oxapentalen-2-One (A) Ethyl 5-(5'-methyl-2'-thenoyl)-1,4-dimethylpyrrole-2-acetate The Friedel-Crafts acylation procedure of Example 83D is followed except that an equivalent quantity of 5'-methyl-2'-thenoyl chloride is substituted for the p-fluorobenzoyl chloride used therein to yield ethyl 5-(5'-methyl-2'-thenoyl)-1,4-dimethylpyrrole-2-acetate.

(B) 1,4-Dimethyl-5-(5'-methyl-2'-thenoyl)pyrrole-2-acetic acid

The ester of part A of this Example is hydrolyzed in accordance with the procedure of Example 83E to yield 1,4-dimethyl-5-(5'-methyl-2'-thenoyl)pyrrole-2-acetic acid.

(C) 4,6-Dimethyl-5-(5'-methyl-2'-thenoyl)-1,3,6-trihydro-6-aza-3-oxapentalen-2-one 1,4-Dimethyl-5-(5'-methyl-2'-thenoyl)pyrrole-2-acetic acid is subjected to the procedure of Example 1, part C to produce 4,6-dimethyl-5-(5'-methyl-2'-thenoyl)-1,3,6-trihydro- 6-aza-3-oxapentalen-2-one ($R_1$=H, $R_2$=H, $R_3$=5'-methyl-2'-thiophenyl, $R_4$=methyl, $R_5$=methyl, Y=CO, m=1, n =0).

EXAMPLE 89

4,6-Dimethyl-5-(4'-Trifluoromethylbenzoyl)-1,3,6-Trihydro-6-Aza-3-Oxapentalen-2-One (A) Ethyl 5-(p-trifluoromethylbenzoyl)-1,4-dimethylpyrrole-2-acetate The Friedel-Crafts acylation procedure of Example 83D is followed except that an equivalent quantity of 4'-trifluoromethylbenzoyl chloride is substituted for the p-fluorobenzoyl chloride used therein to yield ethyl 5-(p-trifluoromethylbenzoyl)-1,4-dimethylpyrrole-2-acetate.

(B) 1,4-Dimethyl-5-(p-trifluoromethylbenzoyl)pyrrole-2-acetic acid

The ester of part A of this Example is hydrolyzed in accordance with the procedure of Example 83E to yield 1,4-dimethyl-5-(p-trifluoromethylbenzoyl)pyrrole-2-acetic acid.

(C) 4,6-Dimethyl-5-(4'-trifluoromethylbenzoyl)-1,3,6-trihydro-6-aza-3-oxapentalen-2-one 1,4-Dimethyl-5-(p-trifluoromethylbenzoyl)pyrrole-2-acetic acid is subjected to the procedure of Example 1, part C to produce 4,6-dimethyl-5-(4'-trifluoromethylbenzoyl)-1,3,6-trihydro-6-aza-3-oxapentalen-2-one ($R_1$=H, $R_2$=H, $R_3$=4'-trifluoromethylphenyl, $R_4$=methyl, $R_5$=methyl, Y=CO, m=1, n=0).

EXAMPLE 90

4,6-Dimethyl-5-(3',4'-Dimethoxybenzoyl)-1,3,6-Trihydro-6-Aza-3-Oxapentalen-2-One (A) Ethyl 5-(3',4'-dimethoxybenzoyl)-1,4-dimethylpyrrole-2-acetate The Friedel-Crafts acylation procedure of Example 83D is followed except that an equivalent quantity of 3',4'-dimethoxybenzoyl chloride is substituted for the p-fluorobenzoyl chloride used therein to yield ethyl 5-(3',4'-dimethoxybenzoyl)-1,4-dimethylpyrrole-2-acetate.

(B) 1,4-Dimethyl-5-(3',4'-dimethoxybenzoyl)-pyrrole-2-acetic acid

The ester of part A of this Example is hydrolyzed in accordance with the procedure of Example 83E to yield 1,4-dimethyl-5-(3',4'-dimethoxybenzoyl)-pyrrole-2-acetic acid.

(C) 4,6-Dimethyl-5-(3',4'-dimethoxybenzoyl)-1,3,6-trihydro-6-aza-3-oxapentalen-2-one 1,4-Dimethyl-5-(3',4'-dimethoxybenzoyl)-pyrrole-2-acetic acid is subjected to the procedure of Example 1, part C to produce 4,6-dimethyl-5-(3',4'-dimethoxybenzoyl)-1,3,6-trihydro- 6-aza-3-oxapentalen-2-one ($R_1$=H, $R_2$=H, $R_3$3',4'-dimethoxyphenyl, $R_4$=methyl, $R_5$=methyl, Y=CO, m=1, n=0).

EXAMPLE 91

4,6-Dimethyl-5-(2',3',5'-Tribromobenzoyl)-1,3,6-Trihydro-6-Aza-3-Oxapentalen-2-One (A) Ethyl 5-(2',3',5'-tribromobenzoyl)-1,4-dimethylpyrrole-2-acetate The Friedel-Crafts acylation procedure of Example 83D is followed except that an equivalent quantity of 2',3',5'-tribromobenzoyl chloride is substituted for the p-fluorobenzoyl chloride used therein to yield ethyl 5-(2',3',5'-tribromobenzoyl)-1,4-dimethylpyrrole-2-acetate.

(B) 1,4-Dimethyl-5-(2',3',5'-tribromobenzoyl)pyrrole-2-acetic acid

The ester of part A of this Example is hydrolyzed in accordance with the procedure of Example 83E to yield 1,4-dimethyl-5-(2',3',5'-tribromobenzoyl)pyrrole-2-acetic acid.

(C) 4,6-Dimethyl-5-(2',3',5'-tribromobenzoyl)-1,3,6-trihydro-6-aza-3-oxapentalen-2-one 1,4-Dimethyl-5-(2',3',5'-tribromobenzoyl)pyrrole-2-acetic acid is subjected to the procedure of Example 1, part C to produce 4,6-dimethyl-5-(2',3',5'-tribromobenzoyl)-1,3,6-trihydro-6-aza-3-oxapentalen-2-one ($R_1$=H, $R_2$=H, $R_3$=2',3',5'-tribromophenyl, methyl, $R_5$=methyl, Y=CO, m=1, n 0).

EXAMPLE 92

4,6-Dimethyl-5-(2'-Methylbenzoyl)-1,3,6-Trihydro-6-Aza-3-Oxapentalen-2-One (A) Ethyl 5-(o-methylbenzoyl)-1,4-dimethylpyrrole-2-acetate The Friedel-Crafts acylation procedure of Example 83D is followed except that an equivalent quantity of 2'-methylbenzoyl chloride is substituted for the p-fluorobenzoyl chloride used therein to yield ethyl 5-(o-methylbenzoyl)-1,4-dimethylpyrrole-2-acetate.

(B) 1,4-Dimethyl-5-(o-methylbenzoyl)pyrrole-2-acetic acid

The ester of part A of this Example is hydrolyzed in accordance with the procedure of Example 83E to yield 1,4-dimethyl-5-(o-methylbenzoyl)pyrrole-2-acetic acid.

(C) 4,6-Dimethyl-5-(2'-methylbenzoyl)-1,3,6-trihydro-6-aza-3-oxapentalen-2-one 1,4-Dimethyl-5-(o-methylbenzoyl)pyrrole-2-acetic acid is subjected to the procedure of Example 1, part C to produce 4,6-dimethyl-5-(2'-methylbenzoyl)-1,3,6-trihydro-6-aza- 3-oxapentalen-2-one ($R_1$=H, $R_2$=H, $R_3$=2'-methylphenyl, $R_4$=methyl, $R_5$=methyl, Y=CO, m=1, n=0).

EXAMPLE 93

4,6-Dimethyl-5-(4'-Cyanobenzoyl)-1,3,6-Trihydro-6-Aza-3-Oxapentalen-2-One (A) Ethyl 5-(p-cyanobenzoyl)-1,4-dimethylpyrrole-2-acetate The Friedel-Crafts acylation procedure of Example 83D is followed except that an equivalent quantity of 4'-cyanobenzoyl chloride is substituted for the p-fluorobenzoyl chloride used therein to yield ethyl 5-(p-cyanobenzoyl)-1,4-dimethylpyrrole-2-acetate.

(B) 1,4-Dimethyl-5-(p-cyanobenzoyl)pyrrole-2-acetic acid

The ester of part A of this Example is hydrolyzed in accordance with the procedure of Example 83E to yield 1,4-dimethyl-5-(p-cyanobenzoyl)pyrrole-2-acetic acid.

(C) 4,6-Dimethyl-5-(4'-cyanobenzoyl)-1,3,6-trihydro-6-aza-3-oxapentalen-2-one 1,4-Dimethyl-5-(p-cyanobenzoyl)pyrrole-2-acetic acid is subjected to the procedure of Example 1, part C to produce 4,6-dimethyl-5-(4'-cyanobenzoyl)-1,3,6-trihydro-6-aza-3-oxapentalen-2-one ($R_1$=H, $R_2$=H, $R_3$=4'-cyanophenyl, $R_4$=methyl, $R_5$=methyl, Y=CO, m=1, n 0).

EXAMPLE 94

4,6-Dimethyl-5-(4'-Aminobenzoyl)-1,3,6-Trihydro-6-Aza-3-Oxapentalen-2-One

By using an equivalent amount of 4,6-dimethyl-5-(4'-nitrobenzoyl)-1,3,6-trihydro-6-aza-3-oxapentalen-2-one in place of 5-(p-nitrobenzoyl)-1-methylpyrrole-2-acetonitrile in the hydrogenation procedure of Example 85C, the product, 4,6-dimethyl-5-(4'-aminobenzoyl)-1,3,6-trihydro-6-aza-3-oxapentalen-2-one is obtained. ($R_1$=H, $R_2$=H, $R_3$=4'-amino $R_4$=methyl, $R_5$=methyl, Y=CO, m=1, n=0).

EXAMPLE 95

Rac-1,4,6-Trimethyl-5-(4'-Fluorobenzoyl)-1,3,6-Trihydro-6-Aza-3-Oxapentalen-2-One (A) Ethyl 1,4,α-trimethyl-5-(p-fluorobenzoyl)-pyrrole-2-acetate The methylation procedure of Example 77A is repeated, except that an equivalent quantity of ethyl 1,4-dimethyl-5-(p-fluorobenzoyl)-pyrrole-2-acetate (from Example 83) is methylated instead of the ethyl 5-(p-chlorobenzoyl)-1,4-dimethylpyrrole-2-acetate used in Example 77A, to yield ethyl 1,4,α-trimethyl-5-(p-fluorobenzoyl)-pyrrole-2-acetate.

(B) 1,4,α-Trimethyl-5-(p-fluorobenzoyl)-pyrrole-2-acetic acid

The hydrolysis procedure of Example 77B is followed in transforming the ester from part A of this Example into 1,4,α-trimethyl-5-(p-fluorobenzoyl)-pyrrole-2-acetic acid.

(C) Rac-1,4,6-trimethyl-5-(4'-fluorobenzoyl)-1,3,6-trihydro-6-aza-3-oxapentalen-2-one 1,4,α-Trimethyl-5-(p-fluorobenzoyl)-pyrrole-2-acetic acid is subjected to the procedure of Example 1, part C to produce rac-1,4,6-trimethyl-5-(4'-fluorobenzoyl)-1,3,6-trihydro-6-aza-3-oxapentalen-2-one ($R_1$=methyl, $R_2$=H, $R_3$=4'-fluorophenyl, $R_4$=methyl $R_5$=methyl, Y=CO, m=1, n=0).

EXAMPLE 96

Rac-1,4,6-Trimethyl-5-(3'(A) Clorobenzoyl)-1,3,6-Trihydro-6-Aza-3-Oxapentalen-2-One (A) Ethyl 5-(m-chlorobenzoyl)-1,4,α-trimethylpyrrole-2-acetate The methylation procedure of Example 77A is repeated, except that an equivalent quantity of ethyl 5-(m-chlorobenzoyl)-1,4-dimethylpyrrole-2-acetate (from Example 84) is methylated instead of the ethyl 5-(m-chlorobenzoyl)-1,4-dimethylpyrrole-2-acetate used in Example 77A, to yield ethyl 5-(m-chlorobenzoyl)-1,4,α-trimethylpyrrole-2-acetate.

(B) 5-(m-Chlorobenzoyl)-1,4,α-trimethylpyrrole-2-acetic acid

The hydrolysis procedure of Example 77B is followed in transforming the ester from part A of this Example into 5-(m-chlorobenzoyl)-1,4,α-trimethylpyrrole-2-acetic acid.

(C) Rac-1,4,6-trimethyl-5-(3'-chlorobenzoyl)-1,3,6-trihydro-6-aza-3-oxapentalen-2-one 5-(m-Chlorobenzoyl)-1,4,α-trimethylpyrrole-2-acetic acid is subjected to the procedure of Example 1, part C to produce rac-1,4,6-trimethyl-5-(3'-chlorobenzoyl)-1,3,6-trihydro-6-aza-3-oxapentalen-2-one ($R_1$=methyl, $R_2$=H, $R_3$=3'-chlorophenyl, $R_4$=methyl, $R_5$=methyl, Y=CO, m=1, n=0).

EXAMPLE 97

Rac-1,4,6-Trimethyl-5-Benzoyl-1,3,6-Trihydro-6-Aza-3-Oxapentalen-2-One (A) Ethyl 5-benzoyl-1,4,α-trimethylpyrrole-2-acetate The methylation procedure of Example 77A is repeated, except that an equivalent quantity of ethyl 5-benzoyl-1,4-dimethylpyrrole-2-acetate (from Example 86) is methylated instead of the ethyl 5-(p-chlorobenzoyl)-1,4-dimethylpyrrole-2-acetate used in Example 77A, to yield ethyl 5-benzoyl-1,4,α-trimethylpyrrole-2-acetate.

(B) 5-Benzoyl-1,4,α-trimethylpyrrole-2-acetic acid

The hydrolysis procedure of Example 77B is followed in transforming the ester from part A of this Example into 5-benzoyl-1,4,α-trimethylpyrrole-2-acetic acid.

(C) Rac-1,4,6-trimethyl-5-benzoyl-1,3,6-trihydro-6-aza-3-oxapentalen-2-one

5-Benzoyl-1,4,α-trimethylpyrrole-2-acetic acid is subjected to the procedure of Example 1, part C to produce rac-1,4,6-trimethyl-5-benzoyl-1,3,6-trihydro-6-aza-3-oxapentalen-2-one ($R_1$=methyl, $R_2$=H, $R_3$=phenyl, $R_4$=methyl, $R_5$=methyl, Y=CO, m=1, n=0).

EXAMPLE 98

Rac-1,4,6-Trimethyl-5-(2'-Thenoyl)-1,3,6-Trihydro-6-Aza-3-Oxapentalen-2-One (A) Ethyl 5-(2'-thenoyl)-1,4,α-trimethylpyrrole-2-acetate The methylation procedure of Example 77A is repeated, except that an equivalent quantity of ethyl 5-(2'-thenoyl)-1,4-dimethylpyrrole-2-acetate (from Example 87) is methylated instead of the ethyl 5-(m-chlorobenzoyl)-1,4-dimethylpyrrole-2-acetate used in Example 77A, to yield ethyl 5-(2'-thenoyl)-1,4,α-trimethylpyrrole-2-acetate.

(B) 5-(2'-Thenoyl)-1,4,α-trimethylpyrrole-2-acetic acid

The hydrolysis procedure of Example 77B is followed in transforming the ester from part A of this Example into 5-(2'-thenoyl)-1,4,α-trimethylpyrrole-2-acetic acid.

(C) Rac-1,4,6-trimethyl-5-(2'-thenoyl)-1,3,6-trihydro-6-aza-3-oxapentalen-2-one 5-(2'-Thenoyl)-1,4,α-trimethylpyrrole-2-acetic acid is subjected to the procedure of Example 1, part C to produce rac-1,4,6-trimethyl-5-(2'-thenoyl)-1,3,6-trihydro-6-aza-3-oxapentalen-2-one ($R_1$=methyl, $R_2$=H, $R_3$=2'-thiophenyl, $R_4$=methyl, $R_5$=methyl, Y=CO, m=1, n=0).

EXAMPLE 99

Rac-1,4,6-Trimethyl-5-(5'-Methyl-2'-Thenoyl)-1,3,6-Trihydro-6-Aza-3-Oxapentalen-2-One (A) Ethyl 5-(5'-methyl-2'-thenoyl)-1,4,α-trimethylpyrrole-2-acetate The methylation procedure of Example 77A is repeated, except that an equivalent quantity of ethyl 5-(5'-methyl-2'-thenoyl)-1,4-dimethylpyrrole-2-acetate (from Example 88) is methylated instead of the ethyl 5-(p-chlorobenzoyl)-1,4-dimethylpyrrole-2-acetate used in Example 77A, to yield ethyl 5-(5'-methyl-2'-thenoyl)-1,4,α-trimethylpyrrole-2-acetate.

(B) 5-(5'-Methyl-2'-thenoyl)-1,4,α-trimethylpyrrole-2-acetic acid

The hydrolysis procedure of Example 77B is followed in transforming the ester from part A of this Examples into 5-(5'-methyl-2'-thenoyl)-1,4,α-trimethylpyrrole-2-acetic acid.

(C) Rac-1,4,6-trimethyl-5-(5'-methyl-2'-thenoyl)-1,3,6-trihydro-6-aza-3-oxapentalen-2-one 5-(5'-methyl-2'-thenoyl)-1,4,α-trimethylpyrrole-2-acetic acid is subjected to the procedure of Example 1, part C to produce rac-1,4,6-trimethyl-5-(5'-methyl-2'-thenoyl)-1,3,6-trihydro-6-aza-3-oxapentalen-2-one ($R_1$=methyl, $R_2$=H, $R_3$=5'-methyl-2'-thiophenyl, $R_4$=methyl, $R_5$=methyl, Y=CO, m=1, n=0).

EXAMPLE 100

Rac-1,4,6-Trimethyl-5-(4'-Trifluoromethylbenzoyl)-1,3,6-Trihydro-6-Aza-3-Oxapentalen-2-One (A) Ethyl 5-(p-trifluoromethylbenzoyl)-1,4,α-trimethylpyrrole-2-acetate The methylation procedure of Example 77A is repeated, except that an equivalent quantity of ethyl 5-(p-trifluoromethylbenzoyl)-1,4-dimethylpyrrole-2-acetate (from Example 89) is methylated instead of the ethyl 5-(p-chlorobenzoyl)-1,4-dimethylpyrrole-2-acetate used in Example 77A, to yield ethyl 5-(p-trifluoromethylbenzoyl)-1,4,α-trimethylpyrrole-2-acetate.

(B) 5-(p-Trifluoromethylbenzoyl)-1,4,α-trimethylpyrrole-2-acetic acid

The hydrolysis procedure of Example 77B is followed in transforming the ester from part A of this Example into 5-(p-trifluoromethylbenzoyl)-1,4,α-trimethylpyrrole-2-acetic acid.

(C) Rac-1,4,6-trimethyl-5-(4'-trifluoromethylbenzoyl)-1,3,6-trihydro-6-aza-3-oxapentalen-2-one 5-(p-Trifluoromethylbenzoyl)-1,4,α-trimethylpyrrole-2-acetic acid is subjected to the procedure of Example 1, part C to produce rac-1,4,6-trimethyl-5-(4'-trifluoromethylbenzoyl)-1,3,6-trihydro-6-aza-3-oxapentalen-2-one ($R_1$=methyl, $R_2$=H, $R_3$=4'-trifluoromethylphenyl, $R_4$=methyl, $R_5$=methyl, Y=CO, m=1, n=0).

EXAMPLE 101

Rac-1,4,6-Trimethyl-5-(3'4'-Dimethoxybenzoyl)-1,3,6-Trihydro-6-Aza-3-Oxapentalen-2-One (A) Ethyl 5-(3',4'-dimethoxybenzoyl)-1,4,α-trimethylpyrrole-2-acetate The methylation procedure of Example 77A is repeated, except that an equivalent quantity of ethyl 5-(3',4'-dimethoxybenzoyl)-1,4-dimethylpyrrole-2-acetate (from Example 90) is methylated instead of the ethyl 5-(p-chlorobenzoyl)-1,4-dimethylpyrrole-2-acetate used in Example 77A, to yield ethyl 5-(3',4'-dimethoxybenzoyl)-1,4,α-trimethylpyrrole-2-acetate.

(B) 5-(3',4'-Dimethoxybenzoyl)-1,4,α-trimethylpyrrole-2-acetic acid

The hydrolysis procedure of Example 77B is followed in transforming the ester from part A of this Example into 5-(3',4'-dimethoxybenzoyl)-1,4,α-trimethylpyrrole-2-acetic acid.

(C) Rac-1,4,6-trimethyl-5-(3'4'-dimethoxybenzoyl)-1,3,6-trihydro-6-aza-3-oxapentalen-2-one 5-(3',4'-Dimethoxybenzoyl)-1,4,α-trimethylpyrrole-2-acetic acid is subjected to the procedure of Example 1, part C to produce rac-1,4,6-trimethyl-5-(3'4'-dimethoxybenzoyl)-1,3,6-trihydro-6-aza-3-oxapentalen-2-one ($R_1$=methyl, $R_2$=H, $R_3$=3',4'-dime $R_4$=methyl, $R_5$=methyl, Y=CO, m=1, n=0).

EXAMPLE 102

Rac-1,4,6-Trimethyl-5-(2',3',5'-Tribromobenzoyl)-1,3,6-Trihydro-6-Aza-3-Oxapentalen-2-One (A) Ethyl 5-(2',3',5'-tribromobenzoyl)-1,4,α-trimethylpyrrole-2-acetate The methylation procedure of Example 77A is repeated, except that an equivalent quantity of ethyl 5-(2',3',5'-tribromobenzoyl)-1,4-dimethylpyrrole-2-acetate (from Example 91) is methylated instead of the ethyl 5-(p-chlorobenzoyl)-1,4-dimethylpyrrole-2-acetate used in Example 77A, to yield ethyl 5-(2',3',5'-tribromobenzoyl)-1,4,α-trimethylpyrrole-2-acetate.

(B) 5-(2',3',5'-Tribromobenzoyl)-1,4,α-trimethylpyrrole-2-acetic acid

The hydrolysis procedure of Example 77B is followed in transforming the ester from part A of this Example into 5-(2',3',5'-tribromobenzoyl)-1,4,α-trimethylpyrrole-2-acetic acid.

(C) Rac-1,4,6-trimethyl-5-(2',3',5'-tribromobenzoyl)-1,3,6-trihydro-6-aza-3-oxapentalen-2-one 5-(2',3',5'-Tribromobenzoyl)-1,4,α-trimethylpyrrole-2-acetic acid is subjected to the procedure of Example 1, part C to produce rac-1,4,6-trimethyl-5-(2',3',5'-tribromobenzoyl)-1,3,6-trihydro-6-aza-3-oxapentalen-2-one ($R_1$=methyl, $R_2$=H, $R_3$=2',3',5'-tribromophenyl, $R_4$=methyl, $R_5$=methyl, Y=CO, m=1, n=0).

EXAMPLE 103

Rac-1,4,6-Trimethyl-5-(2'-Methylbenzoyl)-1,3,6-Trihydro-6-Aza-3-Oxapentalen-2-One (A) Ethyl 5-(2'-methylbenzoyl)-1,4,α-trimethylpyrrole-2-acetate The methylation procedure of Example 77A is repeated, except that an equivalent quantity of ethyl 5-(2'- methylbenzoyl)-1,4-dimethylpyrrole-2-acetate (from Example 92) is methylated instead of the ethyl 5-(p-chlorobenzoyl)-1,4-dimethylpyrrole-2-acetate used in Example 77A, to yield ethyl 5-(2'-methylbenzoyl)-1,4,α-trimethylpyrrole-2-acetate.

(B) 5-(2'-Methylbenzoyl)-1,4,α-trimethylpyrrole-2-acetic acid

The hydrolysis procedure of Example 77B is followed in transforming the ester from part A of this Example into 5-(2'-methylbenzoyl)-1,4,α-trimethylpyrrole-2-acetic acid.

(C) Rac-1,4,6-trimethyl-5-(2'-methylbenzoyl)-1,3,6-trihydro-6-aza-3-oxapentalen-2-one 5-(2'-Methylbenzoyl)-1,4,α-trimethylpyrrole-2-acetic acid is subjected to the procedure of Example 1, part C to produce rac-1,4,6-trimethyl-5-(2'-methylbenzoyl)-1,3,6-trihydro-6-aza-3-oxapentalen-2-one ($R_1$=methyl, $R_2$=H, $R_3$=2'-methylphenyl, $R_4$=methyl, $R_5$=methyl, Y=CO, m=1, n=0).

EXAMPLE 104

Rac-1,4,6-Trimethyl-5-(4'-Cyanobenzoyl)-1,3,6-Trihydro-6-Aza-3-Oxapentalen-2-One (A) Ethyl 5-(p-cyanobenzoyl)-1,4,α-trimethylpyrrole-2-acetate The methylation procedure of Example 77A is repeated, except that an equivalent quantity of (from Example 93) is methylated instead of the ethyl 5-(p-chlorobenzoyl)-1,4-dimethylpyrrole-2-acetate used in Example 77A, to yield ethyl 5-(p-cyanobenzoyl)-1,4,α-trimethylpyrrole-2-acetate.

(B) 5-(p-Cyanobenzoyl)-1,4,α-trimethylpyrrole-2-acetic acid

The hydrolysis procedure of Example 77B is followed in transforming the ester from part A of this Example into 5-(p-cyanobenzoyl)-1,4,α-trimethylpyrrole-2-acetic acid.

(C) Rac-1,4,6-trimethyl-5-(4'-cyanobenzoyl)-1,3,6-trihydro-6-aza-3-oxapentalen-2-one 5-(p-Cyanobenzoyl)-1,4,α-trimethylpyrrole-2-acetic acid is subjected to the procedure of Example 1, part C to produce rac-1,4,6-trimethyl-5-(4'cyanobenzoyl)-1,3,6-trihydro-6-aza-3-oxapentalen-2-one ($R_1$=methyl, $R_2$=H, $R_3$=4'-cyanophenyl, $R_4$=methyl, $R_5$=methyl, Y=CO, m=1, n=0).

EXAMPLE 105

Rac-1-(n-Propyl)-4,6-Dimethyl-5-(4'-Chlorobenzoyl)-1,3,6-Trihydro-6-Aza-3-Oxapentalen-2-One (A) Ethyl 5-(p-chlorobenzoyl)-1,4-dimethylpyrrole-2-(α-n-propyl)-acetate The alkylation procedure of Example 77A is performed upon ethyl 5-(p-chlorobenzoyl)-1,4-dimethylpyrrole-2-acetate (from Example 84), using an equivalent quantity of n-propyl iodide instead of methyl iodide used in Example 77A to yield ethyl 5-(p-chlorobenzoyl)-1,4-dimethylpyrrole-2-(α-n-propyl)acetate.

(B) 5-(p-Chlorobenzoyl)-1,4-dimethylpyrrole-2-(α-n-propyl)-acetic acid

The hydrolysis procedure of Example 77B is followed in transforming the ester from part A of this Example into 5-(p-chlorobenzoyl)-1,4-dimethylpyrrole-2-(α-propyl)-acetic acid.

(C) Rac-1-(n-propyl)-4,6-dimethyl-5-(4'-chlorobenzoyl)-1,3,6-trihydro-6-aza-3-oxapentalen-2-one 5-(p-Chlorobenzoyl)-1,4-dimethylpyrrole-2-(α-propyl)-acetic acid is subjected to the procedure of Example 1, part C to produce rac-1-(n-propyl)-4,6-dimethyl-5-(4'-chlorobenzoyl)-1,3,6-trihydro-6-aza-3-oxapentalen-2-one ($R_1$=n-propyl, $R_2$=H, $R_3$=4'-chlorophenyl, $R_4$=methyl, $R_5$=methyl, Y=CO, m=1, n=0).

EXAMPLE 106

Rac-1-(n-Propyl)-4,6-Dimethyl-5-(4'-Nitrobenzoyl)-1,3,6-Trihydro-6-Aza-3-Oxapentalen-2-One (A) Ethyl 5-(p-nitrobenzoyl)-1,4-dimethylpyrrole-2-(α-n-propyl)-acetate The alkylation procedure of Example 77A is performed upon ethyl 5-(p-nitrobenzoyl)-1,4-dimethylpyrrole-2-acetate (from Example 85), using an equivalent quantity of n-propyl iodide instead of methyl iodide used in Example 77A to yield ethyl 5-(p-nitrobenzoyl)-1,4-dimethylpyrrole-2-(α-n-propyl)-acetate.

(B) 5-(p-Nitrobenzoyl)-1,4-dimethylpyrrole-2-(α-n-propyl)-acetic acid

The hydrolysis procedure of Example 77B is followed in transforming the ester from part A of this Example into 5-(p-nitrobenzoyl)-1,4-dimethylpyrrole-2-(α-n-propyl)-acetic acid.

(C) Rac-1-(n-propyl)-4,6-dimethyl-5-(4'-nitrobenzoyl)-1,3,6-trihydro-6-aza-3-oxapentalen-2-one 5-(p-Nitrobenzoyl)-1,4-dimethylpyrrole-2-(α-n-propyl)-acetic acid is subjected to the procedure of Example 1, part C to produce rac-1-(n-propyl)-4,6-dimethyl-5-(4'-nitrobenzoyl)-1,3,6-trihydro-6-aza-3-oxapentalen-2-one ($R_1$=n-propyl, $R_2$=H, $R_3$=4'-nitrophenyl, $R_4$=methyl, $R_5$=methyl, Y=CO, m=1, n=0).

EXAMPLE 107

Rac-1-(n-Propyl)-4,6-Dimethyl-5-Benzoyl-1,3,6-Trihydro-6-Aza-3-Oxapentalen-2-One (A) Ethyl 5-benzoyl-1,4-dimethylpyrrole-2-(α-n-propyl)-acetate The alkylation procedure of Example 77A is performed upon ethyl 5-benzoyl-1,4-dimethylpyrrole-2-acetate (from Example 86), using an equivalent quantity of n-propyl iodide instead of methyl iodide used in Example 77A to yield ethyl 5-benzoyl-1,4-dimethylpyrrole-2-(α-n-propyl)-acetate.

(B) 5-Benzoyl-1,4-dimethylpyrrole-2-(α-n-propyl)-acetic acid

The hydrolysis procedure of Example 77B is followed in transforming the ester from part A of this Example into 5-benzoyl-1,4-dimethylpyrrole-2-(α-n-propyl)-acetic acid.

(C) Rac-1-(n-propyl)-4,6-dimethyl-5-benzoyl-1,3,6-trihydro-6-aza-3-oxapentalen-2-one 5-Benzoyl-1,4-dimethylpyrrole-2-(α-n-propyl)-acetic acid is subjected to the procedure of Example 1, part C to produce rac-1-(n-propyl)-4,6-dimethyl-5-benzoyl-1,3,6-trihydro-6-aza-3-oxapentalen-2-one ($R_1$=n-propyl, $R_2$=H, $R_3$=phenyl, $R_4$=methyl, $R_5$=methyl, Y=CO, m=1, n=0).

EXAMPLE 108

Rac-1-(n-Propyl)-4,6-Dimethyl-5-(2'-Thenoyl)-1,3,6-Trihydro-6-Aza-3-Oxapentalen-2-One (A) Ethyl 5-(2'-thenoyl)-1,4-dimethylpyrrole-2-(α-n-propyl)-acetate The alkylation procedure of Example 77A is performed upon ethyl 5-(2'-thenoyl)-1,4-dimethylpyrrole-2-acetate (from Example 87), using an equivalent quantity of n-propyl iodide instead of methyl iodide used in Example 77A to yield ethyl 5-(2'-thenoyl)-1,4-dimethylpyrrole-2-(α-n-propyl)-acetate.

(B) 5-(2'-Thenoyl)-1,4-dimethylpyrrole-2-(α-n-propyl)-acetic acid

The hydrolysis procedure of Example 77B is followed in transforming the ester from part A of this Example into 5-(2'-thenoyl)-1,4-dimethylpyrrole-2-(α-n-propyl)-acetic acid.

(C) Rac-1-(n-propyl)-4,6-dimethyl-5-(2'-thenoyl)-1,3,6-trihydro-6-aza-3-oxapentalen-2-one 5-(2'-Thenoyl)-1,4-dimethylpyrrole-2-(α-n-propyl)-acetic acid is subjected to the procedure of Example 1, part C to produce rac-1-(n-propyl)-4,6-dimethyl-5-(2'-thenoyl)-1,3,6-trihydro-6-aza-3-oxapentalen-2-one ($R_1$=n-propyl, $R_2$=H, $R_3$=2'-thiophenyl, $R_4$=methyl, $R_5$=methyl, Y=CO, m=1, n=0).

EXAMPLE 109

Rac-1-(n-Propyl)-4,6-Dimethyl-5-(5'-Methyl-2'-Thenoyl)-1,3,6-Trihydro-6-Aza-3-Oxapentalen-2-One (A) Ethyl 5-(5'-methylthenoyl)-1,4-dimethylpyrrole-2-(α-n-propyl)-acetate The alkylation procedure of Example 77A is performed upon ethyl 5-(5'-methyl-2'-thenoyl)-1,4-dimethylpyrrole-2-acetate (from Example 88), using an equivalent quantity of n-propyl iodide instead of methyl iodide used in Example 77A to yield ethyl 5-(5'-methyl-2'-thenoyl)-1,4-dimethylpyrrole-2-(α-n-propyl)-acetate.

(B) 5-(5'-Methyl-2'-thenoyl)-1,4-dimethylpyrrole-2-(α-n-propyl)-acetic acid

The hydrolysis procedure of Example 77B is followed in transforming the ester from part A of this Example into 5-(5'-methyl-2'-thenoyl)-1,4-dimethylpyrrole-2-(α-n-propyl)-acetic acid.

(C) Rac-1-(n-propyl)-4,6-dimethyl-5-(5'-methyl-2'-thenoyl)-1,3,6-trihydro-6-aza-3-oxapentalen-2-one 5-(5'-Methyl-2'-thenoyl)-1,4-dimethylpyrrole-2-(α-n-propyl)-acetic acid is subjected to the procedure of Example 1, part C to produce rac-1-(n-propyl)-4,6-dimethyl-5-(5'-methyl-2'-thenoyl)-1,3,6-trihydro-6-aza-3-oxapentalen-2-one ($R_1$=n-propyl, $R_2$=H, $R_3$=5'-methyl-2'-thiophenyl, $R_4$=methyl, $R_5$=methyl, Y=CO, m=1, n=0).

EXAMPLE 110

Rac-1-(n-Propyl)-4,6-Dimethyl-5-(4'-Trifluoromethylbenzoyl)-1,3,6-Trihydro-6-Aza-3-Oxapentalen-2-One (A) Ethyl 5-(p-trifluoromethylbenzoyl)-1,4-dimethylpyrrole-2-(α-n-propyl)-acetate The alkylation procedure of Example 77A is performed upon ethyl 5-(p-trifluoromethylbenzoyl)-1,4-dimethylpyrrole-2-acetate (from Example 89), using an equivalent quantity of n-propyl iodide instead of methyl iodide used in Example 77A to yield ethyl 5-(p-trifluoromethylbenzoyl)-1,4-dimethylpyrrole-2-(α-n-propyl)-acetate.

(B) 5-(p-Trifluoromethylbenzoyl)-1,4-dimethylpyrrole-2-(α-n-propyl)-acetic acid

The hydrolysis procedure of Example 77B is followed in transforming the ester from part A of this Example into 5-(p-trifluoromethylbenzoyl)-1,4-dimethylpyrrole-2-(α-n-propyl)-acetic acid.

(C) Rac-1-(n-propyl)-4,6-dimethyl-5-(4'-trifluoromethylbenzoyl)-1,3,6-trihydro-6-aza-3-oxapentalen-2-one 5-(p-Trifluoromethylbenzoyl)-1,4-dimethylpyrrole-2-(α-n-propyl)-acetic acid is subjected to the procedure of Example 1, part C to produce rac-1-(n-propyl)-4,6-dimethyl-5-(4'-trifluoromethylbenzoyl)-1,3,6-trihydro-6-aza-3-oxapentalen-2-one ($R_1$=n-propyl, $R_2$=H, $R_3$ 4'-trifluoromethylphenyl, $R_4$=methyl, $R_5$=methyl, Y=CO, m=1, n=0).

EXAMPLE 111

Rac-1-(n-Propyl)-4,6-Dimethyl-5-(3',4'-Dimethoxybenzoyl)-1,3,6-Trihydro-6-Aza-3-Oxapentalen-2-One (A) Ethyl 5-(3',4'-dimethoxybenzoyl)-1,4-dimethylpyrrole-2-(α-n-propyl)-acetate The alkylation procedure of Example 77A is performed upon ethyl 5-(3',4'-dimethoxybenzoyl)-1,4-dimethylpyrrole-2-acetate (from Example 90), using an equivalent quantity of n-propyl iodide instead of methyl iodide used in Example 77A to yield ethyl 5-(3',4'-dimethoxybenzoyl)-1,4-dimethylpyrrole-2-(α-n-propyl)-acetate.

(B) 5-(3',4'-Dimethoxybenzoyl)-1,4-dimethylpyrrole-2-(α-n-propyl)-acetic acid

The hydrolysis procedure of Example 77B is followed in transforming the ester from part A of this Example into 5-(3',4'-dimethoxybenzoyl)-1,4-dimethylpyrrole-2-(α-n-propyl)-acetic acid.

(C) Rac-1-(n-propyl)-4,6-dimethyl-5-(3',4'-dimethoxybenzoyl)-1,3,6-trihydro-6-aza-3-oxapentalen-2-one 5-(3',4'-Dimethoxybenzoyl)-1,4-dimethylpyrrole-2-(α-n-propyl)-acetic acid is subjected to the procedure of Example 1, part C to produce rac-1-(n-propyl)-4,6-dimethyl-5-(3',4'-dimethoxybenzoyl)-1,3,6-trihydro-6-aza-3-oxapentalen-2-one ($R_1$=n-propyl, $R_2$=H, $R_3$=3',4'-dimethoxyphenyl, $R_4$=methyl, $R_5$=methyl, Y=CO, m=1, n=0).

EXAMPLE 112

Rac-1-(n-Propyl)-4,6-Dimethyl-5-(2',3',5'-Tribromobenzoyl)-1,3,6-Trihydro-6-Aza-3-Oxapentalen-2-One (A) Ethyl 5-(2',3',5'-tribromobenzoyl)-1,4-dimethylpyrrole-2-(α-n-propyl)-acetate The alkylation procedure of Example 77A is performed upon ethyl 5-(2',3',5'-tribromobenzoyl)-1,4-dimethylpyrrole-2-acetate (from Example 91), using an equivalent quantity of n-propyl iodide instead of methyl iodide used in Example 77A to yield ethyl 5-(2',3',5'-tribromobenzoyl)-1,4-dimethylpyrrole-2-(α-n-propyl)-acetate.

(B) 5-(2',3',5'-Tribromobenzoyl)-1,4-dimethylpyrrole-2-(α-n-propyl)-acetic acid

The hydrolysis procedure of Example 77B is followed in transforming the ester from part A of this Example into 5-(2',3',5'-tribromobenzoyl)-1,4-dimethylpyrrole-2-(α-n-propyl)-acetic acid.

(C) Rac-1-(n-propyl)-4,6-dimethyl-5-(2',3',5'-tribromobenzoyl)-1,3,6-trihydro-6-aza-3-oxapentalen-2-one 5-(2',3',5'-Tribromobenzoyl)-1,4-dimethylpyrrole-2-(α-n-propyl)-acetic acid is subjected to the procedure of Example 1, part C to produce rac-1-(n-propyl)-4,6-dimethyl-5-(2',3',5'-tribromobenzoyl)-1,3,6-trihydro-6-aza-3-oxapentalen-2-one ($R_1$=n-propyl, $R_2$=H, $R_3$2',3',5'-tribromophenyl, $R_4$=methyl, $R_5$=methyl, Y=CO, m=1, n=0).

EXAMPLE 113

Rac-1-(n-Propyl)-4,6-Dimethyl-5-(2'-Methylbenzoyl)-1,3,6-Trihydro-6-Aza-3-Oxapentalen-2-One (A) Ethyl 5-(o-methylbenzoyl)-1,4-dimethylpyrrole-2-(α-n-propyl)-acetate The alkylation procedure of Example 77A is performed upon ethyl 5-(o-methylbenzoyl)-1,4-dimethylpyrrole-2-acetate (from Example 92), using an equivalent quantity of n-propyl iodide instead of methyl iodide used in Example 77A to yield ethyl 5-(o-methylbenzoyl)-1,4-dimethylpyrrole-2-(α-n-propyl)-acetate.

(B) 5-(o-Methylbenzoyl)-1,4-dimethylpyrrole-2-(α-n-propyl)-acetic acid

The hydrolysis procedure of Example 77B is followed in transforming the ester from part A of this Example into 5-(o-methylbenzoyl)-1,4-dimethylpyrrole-2-(α-n-propyl)-acetic acid.

(C) Rac-1-(n-propyl)-4,6-dimethyl-5-(2'-methylbenzoyl)-1,3,6-trihydro-6-aza-3-oxapentalen-2-one 5-(o-Methylbenzoyl)-1,4-dimethylpyrrole-2-(α-n-propyl)-acetic acid is subjected to the procedure of Example 1, part C to produce rac-1-(n-propyl)-4,6-dimethyl-5-(2'-methylbenzoyl)-1,3,6-trihydro-6-aza-3-oxapentalen-2-one ($R_1$=n-propyl, $R_2$=H, $R_3$=2'-methylphenyl, $R_4$=methyl, $R_5$=methyl, Y=CO, m=1, n=0).

EXAMPLE 114

Rac-1-(n-Propyl)-4,6-Dimethyl-5-(4'-Cyanobenzoyl)-1,3,6-Trihydro-6-Aza-3-Oxapentalen-2-One (A) Ethyl 5-(p-cyanobenzoyl)-1,4-dimethylpyrrole-2-(α-n-propyl)-acetate The alkylation procedure of Example 77A is performed upon ethyl 5-(p-cyanobenzoyl)-1,4-dimethylpyrrole-2-acetate (from Example 93), using an equivalent quantity of n-propyl iodide instead of methyl iodide used in Example 77A to yield ethyl 5-(p-cyanobenzoyl)-1,4-dimethylpyrrole-2-(α-n-propyl)-acetate.

(B) 5-(p-Cyanobenzoyl)-1,4-dimethylpyrrole-2-(oc-n-propyl)-acetic acid

The hydrolysis procedure of Example 77B is followed in transforming the ester from part A of this Example into 5-(p-cyanobenzoyl)-1,4-dimethylpyrrole-2-(α-n-propyl)-acetic acid.

(C) Rac-1-(n-propyl)-4,6-dimethyl-5-(4'-cyanobenzoyl)-1,3,6-trihydro-6-aza-3-oxapentalen-2-one 5-(p-Cyanobenzoyl)-1,4-dimethylpyrrole-2-(α-n-propyl)-acetic acid is subjected to the procedure of Example 1, part C to produce rac-1-(n-propyl)-4,6-dimethyl-5-(4'-cyanobenzoyl)-1,3,6-trihydro-6-aza-3-oxapentalen-2-one ($R_1$=n-propyl, $R_2$=H, $R_3$=4'-cyanophenyl, $R_4$=methyl, $R_5$=methyl, Y=CO, m=1, n=0).

EXAMPLE 115

Rac-1-(n-Hexyl)-4,6-Dimethyl-5-(4'-Chlorobenzoyl)-1,3,6-Trihydro-6-Aza-3-Oxapentalen-2-One (A) Ethyl 5-(p-chlorobenzoyl)-1,4-dimethylpyrrole-2-(α-n-hexyl)-acetate The alkylation procedure of Example 77A is performed upon ethyl 5-(p-chlorobenzoyl)-1,4-dimethylpyrrole-2-acetate (from Example 84), using an equivalent quantity of n-hexyl iodide instead of methyl iodide used in Example 77A to yield ethyl 5-(p-chlorobenzoyl)-1,4-dimethylpyrrole-2-(α-n-hexyl)acetate.

(B) 5-(p-Chlorobenzoyl)-1,4-dimethylpyrrole-2-(α-n-hexyl)-acetic acid

The hydrolysis procedure of Example 77B is followed in transforming the ester from part A of this Example into 5-(p-chlorobenzoyl)-1,4-dimethylpyrrole-2-(α-n-hexyl)-acetic acid.

(C) Rac-1-(n-hexyl)-4,6-dimethyl-5-(4'-chlorobenzoyl)-1,3,6-trihydro-6-aza-3-oxapentalen-2-one 5-(p-Chlorobenzoyl)-1,4-dimethylpyrrole-2-(α-n-hexyl)-acetic acid is subjected to the procedure of Example 1, part C to produce rac-1-(n-hexyl)-4,6-dimethyl-5-(4'-chlorobenzoyl)-1,3,6-trihydro-6-aza-3-oxapentalen-2-one ($R_1$=n-hexyl, $R_2$=H, $R_3$4'-chlorophenyl, $R_4$=methyl, $R_5$=methyl, Y=CO, m=1, n=0).

EXAMPLE 116

Rac-1-(n-Hexyl)-4,6-Dimethyl-5-(4'Nitrobenzoyl)-1,3,6-Trihydro-6-Aza-3-Oxapentalen-2-One (A) Ethyl 5-(p-nitrobenzoyl)-1,4-dimethylpyrrole-2-(α-n-hexyl)-acetate The alkylation procedure of Example 77A is performed upon ethyl 5-(p-nitrobenzoyl)-1,4-dimethylpyrrole-2-acetate (from Example 85), using an equivalent quantity of n-hexyl iodide instead of methyl iodide used in Example 77A to yield ethyl 5-(p-nitrobenzoyl)-1,4-dimethylpyrrole-2-(α-n-hexyl)-acetate.

(B) 5-(p-Nitrobenzoyl)-1,4-dimethylpyrrole-2-(α-n-hexyl)-acetic acid

The hydrolysis procedure of Example 77B is followed in transforming the ester from part A of this Example into 5-(p-nitrobenzoyl)-1,4-dimethylpyrrole-2-(α-n-hexyl)-acetic acid.

(C) Rac-1-(n-hexyl)-4,6-dimethyl-5-(4'nitrobenzoyl)-1,3,6-trihydro-6-aza-3-oxapentalen-2-one 5-(p-Nitrobenzoyl)-1,4-dimethylpyrrole-2-(α-n-hexyl)-acetic acid is subjected to the procedure of Example 1, part C to produce rac-1-(n-hexyl)-4,6-dimethyl-5-(4'nitrobenzoyl)-1,3,6-trihydro-6-aza-3-oxapentalen-2-one ($R_1$=n-hexyl, $R_2$=H, $R_3$=4'-nitrophenyl, $R_4$=methyl, $R_5$=methyl, Y=CO, m=1, n=0).

EXAMPLE 117

Rac-1-(n-Hexyl)-4,6-Dimethyl-5-Benzoyl-1,3,6-Trihydro-6-Aza-3-Oxapentalen-2-One (A) Ethyl 5-benzoyl-1,4-dimethylpyrrole-2-(α-n-hexyl)-acetate The alkylation procedure of Example 77A is performed upon ethyl 5-benzoyl-1,4-dimethylpyrrole-2-acetate (from Example 86), using an equivalent quantity of n-hexyl iodide instead of methyl iodide used in Example 77A to yield ethyl 5-benzoyl-1,4-dimethylpyrrole-2-(α-n-hexyl)-acetate.

(B) 5-Benzoyl-1,4-dimethylpyrrole-2-(α-n-hexyl)-acetic acid

The hydrolysis procedure of Example 77B is followed in transforming the ester from part A of this Example into 5-benzoyl-1,4-dimethylpyrrole-2-(α-n-hexyl)-acetic acid.

(C) Rac-1-(n-hexyl)-4,6-dimethyl-5-benzoyl-1,3,6-trihydro-6-aza-3-oxapentalen-2-one 5-Benzoyl-1,4-dimethylpyrrole-2-(α-n-hexyl)-acetic acid is subjected to the procedure of Example 1, part C to produce rac-1-(n-hexyl)-4,6-dimethyl-5-benzoyl-1,3,6-trihydro-6-aza-3-oxapentalen-2-one ($R_1$=n-hexyl, $R_2$=H, $R_3$=phenyl, $R_4$=methyl, $R_5$=methyl, Y=CO, m=1, n=0).

EXAMPLE 118

Rac-1-(n-Hexyl)-4,6-Dimethyl-5-(2'-Thenoyl)-1,3,6-Trihydro-6-Aza-3-Oxapentalen-2-One (A) Ethyl 5-(2'-thenoyl)-1,4-dimethylpyrrole-2-(α-n-hexyl)-acetate The alkylation procedure of Example 77A is performed upon ethyl 5-(2'-thenoyl)-1,4-dimethylpyrrole-2-acetate (from Example 87), using an equivalent quantity of n-hexyl iodide instead of methyl iodide used in Example 77A to yield ethyl 5-(2'-thenoyl)-1,4-dimethylpyrrole-2-(α-n-hexyl)-acetate.

(B) 5-(2'-Thenoyl)-1,4-dimethylpyrrole-2-(α-n-hexyl)-acetic acid

The hydrolysis procedure of Example 77B is followed in transforming the ester from part A of this Example into 5-(2'-thenoyl)-1,4-dimethylpyrrole-2-(α-n-hexyl)-acetic acid.

(C) Rac-1-(n-hexyl)-4,6-dimethyl-5-(2'-thenoyl)-1,3,6-trihydro-6-aza-3-oxapentalen-2-one 5-(2'-Thenoyl)-1,4-dimethylpyrrole-2-(α-n-hexyl)-acetic acid is subjected to the procedure of Example 1, part C to produce rac-1-(n-hexyl)-4,6-dimethyl-5-(2'-thenoyl)-1,3,6-trihydro-6-aza-3-oxapentalen-2-one ($R_1$=n-hexyl, $R_2$=H, $R_3$=2'-thiophenyl, $R_4$=methyl, $R_5$=methyl, Y=CO, m=1, n=0).

EXAMPLE 119

Rac-1-(n-Hexyl)-4,6-Dimethyl-5-(5'-Methyl-2'-Thenoyl)-1,3,6-Trihydro-6-Aza-3-Oxapentalen-2-One (A) Ethyl 5-(5'-methylthenoyl)-1,4-dimethylpyrrole-2-(α-n-hexyl)-acetate The alkylation procedure of Example 77A is performed upon ethyl 5-(5'-methyl-2'-thenoyl)-1,4-dimethylpyrrole-2-acetate (from Example 88), using an equivalent quantity of n-hexyl iodide instead of methyl iodide used in Example 77A to yield ethyl 5-(5'-methyl-2'-thenoyl)-1,4-dimethylpyrrole-2-(α-n-hexyl)-acetate.

(B) 5-(5'-methyl-2'-thenoyl)-1,4-dimethylpyrrole-2-(α-n-hexyl)-acetic acid

The hydrolysis procedure of Example 77B is followed in transforming the ester from part A of this Example into 5-(5'-methyl-2'-thenoyl)-1,4-dimethylpyrrole-2-(α-n-hexyl)-acetic acid.

(C) Rac-1-(n-hexyl)-4,6-dimethyl-5-(5'-methyl-2'-thenoyl)-1,3,6-trihydro-6-aza-3-oxapentalen-2-one 5-(5'-Methyl-2'-thenoyl)-1,4-dimethylpyrrole-2-(α-n-hexyl)-acetic acid is subjected to the procedure of Example 1, part C to produce rac-1-(n-hexyl)-4,6-dimethyl-5-(5'-methyl-2'-thenoyl)-1,3,6-trihydro-6-aza-3-oxapentalen-2-one ($R_1$=n-hexyl, $R_2$=H, $R_3$=5'-methyl-2'-thiophenyl, $R_4$=methyl, $R_5$=methyl, Y=CO, m=1, n=0).

EXAMPLE 120

Rac-1-(n-Hexyl)-4,6-Dimethyl-5-(4'-Trifluoromethylbenzoyl)-1,3,6-Trihydro-6-Aza-3-Oxapentalen-2-One (A) Ethyl 5-(p-trifluoromethylbenzoyl)-1,4-dimethylpyrrole-2-(α-n-hexyl)-acetate The alkylation procedure of Example 77A is performed upon ethyl 5-(p-trifluoromethylbenzoyl)-1,4-dimethylpyrrole-2-acetate (from Example 89), using an equivalent quantity of n-hexyl iodide instead of methyl iodide used in Example 77A to yield ethyl 5-(p-trifluoromethylbenzoyl)-1,4-dimethylpyrrole-2-(α-n-hexyl)-acetate.

(B) 5-(p-Trifluoromethylbenzoyl)-1,4-dimethylpyrrole-2-(α-n-hexyl)-acetic acid

The hydrolysis procedure of Example 77B is followed in transforming the ester from part A of this Example into 5-(p-trifluoromethylbenzoyl)-1,4-dimethylpyrrole-2-(α-n-hexyl)-acetic acid.

(C) Rac-1-(n-hexyl)-4,6-dimethyl-5-(4'-trifluoromethylbenzoyl)-1,3,6-trihydro-6-aza-3-oxapentalen-2-one 5-(p-Trifluoromethylbenzoyl)-1,4-dimethylpyrrole-2-(α-n-hexyl)-acetic acid is subjected to the procedure of Example 1, part C to produce rac-1-(n-hexyl)-4,6-dimethyl-5-(4'-trifluoromethylbenzoyl)-1,3,6-trihydro-6-aza-3-oxapentalen-2-one ($R_1$=n-hexyl, $R_2$=H, $R_3$=4'-trifluoromethylphenyl, $R_4$=methyl, $R_5$=methyl, Y=CO, m=1, n=0).

EXAMPLE 121

Rac-1-(n-Hexyl)-4,6-Dimethyl-5-(3',4'-Dimethoxybenzoyl)-1,3,6-Trihydro-6-Aza-3-Oxapentalen-2-One (A) Ethyl 5-(3',4'-dimethoxybenzoyl)-1,4-dimethylpyrrole-2-(α-n-hexyl)-acetate The alkylation procedure of Example 77A is performed upon ethyl 5-(3',4'-dimethoxybenzoyl)-1,4-dimethylpyrrole-2-acetate (from Example 90), using an equivalent quantity of n-hexyl iodide instead of methyl iodide used in Example 77A to yield ethyl 5-(3',4'-dimethoxybenzoyl)-1,4-dimethylpyrrole-2-(α-n-hexyl)-acetate.

(B) 5-(3',4'-Dimethoxybenzoyl)-1,4-dimethylpyrrole-2-(α-n-hexyl)-acetic acid

The hydrolysis procedure of Example 77B is followed in transforming the ester from part A of this Example into 5-(3',4'-dimethoxybenzoyl)-1,4-dimethylpyrrole-2-(α-n-hexyl)-acetic acid.

(C) Rac-1-(n-hexyl)-4,6-dimethyl-5-(3',4'-dimethoxybenzoyl)-1,3,6-trihydro-6-aza-3-oxapentalen-2-one 5-(3',4'-Dimethoxybenzoyl)-1,4-dimethylpyrrole-2-(α-n-hexyl)-acetic acid is subjected to the procedure of Example 1, part C to produce rac-1-(n-hexyl)-4,6-dimethyl-5-(3',4'-dimethoxybenzoyl)-1,3,6-trihydro-6-aza-3-oxapentalen-2-one ($R_1$=n-hexyl, $R_2$=H, $R_3$=3',4'-dimethoxyphenyl, $R_4$=methyl, $R_5$=methyl, Y=CO, m=1, n=0).

EXAMPLE 122

Rac-1-(n-Hexyl)-4,6-Dimethyl-5-(2',3',5'-Tribromobenzoyl)-1,3,6-Trihydro-6-Aza-3-Oxapentalen-2-One (A) Ethyl 5-(2',3',5'-tribromobenzoyl)-1,4-dimethylpyrrole-2-(α-n-hexyl)-acetate The alkylation procedure of Example 77A is performed upon ethyl 5-(2',3',5'-tribromobenzoyl)-1,4-dimethylpyrrole-2-acetate (from Example 91), using an equivalent quantity of n-hexyl iodide instead of methyl iodide used in Example 77A to yield ethyl 5-(2',3',5'-tribromobenzoyl)-1,4-dimethylpyrrole-2-(α-n-hexyl)-acetate.

(B) 5-(2',3',5'-Tribromobenzoyl)-1,4-dimethylpyrrole-2-(α-n-hexyl)-acetic acid

The hydrolysis procedure of Example 77B is followed in transforming the ester from part A of this Example into 5-(2',3',5'-tribromobenzoyl)-1,4-dimethylpyrrole-2-(α-n-hexyl)-acetic acid (C) Rac-1-(n-hexyl)-4,6-dimethyl-5-(2',3',5'-tribromobenzoyl)-1,3,6-trihydro-6-aza-3-oxapentalen-2-one 5-(2',3',5'-Tribromobenzoyl)-1,4-dimethylpyrrole-2-(α-n-hexyl)-acetic acid is subjected to the procedure of Example 1, part C to produce rac-1-(n-hexyl)-4,6-dimethyl-5-( 2',3',5'-tribromobenzoyl)-1,3,6-trihydro-6-aza-3-oxapentalen-2-one ($R_1$=n-hexyl, $R_2$=H, $R_3$=2',3',5'-tribromophenyl, $R_4$=methyl, $R_5$=methyl, Y=CO, m=1, n=0).

EXAMPLE 123

Rac-1-(n-Hexyl)-4,6-Dimethyl-5-(2'-Methylbenzoyl)-1,3,6-Trihydro-6-Aza-3-Oxapentalen-2-One (A) Ethyl 5-(o-methylbenzoyl)-1,4-dimethylpyrrole-2-(α-n-hexyl)-acetate The alkylation procedure of Example 77A is performed upon ethyl 5-(o-methylbenzoyl)-1,4-dimethylpyrrole-2-acetate (from Example 92), using an equivalent quantity of n-hexyl iodide instead of methyl iodide used in Example 77A to yield ethyl 5-(o-methylbenzoyl)-1,4-dimethylpyrrole-2-(α-n-hexyl)-acetate.

(B) 5-(o-Methylbenzoyl)-1,4-dimethylpyrrole-2-(α-n-hexyl)-acetic acid

The hydrolysis procedure of Example 77B is followed in transforming the ester from part A of this Example into 5-(o-methylbenzoyl)-1,4-dimethylpyrrole-2-(α-n-hexyl)-acetic acid.

(C) Rac-1-(n-hexyl)-4,6-dimethyl-5-(2'-methylbenzoyl)-1,3,6-trihydro-6-aza-3-oxapentalen-2-one 5-(o-Methylbenzoyl)-1,4-dimethylpyrrole-2-(α-n-hexyl)-acetic acid is subjected to the procedure of Example 1, part C to produce rac-1-(n-hexyl)-4,6-dimethyl-5-(2'-methylbenzoyl)-1,3,6-trihydro-6-aza-3-oxapentalen-2-one ($R_1$=n-hexyl, $R_2$=H, $R_3$=2'-methylphenyl, $R_4$=methyl, $R_5$=methyl, Y=CO, m=1, n=0).

EXAMPLE 124

Rac-1-(n-Hexyl)-4,6-Dimethyl-5-(4'-Cyanobenzoyl)-1,3,6-Trihydro-6-Aza-3-Oxapentalen-2-One (A) Ethyl 5-(p-cyanobenzoyl)-1,4-dimethylpyrrole-2-(α-n-hexyl)-acetate The alkylation procedure of Example 77A is performed upon ethyl 5-(p-cyanobenzoyl)-1,4-dimethylpyrrole-2-acetate (from Example 93), using an equivalent quantity of n-hexyl iodide instead of methyl iodide used in Example 77A to yield ethyl 5-(p-cyanobenzoyl)-1,4-dimethylpyrrole-2-(α-n-hexyl)-acetate.

(B) 5-(p-Cyanobenzoyl)-1,4-dimethylpyrrole-2-(α-n-hexyl)-acetic acid

The hydrolysis procedure of Example 77B is followed in transforming the ester from part A of this Example into 5-(p-cyanobenzoyl)-1,4-dimethylpyrrole-2-(α-n-hexyl)-acetic acid.

(C) Rac-1-(n-hexyl)-4,6-dimethyl-5-(4'-cyanobenzoyl)-1,3,6-trihydro-6-aza-3-oxapentalen-2-one 5-(p-Cyanobenzoyl)-1,4-dimethylpyrrole-2-(α-n-hexyl)-acetic acid is subjected to the procedure of Example 1, part C to produce rac-1-(n-hexyl)-4,6-dimethyl-5-(4'-cyanobenzoyl)-1,3,6-trihydro-6-aza-3-oxapentalen-2-one ($R_1$=n-hexyl, $R_2$=H, $R_3$=4'-cyanophenyl, $R_4$=methyl, $R_5$=methyl, Y=CO, m=1, n=0).

EXAMPLES 125–136

4,6-Dialkyl-5-Aroyl-1,3,6-Trihydro-6-Aza-3-Oxa-Pentalen-2-One (A) By repeating the procedure of Example 76B, except that an equivalent amount of ethylamine and n-butylamine is substituted for the methylamine employed therein, there are obtained, as respective products, ethyl 3-ethoxycarbonyl-1,4-diethylpyrrole-2-acetate and ethyl 3-ethoxycarbonyl-1-n-butyl-4-ethylpyrrole-2-acetate.

(B) Similarly, by following the procedure of Example 76B, except that an equivalent amount of chloromethyl n-butyl ketone is substituted for the 1-chloro-2-butanone used therein, ethyl 3-ethoxycarbonyl-4-n-butyl-1-methylpyrrole-2-acetate is obtained.

(C) The procedure of Examples 83A through 83C are repeated, except that an equivalent amount of each of the products obtained in paragraphs A and B of this Example is substituted for the ethyl 1,4-dimetyl-3-ethoxycarbonylpyrrole-2-acetate initially employed in Example 83A, to yield, as respective final products: ethyl 1,4-diethylpyrrole-2-acetate; ethyl 1-n-butyl-4-ethylpyrrole-2-acetate; and ethyl 4-n-butyl-1-methylpyrrole-2-acetate.

(D) The Friedel-Crafts procedure of Example 83D is followed using an equivalent amount of the appropriate ester obtained in paragraph C of this Example and an equivalent amount of an appropriate Aryl chloride as the acylating agent to yield the following products: ethyl 5-(p-chlorobenzoyl)-1,4-diethylpyrrole-2-acetate; ethyl 5-(2-thenoyl)-1,4-diethylpyrrole-2-acetate; ethyl 5-(p-methylsulfonyl)-1-n-butyl-4-ethylpyrrole-2-acetate; ethyl 5-(p-trifluoromethylbenzoyl)-1-n-butyl-4-ethylpyrrole-2-acetate; ethyl 5-(p-nitrobenzoyl)-4-n-butyl-1-methylpyrrole-2-acetate; ethyl 5-(p-cyanobenzoyl)-4-n-butyl-1-methylpyrrole-2-acetate; and ethyl 5-(3',4'-dimethoxybenzoyl)-4-n-butyl-1-methylpyrrole-2-acetate.

(E) Each of the esters obtained in paragraph D of this Example is hydrolyzed in accordance with the procedure of Example 83E to yield the corresponding 5-aryl derivatives of 1,4-dialkylpyrrole-2-acetic acid.

(F) 4,6-dialkyl-5-aroyl-1,3,6-trihydro-6-aza-3-oxa-pentalen-2-one

The acids from part E are subjected to the procedure of Example 1, part C to produce the corresponding 4,6-dialkyl-5-aroyl-1,3,6-trihydro-6-aza-3-oxa-pentalen-2-ones ($R_1$=H, $R_2$=H, $R_3$=aryl, $R_4$=alkyl, $R_5$=alkyl, Y=CO, m=1, n=0).

We claim:

1. A compound of the formula:

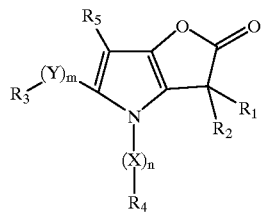

Formula I wherein $R_1$ and $R_2$ are independently selected from the group consisting of hydrogen, lower alkyl, and benzyl;

$R_3$ is selected from the group consisting of substituted or unsubstituted, pyrazinyl, piperazinyl, and pyrimidinyl, wherein said substitutents are one to three independently selected from the group consisting of halogen, lower alkyl, lower alkoxy, amino, lower alkylamino, di-lower alkylamino, hydroxy, nitro, nitrile, carboxyl, aminosulfonyl, lower alkyl mercapto, and lower alkylsulfonyl;

$R_4$ is selected from the group consisting of substituted or unsubstituted, pyrazinyl, piperazinyl, and pyrimidinyl; wherein said substitutents are one to three independently selected from the group consisting of halogen, lower alkyl, lower alkoxy, amino, lower alkylamino, di-lower alkylamino, hydroxy, nitro, nitrile, carboxyl, aminosulfonyl, lower alkyl mercapto, and lower alkylsulfonyl;

amino, lower alkyl amino, and dilower alkylamino;

Y is selected from the group consisting of $CH_2$, C=O, CH—OH m is an integer from 0–3

X is selected from the group consisting of $CH_2$, C=O, CH—OH, and $SO_2$; and n is an integer from 0–2.

2. The compound of claim 1 wherein $R_1$ and $R_2$ are independently selected from the group consisting of hydrogen, lower alkyl.

3. The compound of claim 2 wherein $R_1$ and $R_2$ are both hydrogen.

4. The compound of claim 2 wherein said substituents on said $R_3$ ring are one to three independently selected from the group consisting of lower alkyl, lower alkoxy, amino, lower alkylamino, di-lower alkylamino, carboxyl, aminosulfonyl, and lower alkylsulfonyl.

5. The compound of claim 3 wherein said substituents on said $R_3$ ring are one to three independently selected from the group consisting of lower alkyl, lower alkoxy, di-lower alkylamino, aminosulfonyl, and lower alkylsulfonyl.

6. The compound of claim 4 wherein said substituents on said $R_4$ ring are one to three independently selected from the group consisting of lower alkoxy, amino, di-lower alkylamino, hydroxy, nitrile, carboxyl, aminosulfonyl, and lower alkylsulfonyl.

7. The compound of claim 5 wherein said substituents on said $R_4$ ring are one to three independently selected from the group consisting of lower alkoxy, di-lower alkylamino, aminosulfonyl, and lower alkylsulfonyl.

8. The compound of claim 6 wherein $R_5$ is selected from the group consisting of hydrogen, lower alkyl, hydroxy, and dilower alkylamino.

9. The compound of claim 7 wherein $R_5$ is selected from the group consisting of hydrogen and lower alkyl.

10. The compound of claim 8 wherein Y is selected from the group consisting of C=O and CH—OH and m is an integer from 0–2.

11. The compound of claim 9 wherein Y is C=O, and m is 0 or 1.

12. The compound of claim 10 wherein X is selected from the group consisting of $CH_2$, C=O, and $SO_2$; and n is 0 or 1.

13. A method of treating a patient having neoplasia comprising administering a pharmacologically effective amount of a compound of Formula I to the patient with a neoplasia sensitive to such a compound:

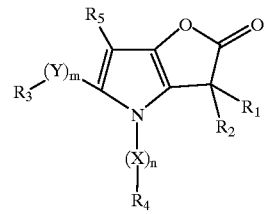

Formula I wherein $R_1$ and $R_2$ are independently selected from the group consisting of hydrogen, lower alkyl, and benzyl;

$R_3$ is selected from the group consisting of substituted or unsubstituted and pyrimidinyl, wherein said substitutents are one to three independently selected from the group consisting of halogen, lower alkyl, lower alkoxy, amino, lower alkylamino, di-lower alkylamino, hydroxy, nitro, nitrile, carboxyl, aminosulfonyl, lower alkyl mercapto, and lower alkylsulfonyl;

$R_4$ is selected from the group consisting of substituted or unsubstituted phenyl, benzyl, pyridinyl, pyrrolyl, pyrrolidinyl, pyrazolyl, pyrazolidinyl, imidazolyl, imidazolidinyl, piperidinyl, pyrazinyl, piperazinyl, pyrimidinyl, tetrazolyl, morpholinyl, triazinyl, furfuryl, thiophenyl, and lower alkyl; wherein said substitutents are one to three independently selected from the group consisting of halogen, lower alkyl, lower alkoxy, amino, lower alkylamino, di-lower alkylamino, hydroxy, nitro, nitrile, carboxyl, aminosulfonyl, lower alkyl mercapto, and lower alkylsulfonyl;

$R_5$ is selected from the group consisting of hydrogen, lower alkyl, halogen, hydroxy, amino, lower alkyl amino, and dilower alkylamino;

Y is selected from the group consisting of $CH_2$, C=O, CH—OH m is an integer from 0–3

X is selected from the group consisting of $CH_2$, C=O, CH—OH, and $SO_2$; and n is an integer from 0–2.

14. The method of claim 13 wherein $R_1$ and $R_2$ are independently selected from the group consisting of hydrogen, lower alkyl.

15. The method of claim 14 wherein $R_1$ and $R_2$ are both hydrogen.

16. The method of claim 14 wherein said substituents on said $R_3$ ring are one to three independently selected from the group consisting of lower alkyl, lower alkoxy, amino, lower alkylamino, di-lower alkylamino, carboxyl, aminosulfonyl, and lower alkylsulfonyl.

17. The method of claim 15 wherein said substituents on said $R_3$ ring are one to three independently selected from the group consisting of lower alkyl, lower alkoxy, di-lower alkylamino, aminosulfonyl, and lower alkylsulfonyl.

18. The method of claim 16 wherein said substituents on said $R_4$ ring are one to three independently selected from the group consisting of lower alkoxy, amino, di-lower alkylamino, hydroxy, nitrile, carboxyl, aminosulfonyl, and lower alkylsulfonyl.

19. The method of claim 17 wherein said substituents on said $R_4$ ring are one to three independently selected from the group consisting of lower alkoxy, di-lower alkylamino, aminosulfonyl, and lower alkylsulfonyl.

20. The method of claim 18 wherein $R_5$ is selected from the group consisting of hydrogen, lower alkyl, hydroxy, and dilower alkylamino.

21. The method of claim 19 wherein $R_5$ is selected from the group consisting of hydrogen and lower alkyl.

22. The method of claim 20 wherein Y is selected from the group consisting of C=O and CH—OH and m is an integer from 0–2.

23. The method of claim 21 wherein Y is C=O, and m is 0 or 1.

24. The method of claim 22 wherein X is selected from the group consisting of $CH_2$, C=O, and $SO_2$; and n is 0 or 1.

\* \* \* \* \*